US011596690B2

(12) United States Patent
Hu et al.

(10) Patent No.: US 11,596,690 B2
(45) Date of Patent: Mar. 7, 2023

(54) STABILIZED FORMULATIONS CONTAINING ANTI-IL-33 ANTIBODIES

(71) Applicant: Regeneron Pharmaceuticals, Inc., Tarrytown, NY (US)

(72) Inventors: Qingyan Hu, Millwood, NY (US); Dingjiang Liu, Pleasantville, NY (US)

(73) Assignee: Regeneron Pharmaceuticals, Inc., Tarytown, NY (US)

( * ) Notice: Subject to any disclaimer, the term of this patent is extended or adjusted under 35 U.S.C. 154(b) by 110 days.

(21) Appl. No.: 16/825,007

(22) Filed: Mar. 20, 2020

(65) Prior Publication Data

US 2020/0297845 A1   Sep. 24, 2020

Related U.S. Application Data

(60) Provisional application No. 62/821,661, filed on Mar. 21, 2019.

(51) Int. Cl.
| | |
|---|---|
| *A61K 39/395* | (2006.01) |
| *A61K 9/00* | (2006.01) |
| *A61K 47/12* | (2006.01) |
| *A61K 47/18* | (2017.01) |
| *A61K 47/26* | (2006.01) |
| *A61M 5/20* | (2006.01) |
| *A61M 5/32* | (2006.01) |
| *C07K 16/24* | (2006.01) |
| *A61M 5/178* | (2006.01) |

(52) U.S. Cl.
CPC ...... *A61K 39/39591* (2013.01); *A61K 9/0019* (2013.01); *A61K 47/12* (2013.01); *A61K 47/18* (2013.01); *A61K 47/26* (2013.01); *A61M 5/20* (2013.01); *A61M 5/3243* (2013.01); *C07K 16/244* (2013.01); *A61M 5/178* (2013.01); *C07K 2317/21* (2013.01); *C07K 2317/52* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 8,945,559 | B2 * | 2/2015 | Dix | A61P 17/04 424/143.1 |
| 9,453,072 | B2 | 9/2016 | Murphy et al. | |
| 10,000,564 | B2 | 6/2018 | Murphy et al. | |
| 10,519,230 | B2 | 12/2019 | Murphy et al. | |
| 2006/0088523 | A1 * | 4/2006 | Andya | A61K 39/39541 424/133.1 |
| 2010/0260770 | A1 | 10/2010 | Coyle | |

FOREIGN PATENT DOCUMENTS

| | | |
|---|---|---|
| WO | 05/079844 A2 | 9/2005 |
| WO | 08/132709 A1 | 11/2008 |
| WO | 08/144610 A1 | 11/2008 |
| WO | 11/031600 A1 | 3/2011 |
| WO | 14/164959 A2 | 10/2014 |
| WO | 17/062456 A3 | 4/2017 |
| WO | 18/102597 A1 | 6/2018 |

OTHER PUBLICATIONS

U.S. Appl. No. 62/821,661, filed Mar. 21, 2019, Expired.
PCT/US2020/023795, Mar. 20, 2020, Pending.
"AnaptysBio Announces Development of Novel Anti-IL33 Therapeutic Antibody," AnaptysBio, Inc., 1 page, (2014). [Retrieved from the Internet Jul. 3, 2014: <URL: http://www.anaptysbio.com/anti-1133/>], (Author Unknown).
Daugherty et al., "Formulation and delivery issues for monoclonal antibody therapeutics," Science Direct, vol. (58):686-706, (2006). [doi:10.1016/j.addr.2006.03.011].
Hayakawa et al., "Soluble ST2 Blocks Interleukin-33 Signaling in Allergic Airway Inflammation," Journal of Biological Chemistry, 282(36):26369-26380, (2007).
Kang et al., "Rapid Formulation Development for Monoclonal Antibodies," BioProcess International, 1-6, (2016).
Li et al., "IL-33 blockade suppresses the development of experimental autoimmune encephalomyelitis in C57BL/6 mice," Journal of Neuroimmunology, 247: 25-31, (2012).
Palmer et al., "The IL-1 receptor accessory protein (AcP) is required for IL-33 signaling and soluble AcP enhances the ability of soluble ST2 to inhibit IL-33," Cytokine, 42(3):358-364, (2008).
Palmer et al., "Interleukin-33 biology with potential insights into human diseases," Nature Reviews, Rheumatology, 7(No. ):321-329, (2011).
Wang et al., "Antibody Structure, Instability, and Formulation," Minireview, Wiley InterScience XP009084505, vol. (96.1):1-26, (2007). [DOI 10.1002/ps.20727].
WIPO Application No. PCT/US2020/023795, PCT International Search Report and Written Opinion of the International Searching Authority dated Jun. 17, 2020.

* cited by examiner

*Primary Examiner* — Yunsoo Kim
(74) *Attorney, Agent, or Firm* — Schwabe, Williamson & Wyatt PC; Lisa Dombach Flanagan

(57) ABSTRACT

The present invention provides pharmaceutical formulations comprising an antibody that specifically binds to human interleukin-33 (hIL-33). The formulations may contain, in addition to an anti-IL-33 antibody, a buffer, at least one amino acid, at least one sugar, or at least one non-ionic surfactant. The pharmaceutical formulations of the present invention exhibit a substantial degree of antibody stability after storage for several months and after being subjected to thermal and other physical stresses.

29 Claims, 4 Drawing Sheets

Specification includes a Sequence Listing.

SEQUENCE LISTING

<160> NUMBER OF SEQ ID NOS: 20

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1
gaggtgcagc tggtggagtc tgggggaaac ttggaacagc ctgggggggtc ccttagactc     60

```
tcctgtacag cctctggatt cacctttagc agatctgcca tgaactgggt ccgccgggct    120
ccagggaagg ggctggagtg ggtctcagga attagtggta gtggtggtcg aacatactac    180
gcagactccg tgaagggccg gttcaccatc tccagagaca attccaagaa tacgctatat    240
ctgcaaatga acagcctgag cgccgaggac acggccgcat attactgtgc gaaagattcg    300
tatactacca gttggtacgg aggtatggac gtctggggcc acgggaccac ggtcaccgtc    360
tcctca                                                               366

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Asn Leu Glu Gln Pro Gly Gly
1               5                   10                  15

Ser Leu Arg Leu Ser Cys Thr Ala Ser Gly Phe Thr Phe Ser Arg Ser
            20                  25                  30

Ala Met Asn Trp Val Arg Arg Ala Pro Gly Lys Gly Leu Glu Trp Val
        35                  40                  45

Ser Gly Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Ala Tyr Tyr Cys
                85                  90                  95

Ala Lys Asp Ser Tyr Thr Thr Ser Trp Tyr Gly Gly Met Asp Val Trp
            100                 105                 110

Gly His Gly Thr Thr Val Thr Val Ser Ser
        115                 120

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
gattcacctt tagcagatct gcc                                             23

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Phe Thr Phe Ser Arg Ser Ala
1               5

<210> SEQ ID NO 5
<211> LENGTH: 23
<212> TYPE: DNA
<213> ORGANISM: Artificial Sequence
<220> FEATURE:
<223> OTHER INFORMATION: Synthetic
```

<400> SEQUENCE: 5
ttagtggtag tggtggtcga aca                                        23

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ser Gly Ser Gly Gly Arg Thr
1               5

<210> SEQ ID NO 7
<211> LENGTH: 44
<212> TYPE: DNA
<213> ORGANISM: Artificial Sequence
<220> FEATURE:
<223> OTHER INFORMATION: Synthetic

<400> SEQUENCE: 7
cgaaagattc gtatactacc agttggtacg gaggtatgga cgtc                 44

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Lys Asp Ser Tyr Thr Thr Ser Trp Tyr Gly Gly Met Asp Val
1               5                   10

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcttcc gtgtctgcat ctgtaggaga cagagtcacc    60
atcacttgtc gggcgagtca gggtattttc agctggttag cctggtatca gcagaaacca   120
ggaaaagccc ctaagctcct gatctatgct gcttccagtt tacaaagtgg ggtcccatca   180
agattcagcg gcagtggatc tgggacagat ttcactctca ccatcagcag cctgcagcct   240
gaggattttg caatttacta ttgtcaacag gctaacagtg tcccgatcac cttcggccaa   300
gggacacgac tggagattaa a                                            321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Phe Ser Trp
            20                  25                  30

```
Leu Ala Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Ile Tyr Tyr Cys Gln Gln Ala Asn Ser Val Pro Ile
                85                  90                  95
Thr Phe Gly Gln Gly Thr Arg Leu Glu Ile Lys
            100                 105
```

<210> SEQ ID NO 11
<211> LENGTH: 17
<212> TYPE: DNA
<213> ORGANISM: Artificial Sequence
<220> FEATURE:
<223> OTHER INFORMATION: Synthetic

<400> SEQUENCE: 11
agggtatttt cagctgg                                                  17

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Gly Ile Phe Ser Trp
 1               5

<210> SEQ ID NO 13
<211> LENGTH: 8
<212> TYPE: DNA
<213> ORGANISM: Artificial Sequence
<220> FEATURE:
<223> OTHER INFORMATION: Synthetic

<400> SEQUENCE: 13 ctgcttcc                                                             8

<210> SEQ ID NO 14
<211> LENGTH: 2
<212> TYPE: PRT
<213> ORGANISM: Artificial Sequence
<220> FEATURE:
<223> OTHER INFORMATION: Synthetic

<400> SEQUENCE: 14

Ala Ser
 1

<210> SEQ ID NO 15
<211> LENGTH: 26
<212> TYPE: DNA
<213> ORGANISM: Artificial Sequence
<220> FEATURE:
<223> OTHER INFORMATION: Synthetic

<400> SEQUENCE: 15
aacaggctaa cagtgtcccg atcacc                                        26

```
<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gln Ala Asn Ser Val Pro Ile Thr
1               5

<210> SEQ ID NO 17
<211> LENGTH: 1350
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggaaac ttggaacagc ctgggggtc  ccttagactc      60 tcctgtacag cctctggatt caccttttagc agatctgcca tgaactgggt ccgccgggct    120
ccagggaagg ggctggagtg ggtctcagga attagtggta gtggtggtcg aacatactac    180
gcagactccg tgaagggccg gttcaccatc tccagagaca attccaagaa tacgctatat    240
ctgcaaatga acagcctgag cgccgaggac acggccgcat attactgtgc gaaagattcg    300
tatactacca gttggtacgg aggtatggac gtctggggcc acgggaccac ggtcaccgtc    360
tcctcagcct ccaccaaggg cccatcggtc ttccccctgg cgccctgctc caggagcacc    420
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccaccc tgcccagcac ctgagttcct ggggggacca    720
tcagtcttcc tgttcccccc aaaacccaag gacactctca tgatctcccg gacccctgag    780
gtcacgtgcg tggtggtgga cgtgagccag gaagacccg  aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag  cgacatcgcc   1140 gtggagtggg agagcaatgg gcagccggag aacaactaca agaccacgcc tcccgtgctg   1200
gactccgacg gctccttctt cctctacagc aggctcaccg tggacaagag caggtggcag   1260
gaggggaatg tcttctcatg ctccgtgatg catgaggctc tgcacaacca ctacacacag   1320
aagtccctct ccctgtctct gggtaaatga                                     1350

<210> SEQ ID NO 18
<211> LENGTH: 449
<212> TYPE: PRT
<213> ORGANISM: Artificial Sequence
<220> FEATURE:
<223> OTHER INFORMATION: Synthetic
```

<400> SEQUENCE: 18

```
Glu Val Gln Leu Val Glu Ser Gly Gly Asn Leu Glu Gln Pro Gly Gly
1               5                   10                  15

Ser Leu Arg Leu Ser Cys Thr Ala Ser Gly Phe Thr Phe Ser Arg Ser
            20                  25                  30

Ala Met Asn Trp Val Arg Ala Pro Gly Lys Gly Leu Glu Trp Val
        35                  40                  45

Ser Gly Ile Ser Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Ala Tyr Tyr Cys
                85                  90                  95

Ala Lys Asp Ser Tyr Thr Thr Ser Trp Tyr Gly Gly Met Asp Val Trp
            100                 105                 110

Gly His Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415
```

-continued

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 19
<211> LENGTH: 645
<212> TYPE: DNA
<213> ORGANISM: Artificial Sequence
<220> FEATURE:
<223> OTHER INFORMATION: Synthetic

<400> SEQUENCE: 19

```
gacatccaga tgacccagtc tccatcttcc gtgtctgcat ctgtaggaga cagagtcacc     60
atcacttgtc gggcgagtca gggtatttc agctggttag cctggtatca gcagaaacca    120
ggaaaagccc ctaagctcct gatctatgct gcttccagtt tacaaagtgg ggtcccatca    180
agattcagcg gcagtggatc tgggacagat ttcactctca ccatcagcag cctgcagcct    240
gaggattttg caatttacta ttgtcaacag gctaacagtg tcccgatcac cttcggccaa    300
gggacacgac tggagattaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 20
<211> LENGTH: 214
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Phe Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ala Asn Ser Val Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
                                                     -continued
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

STABILIZED FORMULATIONS CONTAINING ANTI-IL-33 ANTIBODIES

CROSS REFERENCE TO RELATED APPLICATION

This application claims the benefit under 35 USC § 119(e) of U.S. Provisional Application No. 62/821,661, filed Mar. 21, 2019, which is incorporated herein by reference in its entirety for all purposes.

REFERENCE TO A SEQUENCE LISTING

This application incorporates by reference the Sequence Listing submitted in Computer Readable Form as file 10516US01-Revised Sequence.txt, created on Jan. 12, 2022 and containing 14,453 bytes.

FIELD OF THE INVENTION

The present invention relates to the field of therapeutic antibody formulations. More specifically, the present invention relates to the field of pharmaceutical formulations comprising a human antibody that specifically binds to human interleukin-33.

BACKGROUND

Interleukin-33 (IL-33) is a ligand for ST2, a toll-like/interleukin-1 receptor super-family member that associates with an accessory protein, IL-1RAcP (for reviews, see, e.g., Kakkar and Lee, Nature Reviews—Drug Discovery 7(10): 827-840 (2008), Schmitz et al., Immunity 23:479-490 (2005); Liew et al., Nature Reviews—Immunology 10:103-110 (2010); US 2010/0260770; US 2009/0041718). Upon activation of ST2/IL-1RAcP by IL-33, a signaling cascade is triggered through downstream molecules such as MyD88 (myeloid differentiation factor 88) and TRAF6 (TNF receptor associated factor 6), leading to activation of NFκB (nuclear factor-KB), among others. IL-33 signaling has been implicated as a factor in a variety of diseases and disorders. (Liew et al., Nature Reviews—Immunology 10:103-110 (2010)).

Therapeutic macromolecules (e.g., antibodies) must be formulated in a manner that not only makes the molecules suitable for administration to patients, but also maintains their stability during storage. For example, therapeutic antibodies in liquid solution are prone to degradation, aggregation and/or undesired chemical modifications unless the solution is formulated properly. The stability of an antibody in liquid formulation depends not only on the kinds of excipients used in the formulation, but also on the amounts and proportions of the excipients relative to one another. Furthermore, other considerations aside from stability must be taken into account when preparing a liquid antibody formulation. Examples of such additional considerations include the viscosity of the solution and the concentration of antibody that can be accommodated by a given formulation. Thus, when formulating a therapeutic antibody, great care must be taken to arrive at a formulation that remains stable, contains an adequate concentration of antibody, and possesses a suitable viscosity as well as other properties which enable the formulation to be conveniently administered to patients.

Antibodies to human interleukin-33 (hIL-33) are one example of therapeutically relevant macromolecules that require proper formulation.

Although anti-hIL-33 antibodies are known in the art (see, e.g., WO 2014/164959), there remains a need for pharmaceutical formulations comprising anti-hIL-33 antibodies that are sufficiently stable and suitable for administration to patients.

BRIEF SUMMARY OF THE INVENTION

Stable liquid pharmaceutical formulations comprising an anti-IL-33 antibody and one or more excipients, as well as kits comprising such formulations and uses thereof, are provided.

In one aspect, a stable liquid pharmaceutical formulation comprising: (i) a human antibody that specifically binds to human interleukin-33 (hIL-33); (ii) a buffer; (iii) an amino acid; (iv) a thermal stabilizer; and (v) an organic cosolvent is provided. In some embodiments, the buffer is acetate or histidine at a concentration of from 1 mM to 40 mM. In some embodiments, the buffer is acetate or histidine at a concentration of from 1 mM to 20 mM. In some embodiments, the amino acid is arginine or glutamic acid at a concentration of from 30 mM to 110 mM. In some embodiments, the thermal stabilizer is sucrose at a concentration of from 1% w/v to 20% w/v. In some cases, the thermal stabilizer is sucrose at a concentration of from 1% w/v to 10% w/v. In some cases, the organic cosolvent is a surfactant at a concentration of from 0.01% w/v to 0.15% w/v. In some embodiments, the surfactant is polysorbate 80. In some embodiments, the antibody is present at a concentration of from 1 mg/ml to 200 mg/ml. In some cases, the antibody is present at a concentration of from 15 mg/ml to 150 mg/ml.

In various embodiments of the formulations, the antibody comprises the complementarity determining regions (HCDR1-HCDR2-HCDR3) of a heavy chain variable region (HCVR) comprising the amino acid sequence of SEQ ID NO: 2, and the complementarity determining regions (LCDR1-LCDR2-LCDR3) of a light chain variable region (LCVR) comprising the amino acid sequence of SEQ ID NO: 10. In some cases, the antibody comprises HCDR1-HCDR2-HCDR3 regions comprising the amino acid sequences of SEQ ID NOs: 4-6-8, respectively, and LCDR1-LCDR2-LCDR3 regions comprising the amino acid sequences of SEQ ID NOs: 12-14-16, respectively. In some embodiments, the antibody comprises a heavy chain variable region (HCVR) comprising the amino acid sequence of SEQ ID NO: 2, and a light chain variable region (LCVR) comprising the amino acid sequence of SEQ ID NO: 10. In some embodiments, the antibody has a human IgG heavy chain constant region. In some embodiments, the heavy chain constant region is of isotype IgG1. In some embodiments, the heavy chain constant region is of isotype IgG4. In some embodiments, the antibody comprises a heavy chain comprising the amino acid sequence of SEQ ID NO: 18 and a light chain comprising the amino acid sequence of SEQ ID NO: 20.

In some embodiments, the stable liquid pharmaceutical formulation comprises: (i) about 15 mg/ml to about 150 mg/mL of the human antibody that specifically binds to hIL-33; (ii) about 5 mM to about 15 mM acetate; (iii) about 60 mM to about 80 mM arginine hydrochloride; (iv) about 3% w/v to about 7% w/v sucrose; and (v) about 0.06% w/v to about 0.1% w/v polysorbate 80. In some cases, the formulation has a pH of from about 5 to about 5.6.

In some embodiments, the stable liquid pharmaceutical formulation comprises: (i) about 15 mg/ml±1.5 mg/ml of the antibody; (ii) about 10 mM±2 mM acetate; (iii) about 70 mM±14 mM arginine hydrochloride (iv) about 5% w/v±1% w/v sucrose; and (iv) about 0.08%±0.016% w/v polysorbate 80. In some embodiments, the stable liquid pharmaceutical formulation comprises: (i) about 75 mg/ml±5 mg/ml of the antibody; (ii) about 10 mM±2 mM acetate; (iii) about 70 mM±14 mM arginine hydrochloride (iv) about 5% w/v±1% w/v sucrose; and (iv) about 0.08%±0.016% w/v polysorbate 80. In some embodiments, the stable liquid pharmaceutical formulation comprises: (i) about 150 mg/ml±15 mg/ml of the antibody; (ii) about 10 mM±2 mM acetate; (iii) about 70 mM±14 mM arginine hydrochloride (iv) about 5% w/v±1% w/v sucrose; and (iv) about 0.08%±0.016% w/v polysorbate 80. In some embodiments, the stable liquid pharmaceutical formulation comprises: (i) about 15 mg/ml±1.5 mg/ml of the antibody; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80. In some embodiments, the stable liquid pharmaceutical formulation comprises: (i) about 75 mg/ml±5 mg/ml of the antibody; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80. In some embodiments, the stable liquid pharmaceutical formulation comprises: (i) about 150 mg/ml±15 mg/ml of the antibody; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80. In some cases, the pH of the formulation is from 5.2 to 5.4. In some embodiments, the pH of the formulation is about 5.3. In some embodiments, the stable liquid pharmaceutical formulation comprises: (i) about 15 mg/ml±1.5 mg/ml of the antibody; (ii) about 10 mM±2 mM acetate; (iii) about 70 mM±14 mM arginine hydrochloride (iv) about 5% w/v±1% w/v sucrose; and (iv) about 0.08%±0.04% w/v polysorbate 80. In some embodiments, the stable liquid pharmaceutical formulation comprises: (i) about 75 mg/ml±8 mg/ml of the antibody; (ii) about 10 mM±2 mM acetate; (iii) about 70 mM±14 mM arginine hydrochloride (iv) about 5% w/v±1% w/v sucrose; and (iv) about 0.08%±0.04% w/v polysorbate 80. In some embodiments, the stable liquid pharmaceutical formulation comprises: (i) about 150 mg/ml±15 mg/ml of the antibody; (ii) about 10 mM±2 mM acetate; (iii) about 70 mM±14 mM arginine hydrochloride (iv) about 5% w/v±1% w/v sucrose; and (iv) about 0.08%±0.04% w/v polysorbate 80. In some cases, the pH of the formulation is from 5.2 to 5.4. In some embodiments, the pH of the formulation is about 5.3.

In some embodiments, the stable liquid pharmaceutical formulation comprises: (i) a human antibody that specifically binds to human interleukin-33 (hIL-33) at a concentration of from 15±1.5 mg/ml to 150±15 mg/ml, wherein the antibody comprises a HCVR comprising HCDR1, HCDR2, and HCDR3 regions comprising the amino acid sequences of SEQ ID NOs: 4, 6, and 8, respectively, and LCDR1, LCDR2, and LCDR3 regions comprising the amino acid sequences of SEQ ID NOs: 12, 14, and 16, respectively; (ii) 10 mM±2 mM acetate; (iii) 70 mM±14 mM arginine hydrochloride; (iv) 5% w/v±1% w/v sucrose; and (iv) about 0.08%±0.016% w/v polysorbate 80, wherein the formulation has a pH of from 5.1 to 5.5. In some embodiments, the stable liquid pharmaceutical formulation comprises: (i) a human antibody that specifically binds to human interleukin-33 (hIL-33) at a concentration of from 15±1.5 mg/ml to 150±15 mg/ml, wherein the antibody comprises a HCVR comprising HCDR1, HCDR2, and HCDR3 regions comprising the amino acid sequences of SEQ ID NOs: 4, 6, and 8, respectively, and LCDR1, LCDR2, and LCDR3 regions comprising the amino acid sequences of SEQ ID NOs: 12, 14, and 16, respectively; (ii) 10 mM±1 mM acetate; (iii) 70 mM±7 mM arginine hydrochloride; (iv) 5% w/v±0.5% w/v sucrose; and (iv) about 0.08%±0.008% w/v polysorbate 80, wherein the formulation has a pH of from 5.1 to 5.5. In some cases, the antibody comprises a heavy chain variable region (HCVR) comprising the amino acid sequence of SEQ ID NO: 2, and a light chain variable region (LCVR) comprising the amino acid sequence of SEQ ID NO: 10. In some embodiments, the antibody has a human IgG heavy chain constant region. In some embodiments, the heavy chain constant region is of isotype IgG1. In some embodiments, the heavy chain constant region is of isotype IgG4.

In some embodiments, the stable liquid pharmaceutical formulation comprises: (i) a human antibody that specifically binds to human interleukin-33 (hIL-33) at a concentration of from 15±1.5 mg/ml to 150±15 mg/ml, wherein the antibody comprises a heavy chain comprising the amino acid sequence of SEQ ID NO: 18 and a light chain comprising the amino acid sequence of SEQ ID NO: 20; (ii) 10 mM±2 mM acetate; (iii) 70 mM±14 mM arginine hydrochloride; (iv) 5% w/v±1% w/v sucrose; and (iv) about 0.08%±0.016% w/v polysorbate 80, wherein the formulation has a pH of from 5.1 to 5.5. In some embodiments, the stable liquid pharmaceutical formulation comprises: (i) a human antibody that specifically binds to human interleukin-33 (hIL-33) at a concentration of from 15±1.5 mg/ml to 150±15 mg/ml, wherein the antibody comprises a heavy chain comprising the amino acid sequence of SEQ ID NO: 18 and a light chain comprising the amino acid sequence of SEQ ID NO: 20; (ii) 10 mM±1 mM acetate; (iii) 70 mM±7 mM arginine hydrochloride; (iv) 5% w/v±0.5% w/v sucrose; and (iv) about 0.08%±0.008% w/v polysorbate 80, wherein the formulation has a pH of from 5.1 to 5.5.

In some embodiments, the stable liquid pharmaceutical formulation contains at least 90% of the native form of the antibody after two months of storage at 5° C., as determined by size exclusion-ultra performance liquid chromatography (SE-UPLC). In some cases, the formulation contains at least 95% of the native form of the antibody after two months of storage at 5° C., as determined by SE-UPLC. In some cases, the formulation contains at least 99% of the native form of the antibody after two months of storage at 5° C., as determined by SE-UPLC.

In some cases, the formulation contains at least 95% of the native form of the antibody after nine months of storage at −20° C., as determined by SE-UPLC. In some embodiments, the stable liquid pharmaceutical formulation contains at least 97.5% of the native form of the antibody after nine months of storage at −20° C., as determined by SE-UPLC. In some cases, the formulation contains at least 99% of the native form of the antibody after nine months of storage at −20° C., as determined by SE-UPLC. In some cases, the formulation contains at least 95% of the native form of the antibody after 12 months of storage at −20° C., as determined by SE-UPLC. In some embodiments, the stable liquid pharmaceutical formulation contains at least 97.5% of the native form of the antibody after 12 months of storage at −20° C., as determined by SE-UPLC. In some cases, the formulation contains at least 99% of the native form of the antibody after 12 months of storage at −20° C., as determined by SE-UPLC. In some cases, the formulation contains at least 95% of the native form of the antibody after 18 months of storage at −20° C., as determined by SE-UPLC. In some embodiments, the stable liquid pharmaceutical formulation contains at least 97.5% of the native form of the antibody after 18 months of storage at −20° C., as determined by SE-UPLC. In some cases, the formulation contains at least 99% of the native form of the antibody after 18 months of storage at −20° C., as determined by SE-UPLC.

In some cases, the formulation contains at least 95% of the native form of the antibody after nine months of storage at 2-8° C., as determined by SE-UPLC. In some embodiments, the stable liquid pharmaceutical formulation contains at least 97.5% of the native form of the antibody after nine months of storage at 2-8° C., as determined by SE-UPLC. In some cases, the formulation contains at least 99% of the native form of the antibody after nine months of storage at 2-8° C., as determined by SE-UPLC. In some cases, the formulation contains at least 95% of the native form of the antibody after 12 months of storage at 2-8° C., as determined by SE-UPLC. In some embodiments, the stable liquid pharmaceutical formulation contains at least 97.5% of the native form of the antibody after 12 months of storage at 2-8° C., as determined by SE-UPLC. In some cases, the formulation contains at least 99% of the native form of the antibody after 12 months of storage at 2-8° C., as determined by SE-UPLC. In some cases, the formulation contains at least 95% of the native form of the antibody after 18 months of storage at 2-8° C., as determined by SE-UPLC. In some embodiments, the stable liquid pharmaceutical formulation contains at least 97.5% of the native form of the antibody after 18 months of storage at 2-8° C., as determined by SE-UPLC. In some cases, the formulation contains at least 99% of the native form of the antibody after 18 months of storage at 2-8° C., as determined by SE-UPLC.

In some embodiments, the stable liquid pharmaceutical formulation comprises no more than 2% high molecular weight (HMW) species after two months of storage at 5° C., as determined by SE-UPLC. In some cases, the formulation comprises no more than 1% HMW species after two months of storage at 5° C., as determined by SE-UPLC. In some cases, the formulation comprises no more than 0.6% HMW species after two months of storage at 5° C., as determined by SE-UPLC.

In some embodiments, the stable liquid pharmaceutical formulation comprises no more than 2% HMW species after nine months of storage at −20° C., as determined by SE-UPLC. In some cases, the formulation comprises no more than 1% HMW species after nine months of storage at −20° C., as determined by SE-UPLC. In some cases, the formulation comprises no more than 0.5% HMW species after nine months of storage at −20° C., as determined by SE-UPLC. In some embodiments, the stable liquid pharmaceutical formulation comprises no more than 2% HMW species after 12 months of storage at −20° C., as determined by SE-UPLC. In some cases, the formulation comprises no more than 1% HMW species after 12 months of storage at −20° C., as determined by SE-UPLC. In some cases, the formulation comprises no more than 0.5% HMW species after 12 months of storage at −20° C., as determined by SE-UPLC. In some embodiments, the stable liquid pharmaceutical formulation comprises no more than 2% HMW species after 18 months of storage at −20° C., as determined by SE-UPLC. In some cases, the formulation comprises no more than 1% HMW species after 18 months of storage at −20° C., as determined by SE-UPLC. In some cases, the formulation comprises no more than 0.5% HMW species after 18 months of storage at −20° C., as determined by SE-UPLC.

In some embodiments, the stable liquid pharmaceutical formulation comprises no more than 2% HMW species after nine months of storage at 2-8° C., as determined by SE-UPLC. In some cases, the formulation comprises no more than 1% HMW species after nine months of storage at 2-8° C., as determined by SE-UPLC. In some cases, the formulation comprises no more than 0.7% HMW species after nine months of storage at 2-8° C., as determined by SE-UPLC. In some embodiments, the stable liquid pharmaceutical formulation comprises no more than 2% HMW species after 12 months of storage at 2-8° C., as determined by SE-UPLC. In some cases, the formulation comprises no more than 1% HMW species after 12 months of storage at 2-8° C., as determined by SE-UPLC. In some cases, the formulation comprises no more than 0.7% HMW species after 12 months of storage at 2-8° C., as determined by SE-UPLC. In some embodiments, the stable liquid pharmaceutical formulation comprises no more than 2% HMW species after 18 months of storage at 2-8° C., as determined by SE-UPLC. In some cases, the formulation comprises no more than 1% HMW species after 18 months of storage at 2-8° C., as determined by SE-UPLC. In some cases, the formulation comprises no more than 0.7% HMW species after 18 months of storage at 2-8° C., as determined by SE-UPLC.

In some embodiments, the pharmaceutical formulation exhibits a viscosity of less than about 15 cPoise, less than about 12 cPoise, or less than about 10 cPoise, when measured at 20° C.

In some embodiments, the stable liquid pharmaceutical formulation is contained in a glass vial, a syringe, or a large volume device or bolus injector. In some embodiments, the syringe comprises a fluorocarbon-coated plunger. In some embodiments, the syringe is a low tungsten syringe. In some embodiments, the syringe contains up to 2500 ppb tungsten. In some embodiments, the syringe contains about 250-750 ppb tungsten. In some embodiments, the syringe is a pre-filled syringe. In some embodiments, the syringe is a pre-filled staked needle syringe.

In another aspect, a pen or autoinjector delivery device containing a stable liquid pharmaceutical formulation, in any of the embodiments discussed above or herein, is provided. In some cases, the delivery device is a disposable pen delivery device. In some cases, the delivery device is a reusable pen delivery device.

In another aspect, a container containing a stable liquid pharmaceutical formulation, in any of the embodiments discussed above or herein, is provided.

In another aspect, a safety system delivery device containing a stable liquid pharmaceutical formulation, in any of the embodiments discussed above or herein, is provided. In some embodiments, the safety system delivery devive includes a safety sleeve configured to extend by manual operation. In some embodiments, the safety system delivery device includes a safety sleeve configured to automatically extend following injection of the stable liquid pharmaceutical formulation.

In another aspect, a kit comprising (i) a container containing the stable liquid pharmaceutical formulation as discussed above or herein, and (ii) labeling for use of the pharmaceutical formulation is provided. In some embodiments, the labeling recites subcutaneous administration of the pharmaceutical formulation. In some embodiments, the labeling recites intravenous administration of the pharmaceutical formulation.

In another aspect, the present invention provides a unit dosage form comprising a stable liquid pharmaceutical formulation as discussed above or herein, wherein the anti-IL-33 antibody is present in an amount of from 1 mg to 500 mg. In some cases, the anti-IL-33 antibody is present in an amount of about 150 mg. In some cases, the anti-IL-33 antibody is present in an amount of about 300 mg. In some embodiments of the unit dosage form, the formulation is contained in a syringe. In some cases, the syringe is a prefilled syringe.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure. Each of the values discussed above or herein may be expressed with a variation of 1%, 5%, 10% or 20%. For example, a concentration of 10 mM may be expressed as 10 mM±0.1 mM (1% variation), 10 mM±0.5 mM (5% variation), 10 mM±1 mM (10% variation) or 10 mM±2 mM (20% variation).

Other embodiments will become apparent from a review of the detailed description.

DETAILED DESCRIPTION

Figure 1:
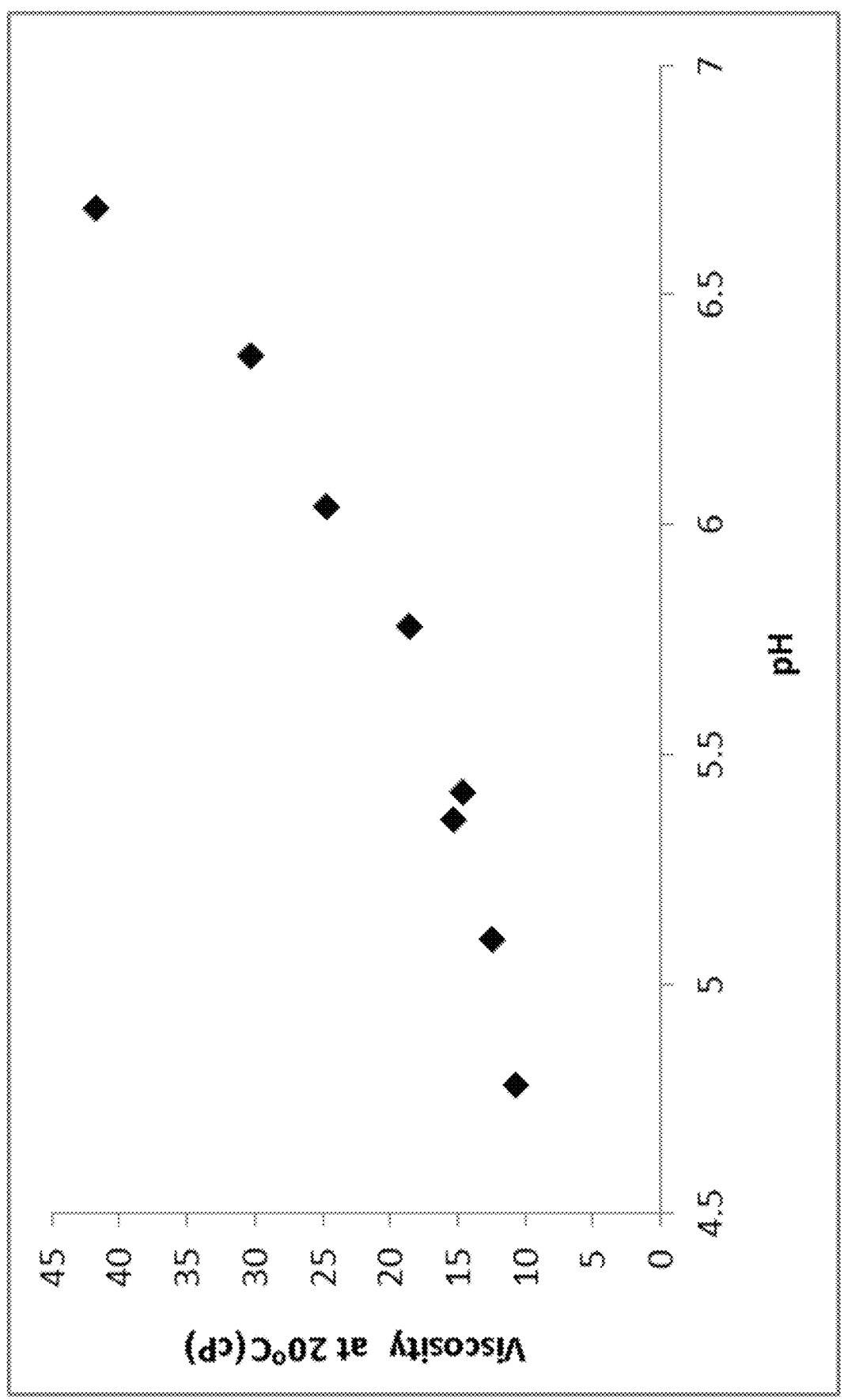
FIG. 1 shows the pH-dependent viscosity of 150 mg/mL of an anti-IL-33 antibody (mAb1).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, exemplary methods and materials are now described. All patents, applications and non-patent publications mentioned in this specification are incorporated herein by reference in their entireties.
Pharmaceutical Formulations As used herein, the expression "pharmaceutical formulation" means a combination of at least one active ingredient (e.g., an anti-IL-33 antibody, etc. which is capable of exerting a biological effect in a human or non-human animal), and at least one inactive ingredient which, when combined with the active ingredient and/or one or more additional inactive ingredients, is suitable for therapeutic administration to a human or non-human animal. The term "formulation," as used herein, means "pharmaceutical formulation" unless specifically indicated otherwise. The present invention provides pharmaceutical formulations comprising at least one therapeutic polypeptide. According to certain embodiments of the present invention, the therapeutic polypeptide is an antibody that binds specifically to human interleukin-33 (hIL-33) or an antigen-binding fragment thereof. More specifically, the present invention includes pharmaceutical formulations that comprise: (i) a human antibody that specifically binds to hIL-33; (ii) a buffer; (iii) a thermal stabilizer; (iv) a surfactant (also organic cosolvent or interfacial stabilizer); and (v) a viscosity modifier. Additional components may be included in the formulations of the present invention if such components do not significantly interfere with the viscosity and stability of the formulation. Specific exemplary components and formulations included within the present invention are described in detail below.

The pharmaceutical formulations of the present invention may, in certain embodiments, be fluid formulations. As used herein, the expression "fluid formulation" means a mixture of at least two components that exists predominantly in the fluid state at about 2° C. to about 45° C. Fluid formulations include, inter alia, liquid formulations. Fluid formulations may be of low, moderate or high viscosity depending on their particular constituents.
Antibodies that Specifically Bind Human IL-33

The pharmaceutical formulations of the present invention may comprise a human antibody, or an antigen-binding fragment thereof, that binds specifically to hIL-33. As used herein, the term "hIL-33" refers to a human IL-33 protein.

The term "antibody," as used herein, is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody." Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

In certain embodiments of the invention, the anti-IL-33 antibodies of the invention are human antibodies. The term "human antibody," as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3.

However, the term "human antibody," as used herein, is not intended to include antibodies in which CDR sequences derived from the germline of another mammalian species, such as a mouse, have been grafted onto human framework sequences. In various embodiments, the anti-IL-33 antibody is a human IgG antibody. In various embodiments, the anti-IL-33 antibody is a human antibody of isotype IgG1, IgG2, IgG3 or IgG4, or mixed isotype. In some embodiments, the anti-IL-33 antibody is a human IgG1 antibody. In some embodiments, the anti-IL-33 antibody is a human IgG4 antibody. In any of the embodiments discussed above or herein, the anti-IL-33 antibody may comprise a human kappa light chain. In any of the embodiments discussed above or herein, the anti-IL-33 antibody may comprise a human lambda light chain.

The antibodies of the invention may, in some embodiments, be recombinant human antibodies. The term "recombinant human antibody," as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The terms "antigen-binding portion" or "antigen-binding fragment" of an antibody (or simply "antibody portion" or "antibody fragment"), as used herein, refer to one or more fragments of an antibody that retain the ability to specifically bind to hIL-33.

An "isolated antibody," as used herein, is intended to refer to an antibody that is substantially free of other antibodies having different antigenic specificities (e.g., an isolated antibody that specifically binds hIL-33 is substantially free of antibodies that specifically bind antigens other than hIL-33).

The term "specifically binds," or the like, means that an antibody or antigen-binding fragment thereof forms a complex with an antigen that is relatively stable under physiologic conditions. Specific binding can be characterized by a dissociation constant of at least about $1 \times 10^{-6}$ M or greater. Methods for determining whether two molecules specifically bind are well known in the art and include, for example, equilibrium dialysis, surface plasmon resonance, and the like. An isolated antibody that specifically binds hIL-33 may, however, have cross-reactivity to other antigens, such as IL-33 molecules from other species (orthologs). In the context of the present invention, multispecific (e.g., bispecific) antibodies that bind to hIL-33 as well as one or more additional antigens are deemed to "specifically bind" hIL-33. Moreover, an isolated antibody may be substantially free of other cellular material and/or chemicals.

Exemplary anti-hIL-33 antibodies that may be included in the pharmaceutical formulations of the present invention are set forth in WO 2014/164959, the disclosure of which is incorporated by reference in its entirety.

According to certain embodiments of the present invention, the anti-hIL-33 antibody, or antigen-binding fragment thereof, comprises heavy chain complementarity determining regions HCDR1-HCDR2-HCDR3, respectively, comprising the amino acid sequences of SEQ ID NOs: 4-6-8. According to certain embodiments of the present invention, the anti-hIL-33 antibody, or antigen-binding fragment thereof, comprises light chain complementarity determining regions LCDR1-LCDR2-LCDR3, respectively, comprising the amino acid sequences of SEQ ID NOs: 12-14-16.

In certain embodiments, the anti-hIL-33 antibody, or antigen-binding fragment thereof, comprises a heavy chain variable region (HCVR) comprising the amino acid sequence of SEQ ID NO: 2. In certain embodiments, the anti-hIL-33 antibody, or antigen-binding fragment thereof, comprises a light chain variable region (LCVR) comprising the amino acid sequence of SEQ ID NO: 10. In certain embodiments, the anti-hIL-33 antibody, or antigen-binding fragment thereof, comprises a HCVR/LCVR amino acid sequence pair comprising the amino acid sequences of SEQ ID NOs: 2/10. In some embodiments, the anti-IL-33 antibody comprises a HCVR/LCVR comprising the amino acid sequences of SEQ ID NOs: 2/10, respectively, and a human IgG1 heavy chain constant region. In some embodiments, the anti-IL-33 antibody comprises a HCVR/LCVR comprising the amino acid sequences of SEQ ID NOs: 2/10, respectively, and a human IgG4 heavy chain constant region. In some embodiments, the anti-IL-33 antibody comprises a HCVR/LCVR comprising the amino acid sequences of SEQ ID NOs: 2/10, respectively, and a human IgG heavy chain constant region. In some embodiments, the anti-IL-33 antibody comprises a HCVR/LCVR comprising the amino acid sequences of SEQ ID NOs: 2/10, respectively, and a human IgG1 or IgG4 heavy chain constant region. In some embodiments, the anti-IL-33 antibody comprises a heavy chain comprising the amino acid sequence of SEQ ID NO: 18 and a light chain comprising the amino acid sequence of SEQ ID NO: 20. An anti-IL-33 antibody with a HCVR comprising the amino acid sequence of SEQ ID NO: 2 and a LCVR comprising the amino acid sequence of SEQ ID NO: 10 is referred to herein as mAb1. This antibody has a heavy chain comprising the amino acid sequence of SEQ ID NO: 18 and a light chain comprising the amino acid sequence of SEQ ID NO: 20.

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations may contain about 1 mg/mL to about 500 mg/mL of antibody; about 5 mg/mL to about 400 mg/mL of antibody; about 5 mg/mL to about 200 mg/mL of antibody; about 15 mg/mL to about 150 mg/mL; about 25 mg/mL to about 180 mg/mL of antibody; about 25 mg/mL to about 150 mg/mL of antibody; about 50 mg/mL to about 100 mg/mL; about 50 mg/mL to about 150 mg/mL; or about 140 mg/mL to about 160 mg/mL of antibody. For example, the formulations of the present invention may by liquid formulations that comprise about 1 mg/mL; about 2 mg/mL; about 5 mg/mL; about 10 mg/mL; about 15 mg/mL; about 20 mg/mL; about 25 mg/mL; about 30 mg/mL; about 35 mg/mL; about 40 mg/mL; about 45 mg/mL; about 50 mg/mL; about 55 mg/mL; about 60 mg/mL; about 65 mg/mL; about 70 mg/mL; about 75 mg/mL; about 80 mg/mL; about 85 mg/mL; about 90 mg/mL; about 95 mg/mL; about 100 mg/mL; about 105 mg/mL; about 110 mg/mL; about 115 mg/mL; about 120 mg/mL; about 125 mg/mL; about 130 mg/mL; about 131 mg/mL; about 132 mg/mL; about 133 mg/mL; about 134 mg/mL; about 135 mg/mL; about 140 mg/mL; about 145 mg/mL; about 150 mg/mL; about 155 mg/mL; about 160 mg/mL; about 165 mg/mL; about 170 mg/mL; about 175 mg/mL; about 180 mg/mL; about 185 mg/mL; about 190 mg/mL; about 195 mg/mL; or about 200 mg/mL of an antibody or an antigen-binding fragment thereof, that binds specifically to hIL-33. In certain embodiments, the pharmaceutical formulations are liquid formulations that may contain 5±0.75 mg/mL to 150±22.5 mg/mL of antibody; 7.5±1.125 mg/mL to 140±21 mg/mL of antibody; 10±1.5 mg/mL to 130±19.5 mg/mL of antibody; 12.5±1.875 mg/mL to 120±18 mg/mL of antibody; 15±2.25 mg/mL to 110±16.5 mg/mL of antibody; 17.5±2.625 mg/mL to 100±15 mg/mL of antibody; 20±3 mg/mL to 90±13.5 mg/mL of antibody; 22.5±3.375 mg/mL to 80±12 mg/mL of antibody; 25±3.75 mg/mL to 70±10.5 mg/mL of antibody; 27.5±4.125 mg/mL to 60±9 mg/mL of antibody; 30±4.5 mg/mL to 50±7.5 mg/mL of antibody; 25±3.75 mg/mL of antibody; or 50±7.5 mg/ml. In some embodiments, the pharmaceutical formulations contain from 15±0.15 mg/ml to 150±1.5 mg/ml of the anti-IL-33 antibody. In some cases, the pharmaceutical formulations contain 75 mg/mL±3.75 mg/mL of the anti-IL-33 antibody. In some cases, the pharmaceutical formulations contain 150 mg/mL±7.5 mg/mL of the anti-IL-33 antibody.

Bioequivalents

The present invention encompasses antibodies having amino acid sequences that vary from those of the exemplary molecules disclosed herein but that retain the ability to bind hIL-33. Such variant molecules may comprise one or more additions, deletions, or substitutions of amino acids when compared to parent sequence, but exhibit biological activity that is essentially equivalent to that of the antibodies discussed herein.

The present invention includes antigen-binding molecules that are bioequivalent to any of the exemplary antibodies set forth herein. Two antibodies are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antibodies are bioequivalent if there are no clinically meaningful differences in their safety, purity, and potency.

In one embodiment, two antibodies are bioequivalent if a patient can be switched one or more times between the reference product and the biological product without an expected increase in the risk of adverse effects, including a clinically significant change in immunogenicity, or diminished effectiveness, as compared to continued therapy without such switching.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Formulation Excipients and pH

The pharmaceutical formulations of the present invention comprise one or more excipients. The term "excipient," as used herein, means any non-therapeutic agent added to the formulation to provide a desired consistency, viscosity or stabilizing effect.

In certain embodiments, the pharmaceutical formulation of the invention comprises at least one amino acid (e.g., arginine, histidine or glutamic acid). In some embodiments, the amino acid is arginine. In some embodiments, the arginine is provided in the form of arginine hydrochloride. In some embodiments, the amino acid is a combination of arginine and glutamic acid. In some cases, the amino acid (e.g., arginine) acts as a viscosity modifier for the anti-IL-33 antibody formulations.

The amount of amino acid contained within the pharmaceutical formulations of the present invention may vary depending on the specific properties desired of the formulations, as well as the particular circumstances and purposes for which the formulations are intended to be used. In certain embodiments, the formulations may contain about 1 mM to about 200 mM of an amino acid; about 5 mM to about 150 mM; about 25 mM to about 125 mM of an amino acid; about 50 mM to about 100 mM of an amino acid; about 50 mM to about 90 mM of an amino acid; about 60 mM to about 80 mM of an amino acid; or about 65 mM to about 75 mM of an amino acid. For example, the pharmaceutical formulations of the present invention may comprise about 1 mM; about 5 mM; about 10 mM; about 15 mM; about 20 mM; about 25 mM; about 30 mM; about 35 mM; about 40 mM; about 45 mM; about 50 mM; about 55 mM; about 60 mM; about 65 mM; about 70 mM; about 75 mM; about 80 mM; about 85 mM; about 90 mM; about 95 mM; about 100 mM; about 105 mM; about 110 mM; about 115 mM; about 120 mM; or about 125 mM of an amino acid (e.g., arginine). In some embodiments, the formulations contain about 70 mM of an amino acid (e.g., arginine).

The pharmaceutical formulations of the present invention may also comprise one or more carbohydrates, e.g., one or more sugars. The sugar can be a reducing sugar or a non-reducing sugar. "Reducing sugars" include, e.g., sugars with a ketone or aldehyde group and contain a reactive hemiacetal group, which allows the sugar to act as a reducing agent. Specific examples of reducing sugars include fructose, glucose, glyceraldehyde, lactose, arabinose, mannose, xylose, ribose, rhamnose, galactose and maltose. Non-reducing sugars can comprise an anomeric carbon that is an acetal and is not substantially reactive with amino acids or polypeptides to initiate a Maillard reaction. Specific examples of non-reducing sugars include sucrose, trehalose, sorbose, sucralose, melezitose and raffinose. Sugar acids include, for example, saccharic acids, gluconate and other polyhydroxy sugars and salts thereof. In some embodiments, the sugar is sucrose. In some cases, the sugar (e.g., sucrose) acts as a thermal stabilizer for the anti-IL-33 antibody.

The amount of sugar (e.g., sucrose) contained within the pharmaceutical formulations of the present invention will vary depending on the specific circumstances and intended purposes for which the formulations are used. In certain embodiments, the formulations may contain about 0.1% to about 20% sugar; about 0.5% to about 20% sugar; about 1% to about 20% sugar; about 2% to about 15% sugar; about 3% to about 10% sugar; about 3% to about 7% sugar; or about 4% to about 6% sugar. For example, the pharmaceutical formulations of the present invention may comprise about 0.5%; about 1.0%; about 1.5%; about 2.0%; about 2.5%; about 3.0%; about 3.5%; about 4.0%; about 4.5%; about 5.0%; about 5.5%; about 6.0%; about 6.5%; about 7.0%; about 7.5%; about 8.0%; about 8.5%; about 9.0%; about 9.5%; about 10.0%; about 15%; or about 20% sugar (e.g., sucrose). In some embodiments, the formulations contain about 5% sugar (e.g., sucrose).

The pharmaceutical formulations of the present invention may also comprise one or more organic cosolvents (or interfacial stabilizer) in a type and in an amount that stabilizes the anti-IL-33 antibody under conditions of rough handling or agitation, such as, e.g., orbital shaking. In some embodiments, the organic cosolvent is a surfactant. As used herein, the term "surfactant" means a substance which reduces the surface tension of a fluid in which it is dissolved and/or reduces the interfacial tension between oil and water. Surfactants can be ionic or non-ionic. Exemplary non-ionic surfactants that can be included in the formulations of the present invention include, e.g., alkyl poly(ethylene oxide), alkyl polyglucosides (e.g., octyl glucoside and decyl maltoside), fatty alcohols such as cetyl alcohol and oleyl alcohol, cocamide MEA, cocamide DEA, and cocamide TEA. Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 188 (also known as Pluronic F68), poloxamer 407; polyethylene-polypropylene glycol; or polyethylene glycol (PEG). Polysorbate 20 is also known as TWEEN 20, sorbitan monolaurate and polyoxyethylenesorbitan monolaurate. In some embodiments, the surfactant is polysorbate 80.

The amount of surfactant contained within the pharmaceutical formulations of the present invention may vary depending on the specific properties desired of the formulations, as well as the particular circumstances and purposes for which the formulations are intended to be used. In certain embodiments, the formulations may contain about 0.05% to about 5% surfactant; about 0.05% to about 0.15% surfactant; about 0.04% to about 0.12%; about 0.05% to about 0.11% surfactant; about 0.06% to about 0.1% surfactant; or about 0.07% to about 0.09% surfactant. For example, the formulations of the present invention may comprise about 0.05%; about 0.06%; about 0.07%; about 0.08%; about 0.09%; about 0.10%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; or about 0.30% surfactant (e.g., polysorbate 80). In some embodiments, the formulations contain about 0.08% surfactant (e.g., polysorbate 80). Each of the percentages noted above corresponds to a percent weight/volume (w/v).

The pharmaceutical formulations of the present invention may also comprise a buffer or buffer system, which serves to maintain a stable pH and to help stabilize the anti-IL-33 antibody. In some embodiments, the buffer or buffer system comprises at least one buffer that has a buffering range that overlaps fully or in part the range of pH 4.9 to 5.7. In certain embodiments, the buffer comprises a histidine buffer. In certain embodiments, the buffer is an acetate buffer. In certain embodiments, the buffer (e.g., acetate) is present at a concentration of from about 1 mM to about 40 mM, about 1 mM to about 30 mM, about 1 mM to about 20 mM; about 3 mM to about 18 mM; about 5 mM to about 15 mM; or about 8 mM to about 12 mM. In some embodiments, the buffer (e.g., acetate) is present at a concentration of 5.3 mM±0.3 mM, 5.3 mM±0.2 mM, or 5.3 mM±0.1 mM. In some embodiments, the buffers is present at a concentration of about 4.6 mM; about 4.7 mM; about 4.8 mM; about 4.9 mM; about 5.0 mM; about 5.1 mM; about 5.2 mM; about 5.3 mM; about 5.4 mM; about 5.5 mM; about 5.6 mM; about 5.7 mM; about 5.8 mM; about 5.9 mM; or about 6.0 mM.

Exemplary Formulations

According to one aspect of the present invention, the pharmaceutical formulation comprises: (i) a human antibody that specifically binds to hIL-33 (e.g., mAb1); (ii) a buffer (e.g., acetate); (iii) an amino acid (e.g., arginine); (iv) a thermal stabilizer (e.g., sucrose); and (v) an organic cosolvent (e.g., polysorbate 80).

In some cases, the stable liquid pharmaceutical formulation comprises (i) a human antibody that specifically binds to hIL-33 (e.g., mAb1) at a concentration of from about 1 mg/ml to about 200 mg/ml; (ii) a buffer (e.g., acetate) at a concentration of from about 1 mM to about 20 mM; (iii) an amino acid (e.g., arginine) at a concentration of from about 30 mM to about 110 mM; (iv) a thermal stabilizer (e.g., sucrose) at a concentration of from about 1% w/v to about 10% w/v; and (v) an organic cosolvent (e.g., polysorbate 80) at a concentration of from about 0.01% w/v to about 0.15% w/v.

In some cases, the stable liquid pharmaceutical formulation comprises (i) a human antibody that specifically binds to hIL-33 (e.g., mAb1) at a concentration of from about 15 mg/ml to about 150 mg/ml; (ii) a buffer (e.g., acetate) at a concentration of from about 5 mM to about 15 mM; (iii) an amino acid (e.g., arginine) at a concentration of from about 50 mM to about 90 mM; (iv) a thermal stabilizer (e.g., sucrose) at a concentration of from about 3% w/v to about 7% w/v; and (v) an organic cosolvent (e.g., polysorbate 80) at a concentration of from about 0.05% w/v to about 0.11% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml; (ii) a buffer (e.g., acetate) at a concentration of from about 5 mM to about 15 mM; (iii) an amino acid (e.g., arginine) at a concentration of from about 50 mM to about 90 mM; (iv) a thermal stabilizer (e.g., sucrose) at a concentration of from about 3% w/v to about 7% w/v; and (v) an organic cosolvent (e.g., polysorbate 80) at a concentration of from about 0.05% w/v to about 0.11% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml, wherein the antibody has a heavy chain constant region of isotype IgG1;

(ii) a buffer (e.g., acetate) at a concentration of from about 5 mM to about 15 mM; (iii) an amino acid (e.g., arginine) at a concentration of from about 50 mM to about 90 mM; (iv) a thermal stabilizer (e.g., sucrose) at a concentration of from about 3% w/v to about 7% w/v; and (v) an organic cosolvent (e.g., polysorbate 80) at a concentration of from about 0.05% w/v to about 0.11% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml, wherein the antibody has a heavy chain constant region of isotype IgG4; (ii) a buffer (e.g., acetate) at a concentration of from about 5 mM to about 15 mM; (iii) an amino acid (e.g., arginine) at a concentration of from about 50 mM to about 90 mM; (iv) a thermal stabilizer (e.g., sucrose) at a concentration of from about 3% w/v to about 7% w/v; and (v) an organic cosolvent (e.g., polysorbate 80) at a concentration of from about 0.05% w/v to about 0.11% w/v.

In some cases, the stable liquid pharmaceutical formulation comprises (i) a human antibody that specifically binds to hIL-33 and comprises a heavy chain comprising the amino acid sequence of SEQ ID NO: 18 and a light chain comprising the amino acid sequence of SEQ ID NO: 20 at a concentration of from about 15 mg/ml to about 150 mg/ml; (ii) a buffer (e.g., acetate) at a concentration of from about 5 mM to about 15 mM; (iii) an amino acid (e.g., arginine) at a concentration of from about 50 mM to about 90 mM; (iv) a thermal stabilizer (e.g., sucrose) at a concentration of from about 3% w/v to about 7% w/v; and (v) an organic cosolvent (e.g., polysorbate 80) at a concentration of from about 0.05% w/v to about 0.11% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml; (ii) acetate at a concentration of from about 5 mM to about 15 mM; (iii) arginine (e.g., arginine hydrochloride) at a concentration of from about 50 mM to about 90 mM; (iv) sucrose at a concentration of from about 3% w/v to about 7% w/v; and (v) polysorbate 80 at a concentration of from about 0.05% w/v to about 0.11% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml, wherein the antibody has a heavy chain constant region of isotype IgG1; (ii) acetate at a concentration of from about 5 mM to about 15 mM; (iii) arginine (e.g., arginine hydrochloride) at a concentration of from about 50 mM to about 90 mM; (iv) sucrose at a concentration of from about 3% w/v to about 7% w/v; and (v) polysorbate 80 at a concentration of from about 0.05% w/v to about 0.11% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml, wherein the antibody has a heavy chain constant region of isotype IgG4; (ii) acetate at a concentration of from about 5 mM to about 15 mM; (iii) arginine (e.g., arginine hydrochloride) at a concentration of from about 50 mM to about 90 mM; (iv) sucrose at a concentration of from about 3% w/v to about 7% w/v; and (v) polysorbate 80 at a concentration of from about 0.05% w/v to about 0.11% w/v.

In some cases, the stable liquid pharmaceutical formulation comprises (i) a human antibody that specifically binds to hIL-33 and comprises a heavy chain comprising the amino acid sequence of SEQ ID NO: 18 and a light chain comprising the amino acid sequence of SEQ ID NO: 20 at a concentration of from about 15 mg/ml to about 150 mg/ml; (ii) acetate at a concentration of from about 5 mM to about 15 mM; (iii) arginine (e.g., arginine hydrochloride) at a concentration of from about 50 mM to about 90 mM; (iv) sucrose at a concentration of from about 3% w/v to about 7% w/v; and (v) polysorbate 80 at a concentration of from about 0.05% w/v to about 0.11% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml; (ii) acetate at a concentration of from about 8 mM to about 12 mM; (iii) arginine (e.g., arginine hydrochloride) at a concentration of from about 65 mM to about 75 mM; (iv) sucrose at a concentration of from about 4% w/v to about 6% w/v; and (v) polysorbate 80 at a concentration of from about 0.07% w/v to about 0.09% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml, wherein the antibody has a heavy chain constant region of isotype IgG1; (ii) acetate at a concentration of from about 8 mM to about 12 mM; (iii) arginine (e.g., arginine hydrochloride) at a concentration of from about 65 mM to about 75 mM; (iv) sucrose at a concentration of from about 4% w/v to about 6% w/v; and (v) polysorbate 80 at a concentration of from about 0.07% w/v to about 0.09% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml, wherein the antibody has a heavy chain constant region of isotype IgG4; (ii) acetate at a concentration of from about 8 mM to about 12 mM; (iii) arginine (e.g., arginine hydrochloride) at a concentration of from about 65 mM to about 75 mM; (iv) sucrose at a concentration of from about 4% w/v to about 6% w/v; and (v) polysorbate 80 at a concentration of from about 0.07% w/v to about 0.09% w/v.

In some cases, the stable liquid pharmaceutical formulation comprises (i) a human antibody that specifically binds to hIL-33 and comprises a heavy chain comprising the amino acid sequence of SEQ ID NO: 18 and a light chain comprising the amino acid sequence of SEQ ID NO: 20 at a concentration of from about 15 mg/ml to about 150 mg/ml; (ii) acetate at a concentration of from about 8 mM to about 12 mM; (iii) arginine (e.g., arginine hydrochloride) at a concentration of from about 65 mM to about 75 mM; (iv) sucrose at a concentration of from about 4% w/v to about 6% w/v; and (v) polysorbate 80 at a concentration of from about 0.07% w/v to about 0.09% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml; (ii) acetate at a concentration of about 10 mM; (iii) arginine (e.g., arginine hydrochloride) at a concentration of about 70 mM; (iv) sucrose at a concentration of about 5% w/v; and (v) polysorbate 80 at a concentration of about 0.08% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml, wherein the antibody has a heavy chain constant region of isotype IgG1; (ii) acetate at a concentration of about 10 mM; (iii) arginine (e.g., arginine hydrochloride) at a concentration of about 70 mM; (iv) sucrose at a concentration of about 5% w/v; and (v) polysorbate 80 at a concentration of about 0.08% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml, wherein the antibody has a heavy chain constant region of isotype IgG4; (ii) acetate at a concentration of about 10 mM; (iii) arginine (e.g., arginine hydrochloride) at a concentration of about 70 mM; (iv) sucrose at a concentration of about 5% w/v; and (v) polysorbate 80 at a concentration of about 0.08% w/v.

In some cases, the stable liquid pharmaceutical formulation comprises (i) a human antibody that specifically binds to hIL-33 and comprises a heavy chain comprising the amino acid sequence of SEQ ID NO: 18 and a light chain comprising the amino acid sequence of SEQ ID NO: 20 at a concentration of from about 15 mg/ml to about 150 mg/ml; (ii) acetate at a concentration of about 10 mM; (iii) arginine (e.g., arginine hydrochloride) at a concentration of about 70 mM; (iv) sucrose at a concentration of about 5% w/v; and (v) polysorbate 80 at a concentration of about 0.08% w/v.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of from about 15 mg/ml to about 150 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of about 15 mg/ml±1.5 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of about 75 mg/ml±5 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a HCVR comprising the amino acid sequence of SEQ ID NO: 2 and a LCVR comprising the amino acid sequence of SEQ ID NO: 10 at a concentration of about 150 mg/ml±15 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a HCVR comprising the amino acid sequence of SEQ ID NO: 2, a LCVR comprising the amino acid sequence of SEQ ID NO: 10 and a human IgG4 heavy chain constant region at a concentration of from about 15 mg/ml to about 150 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a HCVR comprising the amino acid sequence of SEQ ID NO: 2, a LCVR comprising the amino acid sequence of SEQ ID NO: 10 and a human IgG4 heavy chain constant region at a concentration of about 15 mg/ml±1.5 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a HCVR comprising the amino acid sequence of SEQ ID NO: 2, a LCVR comprising the amino acid sequence of SEQ ID NO: 10 and a human IgG4 heavy chain constant region at a concentration of about 75 mg/ml±5 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a HCVR comprising the amino acid sequence of SEQ ID NO: 2, a LCVR comprising the amino acid sequence of SEQ ID NO: 10 and a human IgG4 heavy chain constant region at a concentration of about 150 mg/ml±15 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a heavy chain comprising the amino acid sequence of SEQ ID NO: 18 and a light chain comprising the amino acid sequence of SEQ ID NO: 20 at a concentration of from about 15 mg/ml to about 150 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a heavy chain comprising the amino acid sequence of SEQ ID NO: 18 and a light chain comprising the amino acid sequence of SEQ ID NO: 20 at a concentration of about 15 mg/ml±1.5 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a heavy chain comprising the amino acid sequence of SEQ ID NO: 18 and a light chain comprising the amino acid sequence of SEQ ID NO: 20 at a concentration of about 75 mg/ml±5 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

In some cases, the stable liquid pharmaceutical formulation comprises (i) a human antibody that specifically binds to hIL-33 and comprises a heavy chain comprising the amino acid sequence of SEQ ID NO: 18 and a light chain comprising the amino acid sequence of SEQ ID NO: 20 at a concentration of about 150 mg/ml±15 mg/ml; (ii) about 10 mM±1 mM acetate; (iii) about 70 mM±7 mM arginine hydrochloride (iv) about 5% w/v±0.5% w/v sucrose; and (iv) about 0.08%±0.008% w/v polysorbate 80, wherein the formulation has a pH of from 5.3±0.1.

Additional non-limiting examples of pharmaceutical formulations encompassed by the present invention are set forth elsewhere herein, including the working Examples presented below.

Stability and Viscosity of the Pharmaceutical Formulations

The pharmaceutical formulations of the present invention exhibit high levels of stability. The term "stable," as used herein in reference to the pharmaceutical formulations, means that the antibodies within the pharmaceutical formulations retain an acceptable degree of structure and/or function and/or biological activity after storage for a defined amount of time. A formulation may be stable even though the antibody contained therein does not maintain 100% of its structure and/or function and/or biological activity after storage for a defined amount of time. Under certain circumstances, maintenance of about 90%, about 95%, about 96%, about 97%, about 98% or about 99% of an antibody's structure and/or function and/or biological activity after storage for a defined amount of time may be regarded as "stable."

Stability can be measured by, inter alia, determining the percentage of native antibody remaining in the formulation after storage for a defined amount of time at a given temperature. The percentage of native antibody can be determined by, inter alia, size exclusion chromatography (e.g., size exclusion high performance liquid chromatography [SE-HPLC]). An "acceptable degree of stability," as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a given temperature. The defined amount of time after which stability is measured can be at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 30 months, at least 36 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C., or about 45° C. For example, a pharmaceutical formulation may be deemed stable if after 3 months of storage at 5° C., greater than about 90%, 95%, 96% or 97% of native antibody is detected by SE-HPLC. A pharmaceutical formulation may also be deemed stable if after 6 months of storage at 5° C., greater than about 90%, 95%, 96% or 97% of native antibody is detected by SE-HPLC. A pharmaceutical formulation may also be deemed stable if after 9 months of storage at 5° C., greater than about 90%, 95%, 96%, 96.5%, 97%, 97.5%, 98%, 98.5%, 99% or 99.5% of native antibody is detected by SE-HPLC. A pharmaceutical formulation may also be deemed stable if after 3 months of storage at 25° C., greater than about 90%, 95%, 96%, 96.5%, 97%, 97.5%, 98%, 98.5%, 99% or 99.5% of native antibody is detected by SE-HPLC. A pharmaceutical formulation may also be deemed stable if after 6 months of storage at 25° C., greater than about 90%, 95%, 96%, 96.5%, 97%, 97.5%, 98%, 98.5%, 99% or 99.5% of native antibody is detected by SE-HPLC. A pharmaceutical formulation may also be deemed stable if after 9 months of storage at 25° C., greater than about 90%, 95%, 96%, 96.5%, 97%, 97.5%, 98%, 98.5%, 99% or 99.5% of native antibody is detected by SE-HPLC.

Other methods may be used to assess the stability of the formulations of the present invention such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at t=0.

Measuring the binding affinity of the antibody to its target may also be used to assess stability. For example, a formulation of the present invention may be regarded as stable if, after storage at e.g., −80° C., −30° C., −20° C., 5° C., 25° C., 37° C., 45° C., etc. for a defined amount of time (e.g., 14 days to 9 months), the anti-IL-33 antibody contained within the formulation binds to hIL-33 with an affinity that is at least 80%, 85%, 90%, 95%, or more of the binding affinity of the antibody prior to said storage. Binding affinity may be determined by any method, such as e.g., ELISA or plasmon resonance. Biological activity may be determined by an IL-33 activity assay, such as by contacting a cell that expresses IL-33 with the formulation comprising the anti-IL-33 antibody. The binding of the antibody to such a cell may be measured directly, such as via FACS analysis. Alternatively, the downstream activity of the IL-33 system may be measured in the presence of the antibody, and compared to the activity of the IL-33 system in the absence of antibody.

Stability can be measured, inter alia, by determining the percentage of antibody that forms an aggregate within the formulation after storage for a defined amount of time at a defined temperature, wherein stability is inversely proportional to the percent aggregate that is formed. The percentage of aggregated antibody can be determined by, inter alia, size exclusion chromatography (e.g., size exclusion high performance liquid chromatography [SE-HPLC] or size exclusion ultra-performance liquid chromatography [SE-UPLC]). An "acceptable degree of stability", as that phrase is used herein, means that at most 6% of the antibody is in an aggregated form detected in the formulation after storage for a defined amount of time at a given temperature. In certain embodiments an acceptable degree of stability means that at most about 6%, 5%, 4%, 3%, 2%, 1%, 0.5%, or 0.1% of the antibody can be detected in an aggregate in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 30 months, at least 36 months, or more. The temperature at which the pharmaceutical formulation may be stored when assessing stability can be any temperature from about −80° C. to about 45° C., e.g., storage at about −80° C., about −30° C., about −20° C., about 0° C., about 4°–8° C., about 5° C., about 25° C., about 35° C., about 37° C. or about 45° C. For example, a pharmaceutical formulation may be deemed stable if after nine months of storage at 5° C., less than about 2%, 1.75%, 1.5%, 1.25%, 1%, 0.75%, 0.5%, 0.25%, or 0.1% of the antibody is detected in an aggregated form. A pharmaceutical formulation may also be deemed stable if after six months of storage at 25° C., less than about 2%, 1.75%, 1.5%, 1.25%, 1%, 0.75%, 0.5%, 0.25%, or 0.1% of the antibody is detected in an aggregated form. A pharmaceutical formulation may also be deemed stable if after 28 days of storage at 45° C., less than about 4%, 3.5%, 3%, 2.5%, 2%, 1.5%, 1%, 0.5%, or 0.1% of the antibody is detected in an aggregated form. A pharmaceutical formulation may also be deemed stable if after three months of storage at −20° C., −30° C., or −80° C. less than about 2%, 1.9%, 1.8%, 1.7%, 1.6%, 1.5%, 1%, 0.5%, or 0.1% of the antibody is detected in an aggregated form.

Stability can be measured, inter alia, by determining the percentage of antibody that migrates in a more acidic fraction during ion exchange ("acidic form") than in the main fraction of antibody ("main charge form"), wherein stability is inversely proportional to the fraction of antibody in the acidic form. While not wishing to be bound by theory, deamidation of the antibody may cause the antibody to become more negatively charged and thus more acidic relative to the non-deamidated antibody (see, e.g., Robinson, N., Protein Deamidation, PNAS, Apr. 16, 2002, 99(8):5283-5288). The percentage of "acidified" antibody can be determined by ion exchange chromatography (e.g., cation exchange high performance liquid chromatography [CEX-HPLC] or cation exchange ultra-performance liquid chromatography [CEX-UPLC]). An "acceptable degree of stability", as that phrase is used herein, means that at most 52% of the antibody is in a more acidic form detected in the formulation after storage for a defined amount of time at a defined temperature. In certain embodiments an acceptable degree of stability means that at most about 52%, 50%, 45%, 40%, 35%, 30%, 29%, 28%, 27%, 26%, 25%, 20%, 15%, 10%, 5%, 4%, 3%, 2%, 1%, 0.5%, or 0.1% of the antibody can be detected in an acidic form in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 30 months, at least 36 months, or more. The temperature at which the pharmaceutical formulation may be stored when assessing stability can be any temperature from about −80° C. to about 45° C., e.g., storage at about −80° C., about −30° C., about −20° C., about 0° C., about 4°–8° C., about 5° C., about 25° C., or about 45° C. For example, a pharmaceutical formulation may be deemed stable if after three months of storage at −80° C., −30° C., or −20° C. less than about 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after nine months of storage at 5° C., less than about 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 25° C., less than about 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 37° C., less than about 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 45° C., less than about 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody can be detected in a more acidic form.

In certain embodiments, a "stable" pharmaceutical composition or pharmaceutical formulation of the present invention comprises no more than 2%, no more than 1.9%, no more than 1.8%, no more than 1.7%, no more than 1.6%, or no more than 1.5% HMW species, as measured by size exclusion ultra-performance liquid chromatography (SE-UPLC) after 24 months of storage at −80° C., −30° C. or −20° C. In certain embodiments, a "stable" pharmaceutical composition or pharmaceutical formulation of the present invention comprises no more than 1%, no more than 0.9%, no more than 0.8%, no more than 0.7%, no more than 0.6%, or no more than 0.5% HMW species, as measured by SE-UPLC after nine months of storage at −80° C., −30° C. or −20° C. In certain embodiments, a "stable" pharmaceutical composition or pharmaceutical formulation of the present invention comprises no more than 1%, no more than 0.9%, no more than 0.8%, no more than 0.7%, or no more than 0.6% HMW species, as measured by SE-UPLC after two months of storage at 5° C. In certain embodiments, a "stable" pharmaceutical composition or pharmaceutical formulation of the present invention comprises no more than 2%, no more than 1.8%, no more than 1.6%, no more than 1.4%, no more than 1.2%, or no more than 1.0% HMW species, as measured by SE-UPLC after two months of storage at 25° C. and 60% relative humidity. In certain embodiments, a "stable" pharmaceutical composition or pharmaceutical formulation of the present invention comprises no more than 6%, no more than 5.5%, no more than 5.4%, no more than 5.3%, no more than 5.2%, or no more than 5.1% HMW species, as measured by SE-UPLC after two months of storage at 40° C. and 75% relative humidity. In certain embodiments, a "stable" pharmaceutical composition or pharmaceutical formulation of the present invention comprises no more than 1%, no more than 0.9%, no more than 0.8%, or no more than 0.7% HMW species, as measured by SE-UPLC after nine months of storage at 2-8° C. In certain embodiments, a "stable" pharmaceutical composition or pharmaceutical formulation of the present invention comprises no more than 3%, no more than 2.8%, no more than 2.6%, no more than 2.4%, no more than 2.2%, or no more than 2.0% HMW species, as measured by SE-UPLC after 24 months of storage at 2-8° C. In certain embodiments, a "stable" pharmaceutical composition or pharmaceutical formulation of the present invention comprises no more than 2%, no more than 1.8%, no more than 1.6%, no more than 1.5%, no more than 1.4%, or no more than 1.3% HMW species, as measured by SE-UPLC after six months of storage at 25° C. and 60% relative humidity. In certain embodiments, a "stable" pharmaceutical composition or pharmaceutical formulation of the present invention comprises no more than 1%, no more than 0.9%, no more than 0.8%, or no more than 0.7% HMW species, as measured by SE-UPLC after six months of storage at 2-8° C. In certain embodiments, a "stable" pharmaceutical composition or pharmaceutical formulation of the present invention comprises no more than 1%, no more than 0.9%, no more than 0.8%, no more than 0.7%, no more than 0.6%, or no more than 0.5% HMW species, as measured by SE-UPLC after three months of storage at 2-8° C.

In certain embodiments, a "stable" pharmaceutical composition or pharmaceutical formulation of the present invention comprises at least 95%, at least 96%, at least 97%, at least 97.5%, or at least 97.9% native form of the antibody, as measured by size exclusion ultra-performance liquid chromatography (SE-UPLC) after 24 months of storage at −80° C., −30° C. or −20° C. In certain embodiments, a "stable" pharmaceutical composition or pharmaceutical formulation of the present invention comprises at least 95%, at least 96%, at least 97%, at least 98%, or at least 99% native form of the antibody, as measured by size exclusion ultra-performance liquid chromatography (SE-UPLC) after nine months of storage at −80° C., −30° C. or −20° C. In certain embodiments, a "stable" pharmaceutical composition or pharmaceutical formulation of the present invention comprises at least 95%, at least 96%, at least 97%, at least 98%, or at least 99% native form of the antibody, as measured by size exclusion ultra-performance liquid chromatography (SE-UPLC) after two months of storage at 5° C. In certain embodiments, a "stable" pharmaceutical composition or pharmaceutical formulation of the present invention comprises at least 95%, at least 96%, at least 97%, at least 98%, at least 98.5%, or at least 98.8% native form of the antibody, as measured by size exclusion ultra-performance liquid chromatography (SE-UPLC) after two months of storage at 25° C. and 60% relative humidity. In certain embodiments, a "stable" pharmaceutical composition or pharmaceutical formulation of the present invention comprises at least 90%, at least 91%, at least 92%, at least 93%, at least 94%, or at least 94.1% native form of the antibody, as measured by size exclusion ultra-performance liquid chromatography (SE-UPLC) after two months of storage at 40° C. and 75% relative humidity. In certain embodiments, a "stable" pharmaceutical composition or pharmaceutical formulation of the present invention comprises at least 95%, at least 96%, at least 97%, at least 98%, or at least 99% native form of the antibody, as measured by size exclusion ultra-performance liquid chromatography (SE-UPLC) after nine months of storage at 2-8° C. In certain embodiments, a "stable" pharmaceutical composition or pharmaceutical formulation of the present invention comprises at least 95%, at least 96%, at least 97%, at least 97.5%, or at least 97.6% native form of the antibody, as measured by size exclusion ultra-performance liquid chromatography (SE-UPLC) after 24 months of storage at 2-8° C. In certain embodiments, a "stable" pharmaceutical composition or pharmaceutical formulation of the present invention comprises at least 95%, at least 96%, at least 97%, at least 98%, or at least 98.4% native form of the antibody, as measured by size exclusion ultra-performance liquid chromatography (SE-UPLC) after six months of storage at 25° C. and 60% relative humidity. In certain embodiments, a "stable" pharmaceutical composition or pharmaceutical formulation of the present invention comprises at least 95%, at least 96%, at least 97%, at least 98%, or at least 99% native form of the antibody, as measured by size exclusion ultra-performance liquid chromatography (SE-UPLC) after three or after six months of storage at 2-8° C.

References to stability of the pharmaceutical formulations "after" a specified period of time are intended to mean that a measurement of a stability parameter (e.g., % native form, % HMW species, or % acidic form) is taken at or about the end of the specific time period, and is not intended to mean that the pharmaceutical formulation necessarily maintains the same degree of stability for the measured parameter thereafter. For example, reference to a particular stability after 9 months means that the measurement of stability was taken at or about 9 months after the start of the study. Additional methods for assessing the stability of an antibody in formulation are demonstrated in the Examples presented below.

In the fluid form, the pharmaceutical formulations of the present invention may, in certain embodiments, exhibit low to moderate levels of viscosity. "Viscosity" as used herein may be "kinematic viscosity" or "absolute viscosity." "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the second fluid is twice as viscous as the first on a kinematic viscosity scale. "Absolute viscosity," sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

As used herein, a low level of viscosity, in reference to a fluid formulation of the present invention, will exhibit an absolute viscosity of less than about 20 cPoise (cP) at 20° C. For example, a fluid formulation of the invention will be deemed to have "low viscosity," if, when measured using standard viscosity measurement techniques, the formulation exhibits an absolute viscosity of about 19 cP, about 18 cP, about 17 cP, about 16 cP, about 15 cP, about 14 cP, about 13 cP, about 12 cP, about 11 cP, about 10 cP, about 9 cP, about 8 cP, about 7 cP, about 6 cP, about 5 cP, about 4 cP, or less. As used herein, a moderate level of viscosity, in reference to a fluid formulation of the present invention, will exhibit an absolute viscosity of between about 30 cP and about 20 cP. For example, a fluid formulation of the invention will be deemed to have "moderate viscosity," if when measured using standard viscosity measurement techniques, the formulation exhibits an absolute viscosity of about 30 cP, about 29 cP, about 28 cP, about 27 cP, about 26 cP, about 25 cP, about 24 cP, about 23 cP, about 22 cP, about 21 cP or about 20 cP. Each of these values refers to a measurement taken at 20° C.

As illustrated in the Examples below, the present invention is based, in part, on the discovery that the combination of claimed excipients with an anti-IL-33 antibody produces a formulation that is stable and has a desirable viscosity.

Containers and Methods of Administration

The pharmaceutical formulations of the present invention may be contained within any container suitable for storage of medicines and other therapeutic compositions. For example, the pharmaceutical formulations may be contained within a sealed and sterilized plastic or glass container having a defined volume such as a vial, ampule, syringe, cartridge, bottle or IV bag. Different types of vials can be used to contain the formulations of the present invention including, e.g., clear and opaque (e.g., amber) glass or plastic vials. Likewise, any type of syringe can be used to contain and/or administer the pharmaceutical formulations of the present invention. In some embodiments, the pharmaceutical formulation is contained in a prefilled syringe. In some embodiments, the pharmaceutical formulation is contained in a prefilled staked needle syringe.

The pharmaceutical formulations of the present invention may be contained within "normal tungsten" syringes or "low tungsten" syringes. As will be appreciated by persons of ordinary skill in the art, the process of making glass syringes generally involves the use of a hot tungsten rod which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than 500 parts per billion (ppb) of tungsten. The term "low tungsten" means that the syringe contains less than 500 ppb of tungsten. For example, a low tungsten syringe, according to the present invention, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial and/or to preserve their stability. Thus, pharmaceutical formulations of the present invention, according to certain embodiments, may be contained within a syringe that comprises a coated plunger, or within a vial that is sealed with a coated rubber stopper. For example, the plunger or stopper may be coated with a fluorocarbon film. Examples of coated stoppers and/or plungers suitable for use with vials and syringes containing the pharmaceutical formulations of the present invention are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present invention are commercially available under the tradename "FluroTec®," available from West Pharmaceutical Services, Inc. (Lionville, Pa.). According to certain embodiments of the present invention, the pharmaceutical formulations may be contained within a low tungsten syringe that comprises a fluorocarbon-coated plunger. In some embodiments, the container is a syringe, such as an Ompi EZ-Fill™ syringe or a BD Neopak™ syringe. In some cases, the syringe is a 1 mL long glass syringe with a 1 mL iWest piston, a 27G thin wall needle and an FM30 needle shield or a BD260 needle shield. In some cases, the syringe is a 2.25 mL glass syringe with a West NovaPure™ 1-3 mL piston, a 27G thin wall needle and an FM30 needle shield or a BD260 needle shield. In various embodiments, the syringe is a 0.5 mL, 0.6 mL, 0.7 mL, 0.8 mL, 0.9 mL, 1.0 mL, 1.1 mL, 1.2 mL, 1.3 mL, 1.4 mL, 1.5 mL, 1.6 mL, 1.7 mL, 1.8 mL, 1.9 mL, 2.0 mL, 2.1 mL, 2.2 mL, 2.3 mL, 2.4 mL, 2.5 mL, 2.6 mL, 2.7 mL, 2.8 mL, 2.9 mL, 3.0 mL, 3.5 mL, 4.0 mL, 4.5 mL, 5.0 mL, 5.5 mL, 6.0 mL, 6.5 mL, 7.0 mL, 7.5 mL, 8.0 mL, 8.5 mL, 9.0 mL, 9.5 mL, or 10 mL syringe (e.g., a glass syringe).

The pharmaceutical formulations can be administered to a patient by parenteral routes such as injection (e.g., subcutaneous, intravenous, intramuscular, intraperitoneal, etc.) or percutaneous, mucosal, nasal, pulmonary and/or oral administration. Numerous reusable pen and/or autoinjector delivery devices can be used to subcutaneously deliver the pharmaceutical formulations of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen and/or autoinjector delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park, Ill.), to name only a few. In some cases, the pharmaceutical formulation is contained in a syringe specifically adapted for use with an autoinjector. Subcutaneous injections may be administered using a 20-30 gauge needle, or a 25-30 gauge needle. In some cases, subcutaneous injections may be administered using a 25 gaude needle. In some cases, subcutaneous injections may be administered using a 27 gaude needle. In some cases, subcutaneous injections may be administered using a 29 gaude needle.

Another type of delivery device can include a safety system. Such devices can be relatively inexpensive, and operate to manually or automatically extend a safety sleeve over a needle once injection is complete. Examples of safety systems can include the ERIS device by West Pharmaceutical, or the UltraSafe device by Becton Dickinson. In addition, the use of a large volume device ("LVD"), or bolus injector, to deliver the pharmaceutical formulations of the present invention is also contemplated herein. In some cases, the LVD or bolus injector may be configured to inject a medicament into a patient. For example, an LVD or bolus injector may be configured to deliver a "large" volume of medicament (typically about 2 ml to about 10 ml).

The pharmaceutical formulations of the present invention can also be contained in a unit dosage form. The term "unit dosage form," as used herein, refers to a physically discrete unit suitable as a unitary dosage for the patient to be treated, each unit containing a predetermined quantity of active compound calculated to produce the desired therapeutic effect in association with the required pharmaceutical carrier, diluent, or excipient. In various embodiments, the unit dosage form is contained within a container as discussed herein. Actual dosage levels of the active ingredient (e.g., an anti-IL-33 antibody) in the formulations of the present invention may be varied so as to obtain an amount of the active ingredient which is effective to achieve the desired therapeutic response for a particular patient, composition, and mode of administration, without adverse effect to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. The term "diluent" as used herein refers to a solution suitable for altering or achieving an exemplary or appropriate concentration or concentrations as described herein.

In various embodiments, the unit dosage form contains an amount of the active ingredient (e.g., an anti-IL-33 antibody) intended for a single use. In various embodiments, the amount of the active ingredient in the unit dosage form is from about 0.1 mg to about 5000 mg, from about 100 mg to about 1000 mg, and from about 100 mg to about 500 mg, from about 100 mg to about 400 mg, from about 100 mg to about 200 mg, from about 250 mg to about 350 mg, from about 125 mg to about 175 mg, from about 275 mg to about 325 mg, or ranges or intervals thereof. Ranges intermediate to the above recited amounts, for example, from about 135 mg to about 165 mg or 285 mg to 315 mg, are also intended to be part of this invention. For example, ranges of values using a combination of any of the above recited values (or values contained within the above recited ranges) as upper and/or lower limits are intended to be included. In a particular embodiment, the formulation often is supplied as a liquid in unit dosage form. In some embodiments, the unit dosage form contains about 150 mg. In some embodiments, the unit dosage form contains about 300 mg. In some embodiments, a unit dosage form according to the present invention is suitable for subcutaneous administration to a patient.

The present invention also includes methods of preparing a unit dosage form. In an exemplary embodiment, a method for preparing a pharmaceutical unit dosage form includes combining the formulation of any of foregoing embodiments in a suitable container (e.g., those containers discussed herein).

Therapeutic Uses of the Pharmaceutical Formulations

The pharmaceutical formulations of the present invention are useful, inter alia, for the treatment, prevention and/or amelioration of any disease or disorder associated with IL-33 activity. In particular, the pharmaceutical formulations of the invention are useful, inter alia, for the treatment, prevention and/or amelioration of any disease or disorder associated with or mediated by IL-33 expression, signaling, or activity, or treatable by blocking the interaction between IL-33 and a IL-33 ligand (e.g., ST2) or otherwise inhibiting IL-33 activity and/or signaling.

The therapeutic methods of the present invention comprise administering to a subject any formulation comprising an anti-hIL-33 antibody as disclosed herein. The subject to which the pharmaceutical formulation is administered can be, e.g., any human or non-human animal that is in need of such treatment, prevention and/or amelioration, or who would otherwise benefit from the inhibition or attenuation of IL-33 and/or IL-33-mediated activity. For example, the subject can be an individual that is diagnosed with, or who is deemed to be at risk of being afflicted by any of the aforementioned diseases or disorders. The present invention further includes the use of any of the pharmaceutical formulations disclosed herein in the manufacture of a medicament for the treatment, prevention and/or amelioration of any disease or disorder associated with IL-33 activity, including any of the above mentioned exemplary diseases, disorders and conditions.

In some embodiments, the present invention provides kits comprising a pharmaceutical formulation (e.g., a container with the formulation or a unit dosage form), as discussed herein, and packaging or labeling (e.g., a package insert) with instructions to use the pharmaceutical formulation for the treatment of a disease or disorder, as discussed above. In some cases, the instructions provide for use of a unit dosage form, as discussed herein, for the treatment of a disease or disorder.

The sequences discussed herein and shown in the accompanying sequence listing correspond to mAb1, a fully human antibody with an IgG4 heavy chain constant region, which is used throughout the following Examples. The identities of the sequences are shown below.

| Sequence Table (SEQ ID NOs) | | | | | | | | | |
|---|---|---|---|---|---|---|---|---|---|
| HCVR | | HCDR1 | | HCDR2 | | HCDR3 | | Heavy Chain | |
| DNA | Protein | DNA | Protein | DNA | Protein | DNA | Protein | DNA | Protein |
| 1 | 2 | 3 | 4 | 5 | 6 | 7 | 8 | 17 | 18 |
| LCVR | | LCDR1 | | LCDR2 | | LCDR3 | | Light Chain | |
| DNA | Protein | DNA | Protein | DNA | Protein | DNA | Protein | DNA | Protein |
| 9 | 10 | 11 | 12 | 13 | 14 | 15 | 16 | 19 | 20 |

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Effect of Buffer and pH on the Stability of an Anti-IL-33 Antibody

The effect of buffer and pH on the thermal stability of mAb1 was examined in liquid formulations by incubating 5 mg/mL mAb1 at 45° C. for 28 days in a series of buffer systems at varying pH ranges. The following pH and buffer systems were studied: acetate (pH 4.5 to 5.5), L-histidine (pH 5.5 to 6.5), and phosphate (pH 6.0 to 7.0). Based on results from SE-UPLC analysis, maximum protein stability was observed when mAb1 was formulated between pH 6.0 and pH 6.5 in L-histidine buffer. Based on results from CEX-UPLC analysis, maximum protein stability was observed when mAb1 was formulated between pH 5.0 and pH 6.0 in L-histidine or acetate buffer. These analyses also revealed that formation of HMW species and charge variants were the main degradation pathways. The results are shown in Table 1.

TABLE 1

Effect of Buffer and pH on the Stability of 5 mg/mL mAb1 Incubated at 45° C. for 28 Days Formulation
5 mg/mL mAb1, 20 mM buffer
Fill Volume
0.2 mL
Container/Closure
96-well CZ plate with C4 cover

| pH/Buffer | Turbidity (Increase in OD at 405 nm) | % Total Protein Recovered by SE-UPLC[a] | Change in Purity by SE-UPLC[b] | | | Change in Charged Variants by CEX-UPLC[b] | | |
|---|---|---|---|---|---|---|---|---|
| | | | % HMW | % Native | % LMW | % Acidic | % Main | % Basic |
| pH 4.5, Acetate | 0.00 | 104 | 1.2 | −2.2 | 1.0 | 16.3 | −20.9 | 4.6 |
| pH 5.0, Acetate | 0.00 | 103 | 2.3 | −2.7 | 0.4 | 17.7 | −19.9 | 2.2 |
| pH 5.5, Acetate | 0.00 | 103 | 1.7 | −1.9 | 0.2 | 20.2 | −21.1 | 0.8 |
| pH 5.5, L-Histidine | 0.00 | 103 | 2.0 | −2.6 | 0.6 | 18.7 | −20.3 | 2.8 |
| pH 6.0, L-Histidine | 0.00 | 104 | 1.2 | −1.4 | 0.2 | 21.1 | −22.3 | 1.3 |
| pH 6.5, L-Histidine | 0.00 | 103 | 1.2 | −1.3 | 0.1 | 26.8 | −22.1 | −4.7 |
| pH 6.0, Phosphate | 0.00 | 104 | 3.3 | −3.5 | 0.2 | 25.1 | −20.9 | −4.3 |
| pH 6.5, Phosphate | 0.01 | 101 | 3.6 | −3.8 | 0.2 | 32.6 | −32.2 | −0.4 |
| pH 7.0, Phosphate | 0.11 | 101 | 2.6 | −3.0 | 0.5 | 45.2 | −42.2 | −3.0 |

[a]The % total protein recovery was defined as: total peak area determined from SE-UPLC at Day 28/total peak area determined by SE-UPLC at Day 0 * 100%.
[b]Reported as a change in purity relative to the starting material. The starting material (no incubation) contains ≥97.2% native peak by SE-UPLC and ≥56.5% main peak by CEX-UPLC in all formulations.

The effect of pH and buffer on the thermal stability of mAb1 was examined in liquid formulations by incubating 150 mg/mL mAb1 at 37° C. for 28 days in a series of L-histidine and acetate buffers ranged at pH 4.5, 5.0 and 6.0 in the presence of 5% sucrose as a thermal stabilizer. Based on results from SE-UPLC analysis for molecular weight species and CEX-UPLC analysis for charge variants, aggregation (i.e., formation of HMW species), and formation of charge variants were the main degradation pathways. mAb1 stability in pH 5.0 and 6.0 in L-histidine buffer and pH 5.0 in acetate buffer is comparable, as shown in Table 2.

TABLE 2

Effect of pH and buffer on the Stability of 150 mg/mL mAb1 Incubated at 37° C. for 28 Days Formulation
150 mg/mL mAb1, 10 mM L-histidine or 10 mM acetate, 5% sucrose
Fill Volume
0.3 mL
Container/Closure
2 mL Type 1 borosilicate glass vial with a FluroTec ® coated 4432/50 butyl rubber stopper

| pH/Buffer | % Total Protein Recovered by SE-UPLC[a] | Change in Purity by SE-UPLC[b] | | | Change in Charged Variants by CEX-UPLC[b] | | |
|---|---|---|---|---|---|---|---|
| | | % HMW | % Native | % LMW | % Acidic | % Main | % Basic |
| pH 6.0 L-histidine | 100 | 1.4 | −1.8 | 0.4 | 7.8 | −8.2 | 0.4 |
| pH 5.0 L-histidine | 97 | 1.5 | −2.0 | 0.5 | 5.3 | −8.0 | 2.7 |
| pH 5.0 Acetate | 100 | 1.6 | −2.1 | 0.5 | 6.0 | −8.7 | 2.7 |

TABLE 2-continued

Effect of pH and buffer on the Stability of 150 mg/mL mAb1 Incubated at 37° C. for 28 Days Formulation
150 mg/mL mAb1, 10 mM L-histidine or 10 mM acetate, 5% sucrose
Fill Volume
0.3 mL
Container/Closure
2 mL Type 1 borosilicate glass vial with a FluroTec ® coated 4432/50 butyl rubber stopper

| pH/Buffer | % Total Protein Recovered by SE-UPLC[a] | Change in Purity by SE-UPLC[b] | | | Change in Charged Variants by CEX-UPLC[b] | | |
|---|---|---|---|---|---|---|---|
| | | % HMW | % Native | % LMW | % Acidic | % Main | % Basic |
| pH 4.5 Acetate | 95 | 4.3 | −5.8 | 1.5 | 8.4 | −12.5 | 4.0 |

[a]The % total protein recovery was defined as: total peak area determined from SE-UPLC at Day 28/total peak area determined by SE-UPLC at Day 0 * 100%.
[b]Reported as a change in purity relative to the starting material. The starting material (no incubation) contains ≥89.1% native peak by SE-UPLC and ≥64.8% main peak by CEX-UPLC in all formulations.

Example 2: Effect of Surfactants and Thermal Stabilizers on the Stability of an Anti-IL-33 Antibody The effects of two surfactants, 0.1% polysorbate 20 and 0.1% polysorbate 80, on the thermal stability of 5 mg/mL mAb1 were first examined in liquid formulations using a research lot of material. The results of the thermal stability study are summarized in Table 3. When incubated at 45° C., the addition of either polysorbate 20 or polysorbate 80 adversely impacted the thermal stability of mAb1 relative to a control formulation lacking any surfactant. Increases in high molecular weight species and charge variants were observed. The addition of 0.1% polysorbate 80 caused less of a relative increase in HMW species and formation of charge variant forms, compared to the addition of 0.1% polysorbate 20.

An additional study was conducted to investigate the polysorbate 80 concentration using a representative research lot of material at a mAb1 concentration of 50 mg/mL. The polysorbate 80 concentrations included in the study were 0%, 0.01%, 0.02%, 0.04%, 0.06%, 0.08%, and 0.1%. The results are summarized in Table 4 and 5. When agitated for 60 minutes, a 0.8% increase in the relative percentage of HMW was observed for the sample containing no polysorbate 80 (Table 4). Inspection of the SE-UPLC chromatograms showed that this increase was due to the formation of a higher order aggregate peak which was not present in the starting material. The addition of 0.02% polysorbate 80 prevented formation of this aggregate species following agitation for 60 minutes. When incubated at 45° C. for 28 days, the thermal stability of mAb1 was not affected by the polysorbate concentrations studied (Table 5).

5 mg/mL mAb1 in a liquid formulation exhibited improved stability when formulated with 5% sucrose and incubated under accelerated conditions, as shown in Table 3. After incubation at 45° C. for 28 days, the relative amount of HMW species increased by 0.7% in the formulation containing 5% sucrose compared to a 1.2% increase in the control formulation without sucrose.

TABLE 3

Effect of Surfactants on the Stability of 5 mg/mL mAb1 Incubated at 45° C. for 28 Days Formulation
5 mg/mL mAb1, 20 mM L-histidine pH 6.0
Fill Volume
0.2 mL
Container/Closure
96-well CZ plate with C4 cover

| Co-Solvent/ Surfactant | Turbidity (Increase in OD at 405 nm) | pH | % Total Protein Recovered by SE-UPLC | Change in Purity by SE-UPLC[a] | | | Change in Charge Variants by CEX-UPLC[ab] | | |
|---|---|---|---|---|---|---|---|---|---|
| | | | | % HMW | % Native | % LMW | % Acidic | % Main | % Basic |
| No co-solvent/ surfactant | 0.00 | 6.0 | 104 | 1.2 | −1.4 | 0.2 | 2.6 | −3.9 | 1.4 |
| 5% (w/v) Sucrose, no co-solvent/ surfactant | 0.00 | 6.0 | 110 | 0.7 | −0.9 | 0.1 | 3.8 | −5.4 | 1.6 |

TABLE 3-continued

Effect of Surfactants on the Stability of 5 mg/mL mAb1 Incubated at 45° C. for 28 Days Formulation
5 mg/mL mAb1, 20 mM L-histidine pH 6.0
Fill Volume
0.2 mL
Container/Closure
96-well CZ plate with C4 cover

| Co-Solvent/ Surfactant | Turbidity (Increase in OD at 405 nm) | pH | % Total Protein Recovered by SE-UPLC | Change in Purity by SE-UPLC[a] | | | Change in Charge Variants by CEX-UPLC[ab] | | |
|---|---|---|---|---|---|---|---|---|---|
| | | | | % HMW | % Native | % LMW | % Acidic | % Main | % Basic |
| 5% (w/v) Sucrose, 0.1% (w/v) polysorbate 20 | 0.01 | 5.9 | 107 | 16.6 | −16.7 | 0.2 | 1.9 | −25.0 | 23.0 |
| 5% (w/v) Sucrose, 0.1% (w/v) polysorbate 80 | 0.01 | 5.9 | 109 | 11.5 | −11.9 | 0.4 | 5.6 | −11.8 | 6.2 |

[a]Reported as a change in purity relative to the starting material. The staring material (no incubation) contains ≥97.2% native peak by SE-UPLC and ≥57.6 main peak by CEX-UPLC in all four formulations.

[b]Data was analyzed at the Day 14 time point in this study because the CEX chromatograms for formulations containing polysorbate 20 and polysorbate 80 could not be integrated at the Day 28 time point due to severe degradation of each sample.

TABLE 4

Effect of Polysorbate 80 Concentration on the Stability of 50 mg/mL mAb1 Following Agitation (120 minutes of vortexing)

Formulation
50 mg/mL mAb1, 10 mM L-histidine, pH 6.0, 5% (w/v) sucrose
Fill Volume
0.4 mL
Container/Closure
2 mL Type 1 borosilicate glass vial with a FluorTec ®-coated 4432/50 butyl rubber stopper

| Polysorbate 80 | Color and Appearance | Turbidity (Increase in OD at 405 nm) | pH | % Total Protein Recovered by RP-UPLC | Change in Purity by SE-UPLC[a] | | | Change in Charge Variants by CEX-UPLC[a] | | |
|---|---|---|---|---|---|---|---|---|---|---|
| | | | | | % HMW | % Native | % LMW | % Acidic | % Main | % Basic |
| No polysorbate 80 | Pass | 0.01 | 6.0 | 96 | 0.8 | −0.8 | 0.0 | −0.2 | 0.7 | −0.5 |
| 0.02% (w/v) | Pass | 0.00 | 6.1 | 97 | 0.0 | 0.0 | 0.0 | −0.8 | 0.8 | 0.0 |
| 0.04% (w/v) | Pass | 0.01 | 6.0 | 102 | 0.0 | 0.0 | 0.0 | 0.7 | −0.5 | −0.1 |
| 0.06% (w/v) | Pass | 0.01 | 6.1 | 99 | 0.0 | 0.0 | 0.0 | −0.2 | 0.2 | 0.1 |
| 0.08% (w/v) | Pass | 0.00 | 6.0 | 95 | 0.0 | 0.0 | 0.0 | 0.0 | 0.0 | 0.0 |
| 0.1% (w/v) | Pass | 0.00 | 6.0 | 99 | 0.0 | 0.0 | 0.0 | 0.0 | 0.2 | −0.1 |

[a]Reported as a change in purity relative to the starting material. The starting material (no incubation) contains 97.9% native peak by SE-UPLC and ≥68.7% main peak by CEX-UPLC in all six formulations.

TABLE 5

Effect of Polysorbate 80 Concentration on the Stability of 50 mg/mL mAb1 Incubated at 45° C. for 28 Days Formulation
50 mg/mL mAb1, 10 mM L-histidine, pH 6.0, 5% (w/v) sucrose
Fill Volume
0.4 mL
Container/Closure
2 mL Type 1 borosilicate glass vial with a FluorTec ®-coated 4432/50 butyl rubber stopper

| Polysorbate 80 | Color and Appearance | Turbidity (Increase in OD at 405 nm) | pH | % Total Protein Recovered by RP-UPLC | Change in Purity by SE-UPLC[a] | | | Change in Charge Variants by CEX-UPLC[a] | | |
|---|---|---|---|---|---|---|---|---|---|---|
| | | | | | % HMW | % Native | % LMW | % Acidic | % Main | % Basic |
| No PS-80 | Pass | 0.01 | 6.1 | 96 | 3.4 | −4.9 | 1.5 | 31.7 | −32.3 | 0.6 |
| 0.02% (w/v) | Pass | 0.01 | 6.1 | 96 | 3.5 | −5.0 | 1.5 | 31.1 | −31.6 | 0.5 |
| 0.04% (w/v) | Pass | 0.01 | 6.1 | 101 | 3.5 | −5.0 | 1.5 | 32.4 | −32.9 | 0.5 |
| 0.06% (w/v) | Pass | 0.01 | 6.1 | 99 | 3.4 | −5.1 | 1.6 | 31.6 | −32.3 | 0.8 |
| 0.08% (w/v) | Pass | 0.01 | 6.1 | 96 | 3.4 | −5.0 | 1.7 | 30.1 | −31.2 | 1.0 |
| 0.1% (w/v) | Pass | 0.01 | 6.1 | 98 | 3.6 | −5.2 | 1.6 | 30.4 | −31.0 | 0.6 |

[a]Reported as a change in purity relative to the starting material. The starting material (no incubation) contains 97.9% native peak by SE-UPLC and ≥68.7% main peak by CEX-UPLC in all six formulations.

Example 3: Effect of Viscosity Modifiers on the Stability of an Anti-IL-33 Antibody mAb1 may be contained in a prefilled syringe (PFS), and delivered through a delivery device, such as an autoinjector. Viscosity correlates with the ease of injection through a prefilled syringe (PFS). Maintaining a reasonably low viscosity is advantageous for the development of a delivery device, such as autoinjector.

Figure 2:
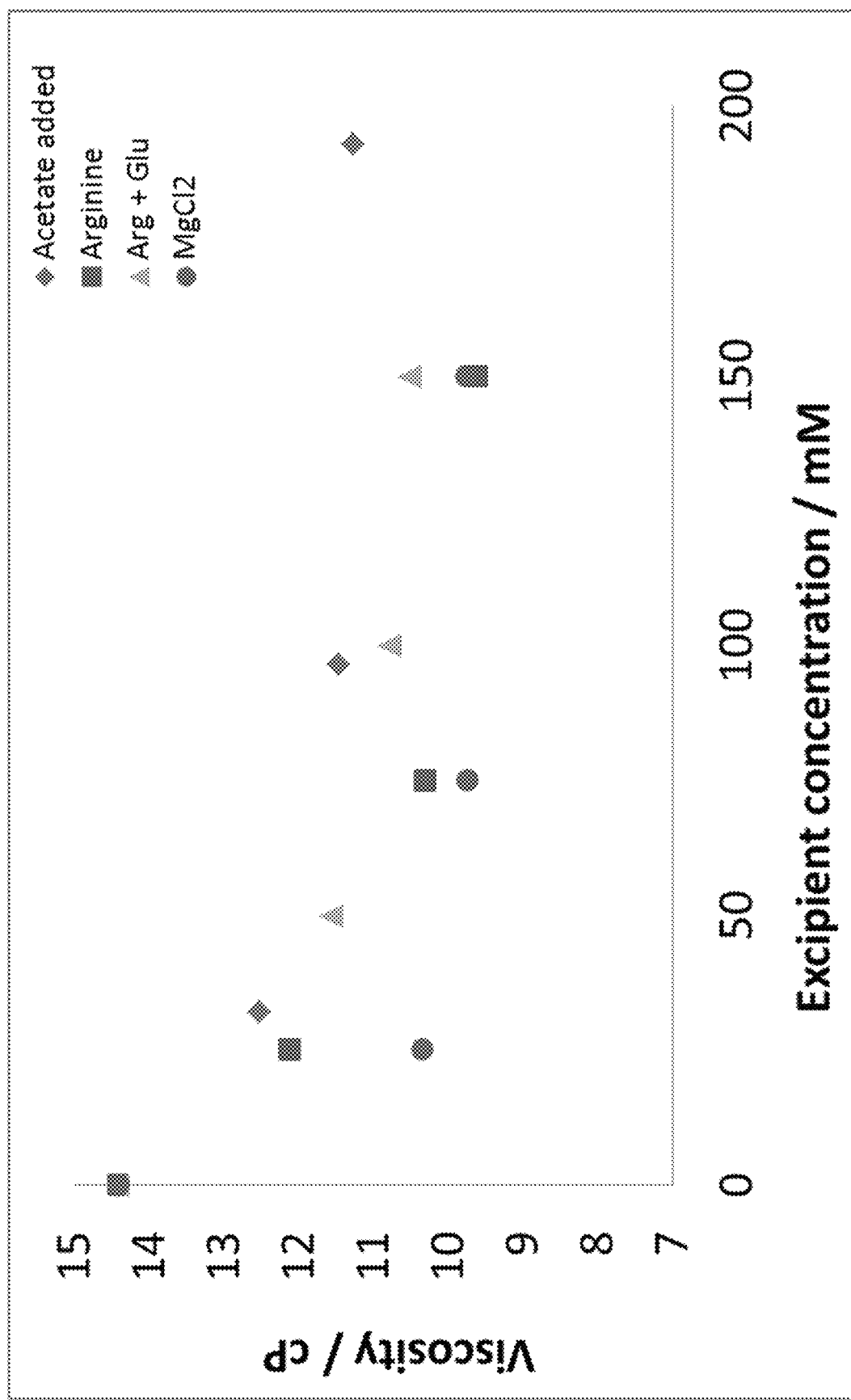
FIG. 2 shows the viscosity of 150 mg/mL of an anti-IL-33 antibody (mAb1) with different concentrations of viscosity modifiers.

The effect of pH on the viscosity of 150 mg/mL mAb1 in 10 mM L-histidine buffer was examined. As shown in FIG. 1, mAb1 viscosity is highly dependent on pH at the pH range of 4.8 to 6.7. The lower the pH, the lower the mAb1 viscosity. The effect of excipients on formulation viscosity was also examined in mAb1 liquid formulation with the following potential viscosity modifiers, sodium acetate, L-arginine hydrochloride, sodium L-glutamate, and magnesium chloride up to 200 mM. The base formulation contained 150 mg/mL mAb1, 27 mM acetate, and 5% sucrose at pH 5.3. The results are shown in FIG. 2. All of these excipients at 25-150 mM reduced the viscosity of 150 mg/mL mAb1 by 2-5 cP at pH 5.3.

Figure 3:
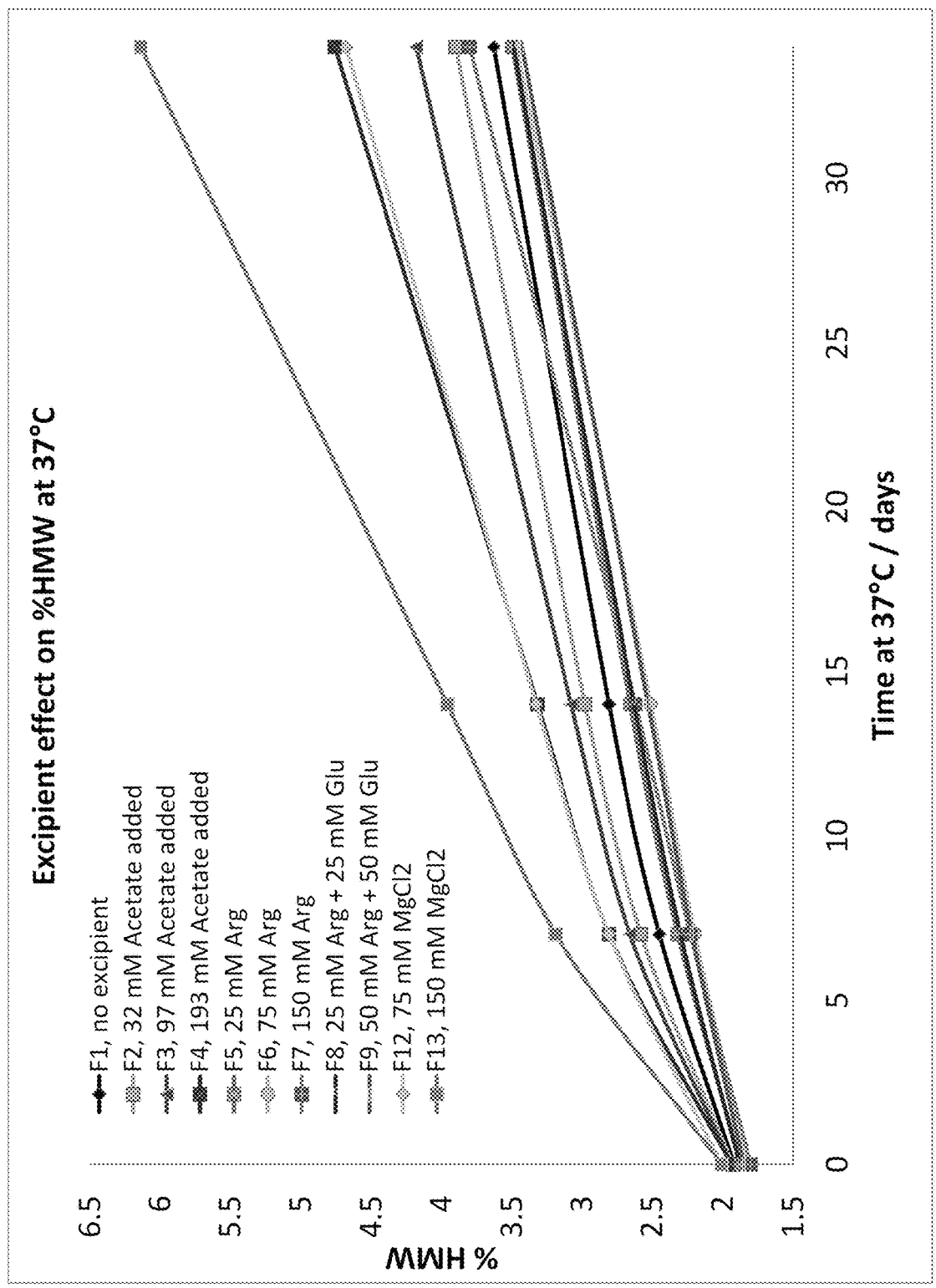
FIG. 3 shows the effect of various viscosity modifiers on the stability of an anti-IL-33 antibody (mAb1) incubated at 37° C. for 34 days. For clarity, the points at the far right side of FIG. 3 are ordered, from top to bottom: F13, F4, F12, F3, F2, F7, F1, F5, F8, F6 and F9.

The effect of the viscosity modifiers on the stability of 150 mg/mL mAb1 was also examined by incubating the formulations at 37° C. for 34 days. Formation of HMW species was the major degradation pathway, and the results are illustrated in FIG. 3. Compared with the control formulation, which did not contain any viscosity modifier, the addition of magnisum chloride or sodium acetate promoted the formation of HMW after 37° C. incubation. On the other hand, L-arginine hydrochloride and sodium L-glutamate did not adversely impact mAb1 stability. Instead, 75 mM L-arginine hydrochloride improved the mAb1 stability against HMW formation.

Based on the viscosity reducing effect and the impact on the thermal stability, L-arginine hydrochloride was selected as the viscosity modifier for mAb1 formulations.

Example 4: Impact of Formulation Parameters on Viscosity and Stability

A custom experimental design was applied to understand the effect of each formulation component, as well as pH, and the interaction of the parameters on the stability and viscosity of mAb1. Formulation parameters in this study include protein concentration (135-165 mg/mL), sucrose concentration (5-9%), L-arginine hydrochloride concentration (0-75 mM), and pH. Surfactant remains constant at 0.1% for all the formulations in this study.

The viscosity of the formulations remained unchanged before and after 28 days incubation at 40° C./75% RH.

Figure 4A:
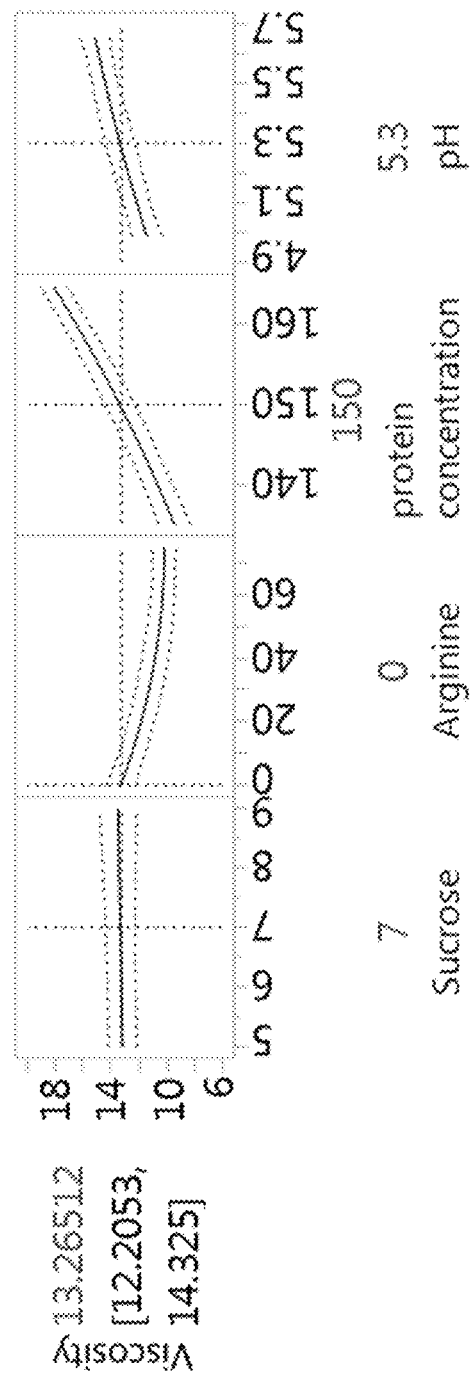
FIG. 4A illustrates the impact of the formulation parameters on the viscosity of an anti-IL-33 antibody (mAb1).

The viscosity against main formulation parameters was analyzed by fit model using JMP 12 with standard least squares personality and effect leverage emphasis. The major factors impacting the formulation viscosity are the mAb1 concentration, pH and L-arginine hydrochloride concentration, as illustrated in FIG. 4A.

The stability of the formulations after 28 days incubation at 40° C./75% RH was also investigated. No meaningful difference was observed for 14 formulations after 40° C./75% RH incubation for 28 days in color and appearance, turbidity, change in pH, protein recovery or change in charge variants. The major stability indicating attribute was the formation of HMW species.

Figure 4B:
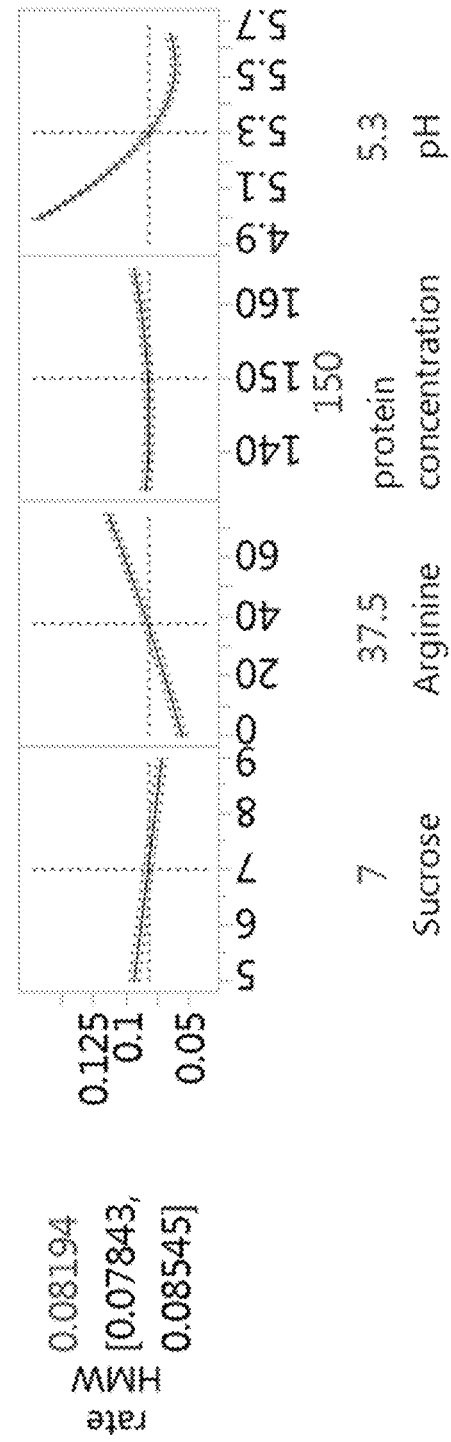
FIG. 4B illustrates the impact of the formulation parameters on the formation of high-molecular weight (HMW) variants of an anti-IL-33 antibody (mAb1).

The rate of HMW formation against main formulation parameters was analyzed by fit model using JMP 12 with standard least squares personality and effect leverage emphasis. The major factors impacting the HMW formation were the pH, L-arginine hydrochloride concentration, and sucrose concentration, as illustrated in FIG. 4B.

Selection of the formulation composition was based on minimizing formulation viscosity and the rate of HMW formation using JMP12 desirability function. The multiparametric analyses were used to produce a composition containing 5% sucrose, and 70 mM L-arginine hydrochloride at pH 5.3 with an antibody (mAb1) concentration of 150 mg/ml. This formulation minimized the formulation viscosity as well as HMW formation. Meanwhile it reduced the sensitivity of viscosity and stability variation to the excipient composition variation.

Example 5: Effect of Surfactant Concentration on Stability of Anti-IL-33 Antibody Polysorbate 80 was identified as a stabilizing surfactant in the studies discussed in Example 2, above. The base formulation for this study was 150 mg/mL mAb1, 10 mM acetate buffer, 5% (w/v) sucrose, and 70 mM L-arginine hydrochloride. The polysorbate 80 concentrations in the initial evaluation were 0.01%, 0.02%, 0.04%, 0.05%, 0.06%, 0.08%, and 0.1%. The results are summarized in Table 6. After 48 hours of orbital shaking at 250 rpm, increases in the relative percentage of HMW were observed for the sample containing lower levels of polysorbate 80. The addition of 0.055% polysorbate 80 prevented formation of this aggregate species following 48 hours of orbital shaking.

TABLE 6

Effect of Polysorbate 80 Concentration on the Stability of 150 mg/mL mAb1 Following 48 h of orbital shaking

| Formulation | 150 mg/mL mAb1, 10 mM acetate buffer, 5% (w/v) sucrose, 70 mM L-arginine hydrochloride |
|---|---|
| Fill Volume | 2.5 mL |
| Container/Closure | 5 mL Type 1 borosilicate glass vial with a FluorTec ®-coated 4432/50 butyl rubber stopper |

| Color and Appearance | % Total Protein Recovered by SEC-UPLC | % Polysorbate 80 Measured by CAD | Change in Purity by SE-UPLC[a] | | |
|---|---|---|---|---|---|
| | | | % HMW | % Native | % LMW |
| Pass | 100 | 0.021 | 23.5 | −23.5 | 0.0 |
| Pass | 100 | 0.033 | 4.1 | −4.1 | 0.0 |
| Pass | 99 | 0.055 | 0.1 | −0.1 | 0.0 |
| Pass | 100 | 0.063 | 0.0 | 0.0 | 0.0 |
| Pass | 99 | 0.070 | 0.0 | 0.0 | 0.0 |
| Pass | 99 | 0.087 | 0.0 | 0.0 | 0.0 |
| Pass | 99 | 0.102 | 0.0 | 0.0 | 0.0 |

[a]Reported as a change in purity relative to the starting material. The starting material (no incubation) contains 98.6% native peak by SE-UPLC.

The acceptable range of polysorbate 80 in the 150 mg/mL mAb1 formulation was further examined by studying the agitation stability as well as thermal stability. With the same base formulation, the polysorbate 80 concentrations in this ranging study were 0.02%, 0.05%, 0.08%, and 0.12%. The formulations were subjected to 48 hours of orbital shaking at 250 rpm and thermal stress at 40° C./75% RH for one month. The results of the orbital shaking confirmed ≥0.05% polysorbate 80 prevented formation of this aggregate species following 48 hours of orbital shaking (see Table 7). The thermal stability of mAb1 was not affected by the polysorbate concentrations studied (see Table 7). These results indicated that 0.05-0.12% of polysorbate 80 provided sufficient stabilization to prevent formation of aggregates under agitation stress without adversely impacting the formulation stability. A target concentration of 0.08% of polysorbate 80 was selected for the 150 mg/mL mAb1 formulation based on these results.

TABLE 7

Effect of Polysorbate 80 Concentration on the Stability of 150 mg/mL mAb1 Following 48 h of orbital shaking Formulation
150 mg/mL mAb1, 10 mM acetate buffer, 5% (w/v) sucrose,
70 mM L-arginine hydrochloride
Fill Volume
2.5 mL
Container/Closure
5 mL Type 1 borosilicate glass vial with a FluorTec ®-coated
4432/50 butyl rubber stopper

| Polysorbate 80 | Color and Appearance | Turbidity (Increase in OD at 405 nm) | pH | % Total Protein Recovered by SEC-UPLC | Change in Purity by SE-UPLC[a] | | |
|---|---|---|---|---|---|---|---|
| | | | | | % HMW | % Native | % LMW |
| Stress: 48 h of orbital shaking at 250 rpm | | | | | | | |
| 0.02% (w/v) | Pass | 0.01 | 5.4 | 100 | 6.4 | −6.4 | 0.0 |
| 0.05% (w/v) | Pass | 0.00 | 5.4 | 100 | 0.1 | −0.1 | 0.0 |

TABLE 7-continued

Effect of Polysorbate 80 Concentration on the Stability of 150 mg/mL
mAb1 Following 48 h of orbital shaking Formulation
150 mg/mL mAb1, 10 mM acetate buffer, 5% (w/v) sucrose,
70 mM L-arginine hydrochloride
Fill Volume
2.5 mL
Container/Closure
5 mL Type 1 borosilicate glass vial with a FluorTec ®-coated
4432/50 butyl rubber stopper

| Polysorbate 80 | Color and Appearance | Turbidity (Increase in OD at 405 nm) | pH | % Total Protein Recovered by SEC-UPLC | Change in Purity by SE-UPLC[a] | | |
|---|---|---|---|---|---|---|---|
| | | | | | % HMW | % Native | % LMW |
| 0.08% (w/v) | Pass | 0.00 | 5.4 | 100 | 0.0 | −0.1 | 0.1 |
| 0.12% (w/v) | Pass | 0.00 | 5.4 | 99 | 0.0 | 0.0 | 0.1 |
| Stress: 40° C./75% RH for one month | | | | | | | |
| 0.02% (w/v) | Pass | 0.01 | 5.4 | 99 | 2.9 | −3.5 | 0.6 |
| 0.05% (w/v) | Pass | 0.00 | 5.4 | 98 | 3.0 | −3.7 | 0.7 |
| 0.08% (w/v) | Pass | 0.01 | 5.4 | 98 | 2.9 | −3.6 | 0.7 |
| 0.12% (w/v) | Pass | 0.01 | 5.4 | 99 | 3.0 | −3.6 | 0.7 |

[a]Reported as a change in purity relative to the starting material. The starting material (no incubation) contains 97.7% native peak by SE-UPLC.

Example 6: Stability of Liquid Formulated Anti-IL-33 Antibody Drug Substance An ongoing long-term storage stability study is being conducted to evaluate stability through 36 months of storage at −80° C., −30° C., and −20° C. for formulations of mAb1. A composition containing 150 mg/ml of mAb1 was physically and chemically stable when stored at −80° C., −30° C., and −20° C. for 24 months, as shown in Tables 9 to 10. No appreciable change in the physical or chemical stability was detected in any of the monitored attributes. Further, a composition containing 150 mg/ml of mAb1 has been shown to be stable when stored at −80° C., −30° C., and −20° C. for at least 9 months (see Tables 11 to 13). Finally, a composition containing 15 mg/ml of mAb1 has been shown to be stable when stored at −80° C., −30° C., and −20° C. for at least 9 months (see Tables 16 to 18). All of the results collected to date are shown in Tables 8 to 20, below.

TABLE 8

Research Stability of 150 mg/mL mAb1 Formulated Drug
Substance Stored at −80° C.

Formulation
150 mg/mL mAb1, 27 mM acetate, 5% (w/v) sucrose, 70 mM
L-arginine hydrochloride, 0.1% (w/v) polysorbate 80, pH 5.3
Fill Volume
0.6 mL
Container/Closure
5 mL polycarbonate vial with silicone lined polypropylene screw cap Length of Storage at −80° C. (months)

| Assay | | 0 | 1 | 3 | 6 | 9 | 12 | 18 | 24 | 36 |
|---|---|---|---|---|---|---|---|---|---|---|
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 | 0.00 | 0.00 |
| pH | | 5.2 | 5.2 | 5.2 | 5.2 | 5.3 | 5.3 | 5.2 | 5.2 | 5.3 |
| % Protein recovered by SEC-UPLC | | 100 | 102 | 103 | 102 | 104 | 105 | 105 | 103 | 101 |
| Purity by SE-UPLC | % HMW | 1.5 | 1.5 | 1.5 | 1.5 | 1.5 | 1.5 | 1.5 | 1.5 | 1.5 |
| | % Native | 98.0 | 98.1 | 98.0 | 98.0 | 97.9 | 98.1 | 98.0 | 98.0 | 98.1 |
| | % LMW | 0.5 | 0.5 | 0.5 | 0.5 | 0.6 | 0.4 | 0.5 | 0.5 | 0.4 |
| Charge variant analysis by CEX-UPLC | % Acidic | 29.4 | 29.7 | 29.4 | 29.4 | 29.8 | 29.7 | 29.5 | 30.0 | 29.3 |
| | % Main | 66.1 | 65.6 | 65.8 | 65.8 | 65.6 | 65.7 | 64.6 | 65.1 | 65.9 |
| | % Basic | 4.5 | 4.7 | 4.8 | 4.8 | 4.7 | 4.6 | 5.9 | 4.9 | 4.8 |

TABLE 9

Research Stability of 150 mg/mL mAb1 Formulated Drug Substance Stored at −30° C.

Formulation
150 mg/mL mAb1, 27 mM acetate, 5% (w/v) sucrose, 70 mM L-arginine hydrochloride, 0.1% (w/v) polysorbate 80, pH 5.3
Fill Volume
0.6 mL
Container/Closure
5 mL polycarbonate vial with silicone lined polypropylene screw cap

| Assay | | 0 | 1 | 3 | 6 | 9 | 12 | 18 | 24 | 36 |
|---|---|---|---|---|---|---|---|---|---|---|
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 | 0.00 | 0.00 |
| pH | | 5.2 | 5.2 | 5.2 | 5.2 | 5.3 | 5.3 | 5.2 | 5.3 | 5.3 |
| % Protein recovered by SEC-UPLC | | 100 | 103 | 104 | 104 | 103 | 106 | 107 | 104 | 104 |
| Purity by SE-UPLC | % HMW | 1.5 | 1.5 | 1.5 | 1.5 | 1.5 | 1.5 | 1.5 | 1.6 | 1.6 |
| | % Native | 98.0 | 98.1 | 98.0 | 98.0 | 97.9 | 98.1 | 98.0 | 98.0 | 98.0 |
| | % LMW | 0.5 | 0.5 | 0.5 | 0.5 | 0.5 | 0.4 | 0.5 | 0.5 | 0.4 |
| Charge variant analysis by CEX-UPLC | % Acidic | 29.4 | 29.6 | 29.5 | 29.4 | 29.7 | 29.8 | 29.5 | 29.6 | 29.5 |
| | % Main | 66.1 | 65.8 | 65.8 | 65.8 | 65.6 | 65.6 | 64.7 | 65.6 | 65.7 |
| | % Basic | 4.5 | 4.7 | 4.7 | 4.8 | 4.7 | 4.6 | 5.9 | 4.9 | 4.8 |

TABLE 10

Research Stability of 150 mg/mL mAb1 Formulated Drug Substance Stored at −20° C.

Formulation
150 mg/mL mAb1, 27 mM acetate, 5% (w/v) sucrose, 70 mM L-arginine hydrochloride, 0.1% (w/v) polysorbate 80, pH 5.3
Fill Volume
0.6 mL
Container/Closure
5 mL polycarbonate vial with silicone lined polypropylene screw cap

| Assay | | 0 | 1 | 3 | 6 | 9 | 12 | 18 | 24 | 36 |
|---|---|---|---|---|---|---|---|---|---|---|
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 | 0.01 | 0.00 |
| pH | | 5.2 | 5.2 | 5.3 | 5.2 | 5.3 | 5.3 | 5.2 | 5.2 | 5.3 |
| % Protein recovered by SEC-UPLC | | 100 | 103 | 104 | 105 | 107 | 108 | 110 | 108 | 107 |
| Purity by SE-UPLC | % HMW | 1.5 | 1.5 | 1.5 | 1.5 | 1.5 | 1.5 | 1.5 | 1.5 | 1.6 |
| | % Native | 98.0 | 98.1 | 98.0 | 98.0 | 97.9 | 98.1 | 98.0 | 98.0 | 98.0 |
| | % LMW | 0.5 | 0.5 | 0.5 | 0.5 | 0.6 | 0.4 | 0.5 | 0.5 | 0.4 |
| Charge variant analysis by CEX-UPLC | % Acidic | 29.4 | 29.5 | 29.5 | 29.7 | 29.8 | 29.4 | 29.3 | 29.8 | 29.7 |
| | % Main | 66.1 | 65.8 | 65.7 | 65.6 | 65.5 | 65.9 | 64.7 | 65.3 | 65.6 |
| | % Basic | 4.5 | 4.7 | 4.7 | 4.7 | 4.7 | 4.7 | 6.0 | 4.9 | 4.8 |

TABLE 11

Research Stability of 150 mg/mL mAb1 Formulated Drug Substance Stored at −80° C.

Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap

| Assay | 0 | 1 | 3 | 6 | 9 | 12 | 18 | 24 | 36 |
|---|---|---|---|---|---|---|---|---|---|
| Color and appearance | Pass | Pass | Pass | Pass | Pass | Pass | Pass | | |
| Turbidity (Increase in OD at 405 nm) | 0.00 | 0.00 | 0.00 | 0.00 | 0.00 | 0.01 | 0.00 | | |

TABLE 11-continued

Research Stability of 150 mg/mL mAb1 Formulated Drug Substance Stored at −80° C.

Formulation
150 mg/mL mAb1, 10 mM acetate, 5% (w/v) sucrose, 70 mM
L-arginine hydrochloride, 0.08% (w/v) polysorbate 80, pH 5.3
Fill Volume
2.0 mL
Container/Closure
5 mL polycarbonate vial with silicone lined polypropylene screw cap
Length of Storage at −80° C. (months)

| | Assay | 0 | 1 | 3 | 6 | 9 | 12 | 18 | 24 | 36 |
|---|---|---|---|---|---|---|---|---|---|---|
| | pH | 5.3 | 5.2 | 5.2 | 5.2 | 5.3 | 5.2 | 5.3 | | |
| | % Protein recovered by SEC-UPLC | 100 | 108 | 105 | 100 | 98 | 105 | 100 | | |
| Purity by Non-reduced MCE | % Main Peak Purity | 97.4 | NR | 96.1 | 96.0 | NR | 97.2 | NR | | |
| | % LMW Species | 2.5 | NR | 3.8 | 3.9 | NR | 2.7 | NR | | |
| | % HMW Species | 0.1 | NR | 0.1 | 0.1 | NR | 0.1 | NR | | |
| Purity by reduced MCE | % Purity | 94.2 | NR | 94.8 | 94.8 | NR | 94.2 | NR | | |
| | % LMW Species | 2.2 | NR | 1.7 | 2.1 | NR | 2.4 | NR | | |
| | % NGHC | 1.7 | NR | 1.8 | 1.6 | NR | 1.7 | NR | | |
| Purity by SE-UPLC | % HMW | 0.5 | 0.5 | 0.5 | 0.5 | 0.5 | 0.5 | 0.5 | | |
| | % Native | 99.2 | 99.2 | 99.3 | 99.3 | 99.3 | 99.3 | 99.3 | | |
| | % LMW | 0.4 | 0.4 | 0.3 | 0.2 | 0.2 | 0.3 | 0.2 | | |
| Charge variant analysis by CEX-UPLC | % Acidic | 19.1 | 19.0 | 21.4 | 20.0 | 19.6 | 19.7 | 17.6 | | |
| | % Main | 66.8 | 66.6 | 66.0 | 67.8 | 67.8 | 67.1 | 70.1 | | |
| | % Basic | 14.1 | 14.4 | 12.6 | 12.2 | 12.6 | 13.2 | 12.3 | | |
| Charge variant analysis by iCIEF | % Acidic | 31.3 | NR | 31.2 | 32.2 | NR | 30.4 | NR | | |
| | % Main | 56.3 | NR | 56.0 | 55.8 | NR | 57.1 | NR | | |
| | % Basic | 12.4 | NR | 12.9 | 12.1 | NR | 12.6 | NR | | |
| | % Relative potency (bioassay) | 116 | NR | NR | NR | NR | 101 | NR | | |

CEX = Cation exchange;
DS = Drug substance;
HMW = High molecular weight;
iCIEF = Imaging capillary isoelectric focusing;
LMW = Low molecular weight;
MCE-SDS = Microchip capillary electrophoresis-sodium dodecyl sulfate;
NR = Not required;
OD = Optical density;
RP = Reverse phase;
SE = Size exclusion;
UPLC = Ultra-performance liquid chromatography

TABLE 12

Research Stability of 150 mg/mL mAb1 Formulated Drug Substance Stored at −30° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.0 mL
Container/Closure
5 mL polycarbonate vial with silicone lined polypropylene screw cap
Length of Storage at −30° C. (months)

| | Assay | 0 | 1 | 3 | 6 | 9 | 12 | 18 | 24 | 36 |
|---|---|---|---|---|---|---|---|---|---|---|
| | Color and appearance | Pass | Pass | Pass | Pass | Pass | Pass | Pass | | |
| | Turbidity (Increase in OD at 405 nm) | 0.00 | 0.00 | 0.00 | 0.00 | 0.00 | 0.01 | 0.00 | | |
| | pH | 5.3 | 5.2 | 5.2 | 5.2 | 5.3 | 5.2 | 5.3 | | |
| | % Protein recovered by SEC-UPLC | 100 | 108 | 107 | 101 | 99 | 106 | 99 | | |
| Purity by Non-reduced MCE | % Main Peak Purity | 97.4 | NR | 96.0 | 95.9 | NR | 97.2 | NR | | |
| | % LMW Species | 2.5 | NR | 4.0 | 4.0 | NR | 2.7 | NR | | |
| | % HMW Species | 0.1 | NR | 0.1 | 0.1 | NR | 0.1 | NR | | |
| Purity by reduced MCE | % Purity | 94.2 | NR | 94.3 | 94.6 | NR | 94.1 | NR | | |
| | % LMW Species | 2.2 | NR | 2.1 | 1.9 | NR | 2.6 | NR | | |
| | % NGHC | 1.7 | NR | 1.7 | 1.7 | NR | 1.7 | NR | | |

TABLE 12-continued

Research Stability of 150 mg/mL mAb1 Formulated Drug Substance Stored at −30° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.0 mL
Container/Closure
5 mL polycarbonate vial with silicone lined polypropylene screw cap
Length of Storage at −30° C. (months)

| | Assay | 0 | 1 | 3 | 6 | 9 | 12 | 18 | 24 | 36 |
|---|---|---|---|---|---|---|---|---|---|---|
| Purity by | % HMW | 0.5 | 0.5 | 0.5 | 0.5 | 0.5 | 0.5 | 0.5 | | |
| SE-UPLC | % Native | 99.2 | 99.1 | 99.3 | 99.3 | 99.3 | 99.3 | 99.3 | | |
| | % LMW | 0.4 | 0.4 | 0.3 | 0.2 | 0.2 | 0.3 | 0.2 | | |
| Charge | % Acidic | 19.1 | 19.2 | 21.2 | 20.9 | 19.4 | 19.7 | 17.6 | | |
| variant | % Main | 66.8 | 66.3 | 66.2 | 66.9 | 68.0 | 67.1 | 69.9 | | |
| analysis by | % Basic | 14.1 | 14.5 | 12.6 | 12.3 | 12.6 | 13.2 | 12.5 | | |
| CEX-UPLC | | | | | | | | | | |
| Charge | % Acidic | 31.3 | NR | 30.5 | 30.8 | NR | 30.9 | NR | | |
| variant | % Main | 56.3 | NR | 57.1 | 57.0 | NR | 57.0 | NR | | |
| analysis by | % Basic | 12.4 | NR | 12.4 | 12.3 | NR | 12.1 | NR | | |
| iCIEF | | | | | | | | | | |
| % Relative potency (bioassay) | | 116 | NR | NR | NR | NR | 149 | NR | | |

CEX = Cation exchange;
DS = Drug substance;
HMW = High molecular weight;
iCIEF = Imaging capillary isoelectric focusing;
LMW = Low molecular weight;
MCE-SDS = Microchip capillary electrophoresis-sodium dodecyl sulfate;
NR = Not required;
OD = Optical density;
RP = Reverse phase;
SE = Size exclusion;
UPLC = Ultra-performance liquid chromatography

TABLE 13

Research Stability of 150 mg/mL mAb1 Formulated Drug Substance Stored at −20° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.0 mL
Container/Closure
5 mL polycarbonate vial with silicone lined polypropylene screw cap
Length of Storage at −20° C. (months)

| | Assay | 0 | 1 | 3 | 6 | 9 | 12 | 18 | 24 | 36 |
|---|---|---|---|---|---|---|---|---|---|---|
| | Color and appearance | Pass | Pass | Pass | Pass | Pass | Pass | Pass | | |
| | Turbidity (Increase in OD at 405 nm) | 0.00 | 0.00 | 0.00 | 0.00 | 0.00 | 0.02 | 0.00 | | |
| | pH | 5.3 | 5.2 | 5.2 | 5.3 | 5.3 | 5.2 | 5.3 | | |
| | % Protein recovered by SEC-UPLC | 100 | 108 | 108 | 100 | 99 | 106 | 100 | | |
| Non- | % Main Peak Purity | 97.4 | NR | 96.0 | 96.1 | NR | 97.2 | NR | | |
| reduced | % LMW Species | 2.5 | NR | 3.9 | 3.8 | NR | 2.7 | NR | | |
| MCE | % HMW Species | 0.1 | NR | 0.0 | 0.1 | NR | 0.2 | NR | | |
| Reduced | % Purity | 94.2 | NR | 94.3 | 95.1 | NR | 95.1 | NR | | |
| MCE | % LMW Species | 2.2 | NR | 2.3 | 1.9 | NR | 2.0 | NR | | |
| | % NGHC | 1.7 | NR | 1.8 | 1.7 | NR | 1.7 | NR | | |
| Purity by | % HMW | 0.5 | 0.5 | 0.5 | 0.5 | 0.5 | 0.5 | 0.5 | | |
| SE-UPLC | % Native | 99.2 | 99.2 | 99.2 | 99.3 | 99.3 | 99.3 | 99.3 | | |
| | % LMW | 0.4 | 0.3 | 0.3 | 0.2 | 0.2 | 0.2 | 0.2 | | |
| Charge | % Acidic | 19.1 | 19.2 | 21.0 | 20.0 | 19.4 | 19.6 | 17.6 | | |
| variant | % Main | 66.8 | 66.4 | 66.3 | 67.8 | 68.0 | 67.5 | 69.9 | | |
| analysis by | % Basic | 14.1 | 14.4 | 12.7 | 12.2 | 12.6 | 13.0 | 12.5 | | |
| CEX-UPLC | | | | | | | | | | |

TABLE 13-continued

Research Stability of 150 mg/mL mAb1 Formulated Drug Substance Stored at −20° C.

Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap

| Assay | | Length of Storage at −20° C. (months) | | | | | | | | |
|---|---|---|---|---|---|---|---|---|---|---|
| | | 0 | 1 | 3 | 6 | 9 | 12 | 18 | 24 | 36 |
| Charge variant analysis by iCIEF | % Acidic | 31.3 | NR | 31.7 | 31.8 | NR | 30.8 | NR | | |
| | % Main | 56.3 | NR | 56.1 | 56.1 | NR | 56.5 | NR | | |
| | % Basic | 12.4 | NR | 12.1 | 12.2 | NR | 12.8 | NR | | |
| % Relative potency (bioassay) | | 116 | NR | NR | NR | NR | 125 | NR | | |

CEX = Cation exchange;
DS = Drug substance;
HMW = High molecular weight;
iCIEF = Imaging capillary isoelectric focusing;
LMW = Low molecular weight;
MCE-SDS = Microchip capillary electrophoresis-sodium dodecyl sulfate;
NR = Not required;
OD = Optical density;
RP = Reverse phase;
SE = Size exclusion;
UPLC = Ultra-performance liquid chromatography

TABLE 14

Research Stability of 150 mg/mL mAb10 Formulated Drug Substance - Effect of Accelerated Conditions Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap

| Assay | | T = 0 | 5° C. Storage (months) | | 25° C./60% RH Storage (months) | | 40° C./75% RH Storage (months) | |
|---|---|---|---|---|---|---|---|---|
| | | | 1 | 2 | 1 | 2 | 1 | 2 |
| Color and appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 |
| pH | | 5.3 | 5.2 | 5.2 | 5.2 | 5.2 | 5.2 | 5.2 |
| % Protein recovered by RP-UPLC | | 100 | 109 | 103 | 110 | 107 | 108 | 106 |
| Non-reduced MCE | % Main Peak Purity | 97.4 | 96.3 | 96.4 | 96.1 | 95.7 | 93.8 | 92.7 |
| | % LMW Species | 2.5 | 3.7 | 3.5 | 3.6 | 3.8 | 5.2 | 5.7 |
| | % HMW Species | 0.1 | 0.1 | 0.1 | 0.4 | 0.5 | 1.0 | 1.6 |
| Reduced MCE | % Purity | 94.2 | 94.2 | 94.8 | 94.5 | 94.5 | 94.1 | 92.1 |
| | % LMW Species | 2.2 | 2.3 | 2.0 | 2.1 | 2.2 | 2.4 | 3.8 |
| | % NGHC | 1.7 | 1.7 | 1.7 | 1.8 | 1.6 | 1.7 | 1.8 |
| Purity by SE-UPLC | % HMW | 0.5 | 0.5 | 0.6 | 0.8 | 1.0 | 2.4 | 5.1 |
| | % Native | 99.2 | 99.1 | 99.2 | 98.8 | 98.8 | 96.6 | 94.1 |
| | % LMW | 0.4 | 0.4 | 0.3 | 0.4 | 0.3 | 0.9 | 0.8 |
| Charge variant analysis by CEX-UPLC | % Acidic | 19.1 | 19.0 | 19.6 | 18.9 | 21.9 | 28.7 | 50.0 |
| | % Main | 66.8 | 66.6 | 67.9 | 66.3 | 64.9 | 55.7 | 36.5 |
| | % Basic | 14.1 | 14.3 | 12.6 | 14.8 | 13.2 | 15.5 | 13.5 |

TABLE 14-continued

Research Stability of 150 mg/mL mAb10 Formulated Drug Substance - Effect of Accelerated Conditions Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap

| | | | 5° C. Storage (months) | | 25° C./60% RH Storage (months) | | 40° C./75% RH Storage (months) | |
|---|---|---|---|---|---|---|---|---|
| | Assay | T = 0 | 1 | 2 | 1 | 2 | 1 | 2 |
| Charge | % Acidic | 31.3 | 31.7 | 31.6 | 32.2 | 33.0 | 37.7 | 46.2 |
| variant | % Main | 56.3 | 55.5 | 56.3 | 54.6 | 53.5 | 46.3 | 35.6 |
| analysis by iCIEF | % Basic | 12.4 | 12.8 | 12.1 | 13.3 | 13.5 | 16.0 | 18.2 |

CEX = Cation exchange;
DS = Drug substance;
HMW = High molecular weight;
iCIEF = Imaging capillary isoelectric focusing;
LMW = Low molecular weight;
MCE-SDS = Microchip capillary electrophoresis-sodium dodecyl sulfate;
NR = Not required;
OD = Optical density;
RH = Relative humidity;
RP = Reverse phase;
SE = Size exclusion;
UPLC = Ultra-performance liquid chromatography

TABLE 15

Research Stability of 150 mg/mL mAb1 Formulated Drug Substance - Effect of Stress Conditions Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap

| | | No Stress | Orbital Shaking (hours) | | Freeze/Thaw (cycles) | |
|---|---|---|---|---|---|---|
| | Assay | T = 0 | 24 | 48 | 4 | 8 |
| Color and appearance | | Pass | Pass | Pass | Pass | Pass |
| Turbidity (Increase in OD at 405 nm) | | 0.00 | 0.00 | 0.00 | 0.00 | 0.00 |
| pH | | 5.3 | 5.3 | 5.3 | 5.3 | 5.3 |
| % Protein recovered by RP-UPLC | | 100 | 101 | 102 | 99 | 114 |
| Non- | % Main Peak Purity | 97.4 | NR | 96.0 | NR | 97.4 |
| reduced | % LMW Species | 2.5 | NR | 3.9 | NR | 2.5 |
| MCE | % HMW Species | 0.1 | NR | 0.1 | NR | 0.1 |
| Reduced | % Purity | 94.2 | NR | 94.5 | NR | 94.9 |
| MCE | % LMW Species | 2.2 | NR | 2.1 | NR | 2.2 |
| | % NGHC | 1.7 | NR | 1.7 | NR | 1.5 |
| Purity by | % HMW | 0.5 | 0.5 | 0.5 | 0.5 | 0.5 |
| SE-UPLC | % Native | 99.2 | 99.2 | 99.1 | 99.3 | 99.2 |
| | % LMW | 0.4 | 0.3 | 0.4 | 0.3 | 0.3 |
| Charge | % Acidic | 19.1 | 19.4 | 19.2 | 19.7 | 19.6 |
| variant | % Main | 66.8 | 66.5 | 66.5 | 66.6 | 66.7 |
| analysis by CEX-UPLC | % Basic | 14.1 | 14.1 | 14.3 | 13.7 | 13.8 |

TABLE 15-continued

Research Stability of 150 mg/mL mAb1 Formulated Drug Substance - Effect of Stress Conditions Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap

| | | No Stress | Orbital Shaking (hours) | | Freeze/Thaw (cycles) | |
|---|---|---|---|---|---|---|
| Assay | | T = 0 | 24 | 48 | 4 | 8 |
| Charge variant analysis by iCIEF | % Acidic | 31.3 | NR | 31.2 | NR | 31.8 |
| | % Main | 56.3 | NR | 56.3 | NR | 56.0 |
| | % Basic | 12.4 | NR | 12.6 | NR | 12.2 |

CEX = Cation exchange;
DS = Drug substance;
HMW = High molecular weight;
iCIEF = Imaging capillary isoelectric focusing;
LMW = Low molecular weight;
MCE-SDS = Microchip capillary electrophoresis-sodium dodecyl sulfate;
NR = Not required;
OD = Optical density;
RP = Reverse phase;
SE = Size exclusion;
UPLC = Ultra-performance liquid chromatography

TABLE 16

Research Stability of 15 mg/mL mAb1 Formulated Drug Substance Stored at −80° C.

Formulation
15 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap
Length of Storage at −80° C. (months)

| Assay | | 0 | 1 | 3 | 6 | 9 | 12 | 18 | 24 | 36 |
|---|---|---|---|---|---|---|---|---|---|---|
| Color and appearance | | Pass | Pass | Pass | Pass | Pass | Pass | Pass | | |
| Turbidity (Increase in OD at 405 nm) | | 0.00 | 0.00 | 0.00 | 0.00 | 0.00 | 0.00 | 0.00 | | |
| pH | | 5.3 | 5.3 | 5.3 | 5.3 | 5.3 | 5.2 | 5.3 | | |
| % Protein recovered by SEC-UPLC | | 100 | 106 | 100 | 99 | 100 | 101 | 97 | | |
| Non-reduced MCE | % Main Peak Purity | 96.6 | NR | 96.8 | 96.5 | NR | 97.7 | NR | | |
| | % LMW Species | 3.4 | NR | 3.1 | 3.4 | NR | 2.2 | NR | | |
| | % HMW Species | 0.0 | NR | 0.1 | 0.1 | NR | 0.1 | NR | | |
| Reduced MCE | % Purity | 94.5 | NR | 94.9 | 94.9 | NR | 95.0 | NR | | |
| | % LMW Species | 2.0 | NR | 2.0 | 2.2 | NR | 2.0 | NR | | |
| | % NGHC | 1.7 | NR | 1.7 | 1.6 | NR | 1.6 | NR | | |
| Purity by SE-UPLC | % HMW | 0.4 | 0.4 | 0.4 | 0.4 | 0.4 | 0.4 | 0.4 | | |
| | % Native | 99.3 | 99.3 | 99.4 | 99.4 | 99.3 | 99.4 | 99.4 | | |
| | % LMW | 0.4 | 0.4 | 0.3 | 0.2 | 0.3 | 0.2 | 0.2 | | |
| Charge variant analysis by CEX-UPLC | % Acidic | 19.3 | 19.2 | 20.7 | 20.6 | 19.0 | 19.8 | 17.6 | | |
| | % Main | 66.8 | 66.6 | 66.8 | 67.2 | 68.7 | 67.1 | 70.1 | | |
| | % Basic | 13.9 | 14.1 | 12.5 | 12.2 | 12.3 | 13.1 | 12.3 | | |

TABLE 16-continued

Research Stability of 15 mg/mL mAb1 Formulated Drug Substance Stored at −80° C.

Formulation
15 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap

| | Assay | \multicolumn{9}{c}{Length of Storage at −80° C. (months)} |
|---|---|---|---|---|---|---|---|---|---|---|
| | | 0 | 1 | 3 | 6 | 9 | 12 | 18 | 24 | 36 |
| Charge variant analysis by iCIEF | % Acidic | 31.0 | NR | 30.7 | 30.6 | NR | 31.1 | NR | | |
| | % Main | 56.9 | NR | 57.4 | 57.0 | NR | 56.2 | NR | | |
| | % Basic | 12.1 | NR | 12.0 | 12.4 | NR | 12.7 | NR | | |
| | % Relative potency (bioassay) | 82 | NR | NR | NR | NR | NA | NR | | |

CEX = Cation exchange;

DS = Drug substance;

HMW = High molecular weight;

iCIEF = Imaging capillary isoelectric focusing;

LMW = Low molecular weight;

MCE-SDS = Microchip capillary electrophoresis-sodium dodecyl sulfate;

NR = Not required;

OD = Optical density;

RP = Reverse phase;

SE = Size exclusion;

UPLC = Ultra-performance liquid chromatography

TABLE 17

Research Stability of 15 mg/mL mAb1 Formulated Drug Substance Stored at −30° C.

Formulation
15 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap

| | Assay | \multicolumn{9}{c}{Length of Storage at −30° C. (months)} |
|---|---|---|---|---|---|---|---|---|---|---|
| | | 0 | 1 | 3 | 6 | 9 | 12 | 18 | 24 | 36 |
| | Color and appearance | Pass | Pass | Pass | Pass | Pass | Pass | Pass | | |
| | Turbidity (Increase in OD at 405 nm) | 0.00 | 0.00 | 0.00 | 0.00 | 0.00 | 0.00 | 0.00 | | |
| | pH | 5.3 | 5.3 | 5.3 | 5.3 | 5.3 | 5.3 | 5.3 | | |
| | % Protein recovered by SEC-UPLC | 100 | 106 | 100 | 100 | 99 | 102 | 97 | | |
| Non-reduced MCE | % Main Peak Purity | 96.6 | NR | 96.8 | 96.7 | NR | 97.5 | NR | | |
| | % LMW Species | 3.4 | NR | 3.1 | 3.3 | NR | 2.4 | NR | | |
| | % HMW Species | 0.0 | NR | 0.1 | 0.1 | NR | 0.1 | NR | | |
| Reduced MCE | % Purity | 94.5 | NR | 95.3 | 95.1 | NR | 94.5 | NR | | |
| | % LMW Species | 2.0 | NR | 1.8 | 1.9 | NR | 2.1 | NR | | |
| | % NGHC | 1.7 | NR | 1.6 | 1.6 | NR | 1.7 | NR | | |
| Purity by SE-UPLC | % HMW | 0.4 | 0.4 | 0.4 | 0.4 | 0.4 | 0.4 | 0.4 | | |
| | % Native | 99.3 | 99.3 | 99.4 | 99.4 | 99.4 | 99.4 | 99.4 | | |
| | % LMW | 0.4 | 0.4 | 0.3 | 0.2 | 0.3 | 0.3 | 0.2 | | |
| Charge variant analysis by CEX-UPLC | % Acidic | 19.3 | 19.5 | 20.5 | 20.1 | 19.7 | 19.8 | 17.8 | | |
| | % Main | 66.8 | 66.3 | 67.0 | 67.9 | 67.8 | 67.1 | 70.0 | | |
| | % Basic | 13.9 | 14.2 | 12.5 | 12.0 | 12.5 | 13.1 | 12.3 | | |

TABLE 17-continued

Research Stability of 15 mg/mL mAb1 Formulated Drug Substance Stored at −30° C.

Formulation
15 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap
Length of Storage at −30° C. (months)

| Assay | | 0 | 1 | 3 | 6 | 9 | 12 | 18 | 24 | 36 |
|---|---|---|---|---|---|---|---|---|---|---|
| Charge | % Acidic | 31.0 | NR | 30.3 | 30.5 | NR | 31.2 | NR | | |
| variant | % Main | 56.9 | NR | 57.6 | 56.9 | NR | 55.9 | NR | | |
| analysis by | % Basic | 12.1 | NR | 12.1 | 12.6 | NR | 12.9 | NR | | |
| iCIEF | | | | | | | | | | |
| % Relative potency (bioassay) | | 82 | NR | NR | NR | NR | NA | NR | | |

CEX = Cation exchange;
DS = Drug substance;
HMW = High molecular weight;
iCIEF = Imaging capillary isoelectric focusing;
LMW = Low molecular weight;
MCE-SDS = Microchip capillary electrophoresis-sodium dodecyl sulfate;
NR = Not required;
OD = Optical density;
RP = Reverse phase;
SE = Size exclusion;
UPLC = Ultra-performance liquid chromatography

TABLE 18

Research Stability of 15 mg/mL mAb1 Formulated Drug Substance Stored at −20° C.

Formulation
15 mg/mL mAb1, 10 mM acetate, 5% (w/v) sucrose, 70 mM L-arginine hydrochloride, 0.08% (w/v) polysorbate 80, pH 5.3
Fill Volume
2.0 mL
Container/Closure
5 mL polycarbonate vial with silicone lined polypropylene screw cap
Length of Storage at −20° C. (months)

| Assay | | 0 | 1 | 3 | 6 | 9 | 12 | 18 | 24 | 36 |
|---|---|---|---|---|---|---|---|---|---|---|
| Color and appearance | | Pass | Pass | Pass | Pass | Pass | Pass | Pass | | |
| Turbidity (Increase in OD at 405 nm) | | 0.00 | 0.00 | 0.00 | 0.00 | 0.00 | 0.00 | 0.00 | | |
| pH | | 5.3 | 5.3 | 5.3 | 5.3 | 5.4 | 5.3 | 5.4 | | |
| % Protein recovered by SEC-UPLC | | 100 | 107 | 100 | 100 | 99 | 102 | 98 | | |
| Non- | % Main Peak Purity | 96.6 | NR | 96.5 | 96.5 | NR | 97.8 | NR | | |
| reduced | % LMW Species | 3.4 | NR | 3.3 | 3.5 | NR | 2.2 | NR | | |
| MCE | % HMW Species | 0.0 | NR | 0.2 | 0.1 | NR | 0.1 | NR | | |
| Reduced | % Purity | 94.5 | NR | 94.9 | 94.8 | NR | 94.7 | NR | | |
| MCE | % LMW Species | 2.0 | NR | 1.8 | 1.9 | NR | 2.0 | NR | | |
| | % NGHC | 1.7 | NR | 1.7 | 1.8 | NR | 1.7 | NR | | |
| Purity by | % HMW | 0.4 | 0.3 | 0.4 | 0.4 | 0.4 | 0.3 | 0.4 | | |
| SE-UPLC | % Native | 99.3 | 99.3 | 99.4 | 99.4 | 99.4 | 99.4 | 99.4 | | |
| | % LMW | 0.4 | 0.4 | 0.3 | 0.2 | 0.3 | 0.2 | 0.2 | | |
| Charge | % Acidic | 19.3 | 19.3 | 20.3 | 19.7 | 19.2 | 19.6 | 17.6 | | |
| variant | % Main | 66.8 | 66.5 | 67.2 | 68.1 | 68.1 | 67.2 | 69.9 | | |
| analysis by | % Basic | 13.9 | 14.1 | 12.6 | 12.2 | 12.7 | 13.2 | 12.5 | | |
| CEX-UPLC | | | | | | | | | | |

TABLE 18-continued

Research Stability of 15 mg/mL mAb1 Formulated Drug Substance Stored at −20° C.

Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.0 mL
Container/Closure
5 mL polycarbonate vial with silicone lined polypropylene screw cap Length of Storage at −20° C. (months)

| | Assay | 0 | 1 | 3 | 6 | 9 | 12 | 18 | 24 | 36 |
|---|---|---|---|---|---|---|---|---|---|---|
| Charge | % Acidic | 31.0 | NR | 30.3 | 30.9 | NR | 30.9 | NR | | |
| variant | % Main | 56.9 | NR | 56.9 | 57.1 | NR | 56.2 | NR | | |
| analysis by | % Basic | 12.1 | NR | 12.8 | 12.0 | NR | 13.0 | NR | | |
| iCIEF | | | | | | | | | | |
| | % Relative potency (bioassay) | 82 | NR | NR | NR | NR | NA | NR | | |

CEX = Cation exchange;

DS = Drug substance;

HMW = High molecular weight;

iCIEF = Imaging capillary isoelectric focusing;

LMW = Low molecular weight;

MCE-SDS = Microchip capillary electrophoresis-sodium dodecyl sulfate;

NR = Not required;

OD = Optical density;

RP = Reverse phase;

SE = Size exclusion;

UPLC = Ultra-performance liquid chromatography

TABLE 19

Research Stability of 15 mg/mL mAb1 Formulated Drug Substance - Effect of Accelerated Conditions Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.0 mL
Container/Closure
5 mL polycarbonate vial with silicone lined polypropylene screw cap

| | | | 5° C. Storage (months) | | 25° C./60% RH Storage (months) | | 40° C./75% RH Storage (months) | |
|---|---|---|---|---|---|---|---|---|
| | Assay | T = 0 | 1 | 2 | 1 | 2 | 1 | 2 |
| Color and appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 |
| pH | | 5.3 | 5.3 | 5.3 | 5.3 | 5.3 | 5.3 | 5.3 |
| % Protein recovered by RP-UPLC | | 100 | 107 | 102 | 109 | 104 | 110 | 103 |
| Non- | % Main Peak Purity | 96.6 | 96.8 | 96.8 | 96.6 | 96.6 | 95.4 | 94.6 |
| reduced | % LMW Species | 3.4 | 3.1 | 3.1 | 3.3 | 3.2 | 4.4 | 5.0 |
| MCE | % HMW Species | 0.0 | 0.1 | 0.1 | 0.1 | 0.2 | 0.2 | 0.4 |
| Reduced | % Purity | 94.5 | 94.4 | 94.6 | 95.3 | 94.7 | 93.4 | 93.5 |
| MCE | % LMW Species | 2.0 | 2.0 | 1.9 | 2.0 | 2.1 | 2.6 | 2.7 |
| | % NGHC | 1.7 | 1.8 | 1.7 | 1.7 | 1.6 | 1.8 | 1.7 |
| Purity by | % HMW | 0.4 | 0.3 | 0.3 | 0.4 | 0.4 | 0.9 | 2.0 |
| SE-UPLC | % Native | 99.3 | 99.3 | 99.4 | 99.3 | 99.3 | 98.6 | 97.2 |
| | % LMW | 0.4 | 0.4 | 0.3 | 0.4 | 0.3 | 0.5 | 0.9 |
| Charge | % Acidic | 19.3 | 19.3 | 19.4 | 20.2 | 21.6 | 27.3 | 46.8 |
| variant | % Main | 66.8 | 66.6 | 68.1 | 65.2 | 65.2 | 57.1 | 39.3 |
| analysis by | % Basic | 13.9 | 14.2 | 12.5 | 14.7 | 13.2 | 15.6 | 14.0 |
| CEX-UPLC | | | | | | | | |

TABLE 19-continued

Research Stability of 15 mg/mL mAb1 Formulated Drug Substance - Effect of Accelerated Conditions Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.0 mL
Container/Closure
5 mL polycarbonate vial with silicone lined polypropylene screw cap

| | | | 5° C. Storage (months) | | 25° C./60% RH Storage (months) | | 40° C./75% RH Storage (months) | |
|---|---|---|---|---|---|---|---|---|
| | Assay | T = 0 | 1 | 2 | 1 | 2 | 1 | 2 |
| Charge | % Acidic | 31.0 | 29.6 | 31.0 | 30.5 | 32.2 | 37.2 | 46.6 |
| variant | % Main | 56.9 | 58.2 | 56.6 | 56.3 | 53.7 | 48.2 | 39.1 |
| analysis by iCIEF | % Basic | 12.1 | 12.2 | 12.4 | 13.3 | 14.1 | 14.6 | 14.3 |

CEX = Cation exchange;
DS = Drug substance;
HMW = High molecular weight;
iCIEF = Imaging capillary isoelectric focusing;
LMW = Low molecular weight;
MCE-SDS = Microchip capillary electrophoresis-sodium dodecyl sulfate;
NR = Not required;
OD = Optical density;
RH = Relative humidity;
RP = Reverse phase;
SE = Size exclusion;
UPLC = Ultra-performance liquid chromatography

TABLE 20

Research Stability of 15 mg/mL mAb1 Formulated Drug Substance - Effect of Stress Conditions Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.0 mL
Container/Closure
5 mL polycarbonate vial with silicone lined polypropylene screw cap

| | | No Stress | Orbital Shaking (hours) | | Freeze/Thaw (cycles) | |
|---|---|---|---|---|---|---|
| | Assay | T = 0 | 24 | 48 | 4 | 8 |
| Color and appearance | | Pass | Pass | Pass | Pass | Pass |
| Turbidity (Increase in OD at 405 nm) | | 0.00 | 0.00 | 0.00 | 0.00 | 0.00 |
| pH | | 5.3 | 5.3 | 5.3 | 5.3 | 5.3 |
| % Protein recovered by RP-UPLC | | 100 | 99 | 99 | 98 | 115 |
| Non- | % Main Peak Purity | 96.6 | NR | 96.7 | NR | 97.7 |
| reduced | % LMW Species | 3.4 | NR | 3.3 | NR | 2.2 |
| MCE | % HMW Species | 0.0 | NR | 0.0 | NR | 0.1 |
| Reduced | % Purity | 94.5 | NR | 95.1 | NR | 94.5 |
| MCE | % LMW Species | 2.0 | NR | 1.8 | NR | 2.1 |
| | % NGHC | 1.7 | NR | 1.7 | NR | 1.7 |
| Purity by | % HMW | 0.4 | 0.3 | 0.3 | 0.4 | 0.4 |
| SE-UPLC | % Native | 99.3 | 99.3 | 99.2 | 99.4 | 99.3 |
| | % LMW | 0.4 | 0.4 | 0.5 | 0.2 | 0.3 |
| Charge | % Acidic | 19.3 | 19.2 | 19.4 | 20.0 | 20.1 |
| variant | % Main | 66.8 | 66.9 | 66.5 | 66.8 | 66.6 |
| analysis by CEX-UPLC | % Basic | 13.9 | 14.0 | 14.1 | 13.2 | 13.3 |

TABLE 20-continued

Research Stability of 15 mg/mL mAb1 Formulated Drug Substance - Effect of Stress Conditions Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.0 mL
Container/Closure
5 mL polycarbonate vial with silicone lined polypropylene screw cap

|  |  | No Stress | Orbital Shaking (hours) | | Freeze/Thaw (cycles) | |
| --- | --- | --- | --- | --- | --- | --- |
| Assay | | T = 0 | 24 | 48 | 4 | 8 |
| Charge variant analysis by iCIEF | % Acidic | 31.0 | NR | 30.8 | NR | 31.0 |
| | % Main | 56.9 | NR | 56.7 | NR | 56.8 |
| | % Basic | 12.1 | NR | 12.5 | NR | 12.3 |

CEX = Cation exchange;
DS = Drug substance;
HMW = High molecular weight;
iCIEF = Imaging capillary isoelectric focusing;
LMW = Low molecular weight;
MCE-SDS = Microchip capillary electrophoresis-sodium dodecyl sulfate;
NR = Not required;
OD = Optical density;
RP = Reverse phase;
SE = Size exclusion;
UPLC = Ultra-performance liquid chromatography

Example 7: Stability of Liquid Formulated Anti-IL-33 Antibody Drug Product

Nine months of research stability data are available to date for the 15 mg/mL and 150 mg/mL drug product formulation of mAb1 in glass vials. Both antibody concentrations were physically and chemically stable when stored at 2-8° C. for 9 months (see Tables 21 and 22). An additional stability study of 150 mg/ml mAb1 drug product was observed to be physically and chemically stable when stored at 2-8° C. for 24 months (see Table 23). No appreciable change in the physical or chemical stability was detected in any of the monitored attributes.

Results from the analysis of the mAb1 drug product formulations, at 15 mg/mL and 150 mg/mL, after incubation under accelerated and stress conditions are provided in Tables 24 and 25, respectively. The mAb1 drug product formulation was physically and chemically stable when agitated (orbital shaking at 250 rpm at ambient temperature) for 48 hours. No appreciable change in the physical or chemical stability was detected in any of the monitored attributes. For both the 15 mg/mL and the 150 mg/mL drug product formulations, when incubated at 25° C. for 1 month, no appreciable change in HMW and LMW species was observed, indicating that the mAb1 drug product formulations can be exposed to short periods of time at room temperature. After incubation for 2 months at 40° C./75% RH, appreciable formation of HMW species and charge variants (increased relative percentage of acidic species) were detected. The results from this accelerated condition demonstrated that an increase in HMW species and the formation of charge variants were the main degradation pathways for the drug product formulations.

Additionally, six months of research stability data are available, to date, for the 150 mg/mL drug product formulation in pre-filled syringe (PFS). The stability has been tested in five PFS. The stability data are provided in Tables 26 to 34. Three months of research stability data are available for the 75 mg/mL drug product formulation in glass vials (see Table 36).

TABLE 21

Research Stability of 15 mg/mL mAb1 Drug Product in glass vials Storedat 2-8° C.

Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
5 mL Type 1 borosilicate glass vials with a 20 mm FluroTec ®
coated West S2-451 4432/50 GRY B2-40 stoppers

| | Length of Storage at 2-8° C. (months) | | | | | | | | |
| --- | --- | --- | --- | --- | --- | --- | --- | --- | --- |
| Assay | 0 | 1 | 3 | 6 | 9 | 12 | 18 | 24 | 36 |
| Color and appearance | Pass | Pass | Pass | Pass | Pass | Pass | Pass | | |
| Turbidity (Increase in OD at 405 nm) | 0.00 | 0.00 | 0.00 | 0.00 | 0.00 | 0.00 | 0.00 | | |
| pH | 5.3 | 5.3 | 5.3 | 5.3 | 5.3 | 5.2 | 5.3 | | |
| % Protein recovered by SEC-UPLC | 100 | 103 | 100 | 99 | 100 | 103 | 98 | | |

TABLE 21-continued

Research Stability of 15 mg/mL mAb1 Drug Product in glass vials Storedat 2-8° C.

Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
5 mL Type 1 borosilicate glass vials with a 20 mm FluroTec ®
coated West S2-451 4432/50 GRY B2-40 stoppers
Length of Storage at 2-8° C. (months)

| | Assay | 0 | 1 | 3 | 6 | 9 | 12 | 18 | 24 | 36 |
|---|---|---|---|---|---|---|---|---|---|---|
| Subvisible particulate analysis by HIAC (#/mL) | ≥10 μm | 2 | 4 | 11 | 12 | NR | 13 | NR | | |
| | ≥25 μm | 0 | 0 | 0 | 0 | NR | 0 | NR | | |
| Particulate analysis by MFI (particles/mL) | 2 to 10 μm | 285 | 2093 | 1215 | 787 | NR | 1062 | NR | | |
| | ≥10 μm | 23 | 25 | 7 | 13 | NR | 7 | NR | | |
| | ≥25 μm | 7 | 2 | 0 | 3 | NR | 2 | NR | | |
| Non-reduced MCE | % Main Peak Purity | 96.3 | 96.4 | 96.5 | 96.4 | NR | 97.2 | NR | | |
| | % LMW Species | 3.6 | 3.6 | 3.5 | 3.6 | NR | 2.6 | NR | | |
| | % HMW Species | 0.1 | 0.0 | 0.1 | 0.0 | NR | 0.2 | NR | | |
| Reduced MCE | % Purity | 94.5 | 94.2 | 94.9 | 94.1 | NR | 94.8 | NR | | |
| | % LMW Species | 2.1 | 2.2 | 2.1 | 2.2 | NR | 1.9 | NR | | |
| | % NGHC | 1.7 | 1.7 | 1.7 | 1.9 | NR | 1.8 | NR | | |
| Purity by SE-UPLC | % HMW | 0.4 | 0.3 | 0.3 | 0.4 | 0.4 | 0.4 | 0.4 | | |
| | % Native | 99.3 | 99.3 | 99.4 | 99.4 | 99.3 | 99.4 | 99.4 | | |
| | % LMW | 0.4 | 0.4 | 0.3 | 0.2 | 0.3 | 0.3 | 0.2 | | |
| Charge variant analysis by CEX-UPLC | % Acidic | 19.6 | 19.2 | 20.0 | 19.9 | 19.5 | 20.0 | 18.0 | | |
| | % Main | 66.5 | 66.7 | 67.4 | 67.7 | 67.8 | 66.6 | 69.4 | | |
| | % Basic | 13.9 | 14.1 | 12.6 | 12.4 | 12.7 | 13.4 | 12.6 | | |
| Charge variant analysis by iCIEF | % Acidic | 30.2 | 30.2 | 30.1 | 30.4 | NR | 31.0 | NR | | |
| | % Main | 57.3 | 57.0 | 57.3 | 57.0 | NR | 55.8 | NR | | |
| | % Basic | 12.5 | 12.9 | 12.6 | 12.5 | NR | 13.1 | NR | | |
| % Polysorbate 80 Recovered by CAD | | 0.075 | 0.077 | 0.077 | 0.082 | NR | 0.088 | NR | | |
| % Relative potency (bioassay) | | 108 | NR | NR | NR | NR | NR | NR | | |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RP = Reverse phase;
SE = Size exclusion;
UPLC = Ultra-performance liquid chromatography

TABLE 22

Research Stability of 150 mg/mL mAb1 Drug Product in Glass Vials Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
5 mL Type 1 borosilicate glass vials with a 20 mm FluroTec ®
coated West S2-451 4432/50 GRY B2-40 stoppers
Length of Storage at 2-8° C. (months)

| Assay | 0 | 1 | 3 | 6 | 9 | 12 | 18 | 24 | 36 |
|---|---|---|---|---|---|---|---|---|---|
| Color and appearance | Pass | Pass | Pass | Pass | Pass | Pass | Pass | | |
| Turbidity (Increase in OD at 405 nm) | 0.00 | 0.00 | 0.00 | 0.00 | 0.00 | 0.01 | 0.00 | | |
| pH | 5.3 | 5.2 | 5.2 | 5.2 | 5.2 | 5.2 | 5.3 | | |
| % Protein recovered by SEC-UPLC | 100 | 103 | 101 | 99 | 98 | 100 | 100 | | |

TABLE 22-continued

Research Stability of 150 mg/mL mAb1 Drug Product in Glass Vials Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
5 mL Type 1 borosilicate glass vials with a 20 mm FluroTec ®
coated West S2-451 4432/50 GRY B2-40 stoppers

| | | Length of Storage at 2-8° C. (months) | | | | | | | | |
|---|---|---|---|---|---|---|---|---|---|---|
| | Assay | 0 | 1 | 3 | 6 | 9 | 12 | 18 | 24 | 36 |
| Subvisible particulate analysis by HIAC (#/mL) | ≥10 µm | 17 | 16 | 11 | 28 | NR | 14 | NR | | |
| | ≥25 µm | 1 | 0 | 0 | 1 | NR | 2 | NR | | |
| Particulate analysis by MFI (particles/mL) | 2 to 10 µm | 231 | 348 | 652 | 1216 | NR | 1157 | NR | | |
| | ≥10 µm | 31 | 11 | 28 | 20 | NR | 16 | NR | | |
| | ≥25 µm | 8 | 2 | 3 | 2 | NR | 0 | NR | | |
| Non-reduced MCE | % Main Peak Purity | 95.6 | 95.6 | 95.6 | 96.0 | NR | 96.8 | NR | | |
| | % LMW Species | 4.3 | 4.4 | 4.1 | 3.7 | NR | 2.8 | NR | | |
| | % HMW Species | 0.2 | 0.1 | 0.3 | 0.3 | NR | 0.4 | NR | | |
| Reduced MCE | % Purity | 94.2 | 93.9 | 94.4 | 94.4 | NR | 94.8 | NR | | |
| | % LMW Species | 2.4 | 2.4 | 2.1 | 2.0 | NR | 1.9 | NR | | |
| | % NGHC | 1.8 | 1.9 | 1.7 | 1.8 | NR | 1.8 | NR | | |
| Purity by SE-UPLC | % HMW | 0.5 | 0.5 | 0.6 | 0.7 | 0.7 | 0.7 | 0.8 | | |
| | % Native | 99.2 | 99.1 | 99.2 | 99.1 | 99.0 | 99.0 | 98.9 | | |
| | % LMW | 0.4 | 0.4 | 0.3 | 0.2 | 0.2 | 0.2 | 0.2 | | |
| Charge variant analysis by CEX-UPLC | % Acidic | 19.3 | 19.3 | 20.2 | 20.0 | 19.0 | 19.7 | 17.7 | | |
| | % Main | 66.6 | 66.7 | 67.0 | 67.4 | 68.2 | 66.7 | 69.5 | | |
| | % Basic | 14.1 | 14.0 | 12.8 | 12.6 | 12.9 | 13.5 | 12.9 | | |
| Charge variant analysis by iCIEF | % Acidic | 31.4 | 30.9 | 30.8 | 30.8 | NA | 30.7 | NR | | |
| | % Main | 56.4 | 56.4 | 56.4 | 56.5 | NA | 56.1 | NR | | |
| | % Basic | 12.2 | 12.8 | 12.8 | 12.7 | NA | 13.2 | NR | | |
| % Polysorbate 80 Recovered by CAD | | 0.084 | 0.087 | 0.084 | 0.092 | NR | 0.090 | NR | | |
| % Relative potency (bioassay) | | 108 | NR | NR | 72 | NR | 115 | NR | | |

CEX = Cation exchange;
DS = Drug substance;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RP = Reverse phase;
SE = Size exclusion;
UPLC = Ultra-performance liquid chromatography

TABLE 23

Research Stability of 150 mg/mL mAb1 Drug Product in glass vials Stored at 2-8° C.

Formulation
150 mg/mL mAb1, 10 mM acetate, 5% (w/v) sucrose, 70 mM L-arginine
hydrochloride, 0.10% (w/v) polysorbate 80, pH 5.3
Fill Volume
0.5 mL
Container/Closure
2 mL Type 1 borosilicate glass vials with a 20 mm FluroTec ®
coated West S2-451 4432/50 GRY B2-40 stoppers

| | | Length of Storage at 2-8° C. (months) | | | | | | | | |
|---|---|---|---|---|---|---|---|---|---|---|
| | Assay | 0 | 1 | 3 | 6 | 9 | 12 | 18 | 24 | 36 |
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 | 0.00 | 0.00 |
| pH | | 5.2 | 5.2 | 5.2 | 5.2 | 5.3 | 5.3 | 5.2 | 5.2 | 5.3 |
| % Protein recovered by RP-UPLC | | 100 | 102 | 103 | 103 | 101 | 106 | 107 | 102 | 100 |
| Purity by SE-UPLC | % HMW | 1.5 | 1.5 | 1.6 | 1.7 | 1.8 | 1.8 | 1.9 | 2.0 | 2.1 |
| | % Native | 98.0 | 98.0 | 97.9 | 97.8 | 97.7 | 97.8 | 97.6 | 97.6 | 97.4 |
| | % LMW | 0.5 | 0.5 | 0.5 | 0.5 | 0.6 | 0.4 | 0.5 | 0.5 | 0.5 |

TABLE 23-continued

Research Stability of 150 mg/mL mAb1 Drug Product in glass vials Stored at 2-8° C.

Formulation
150 mg/mL mAb1, 10 mM acetate, 5% (w/v) sucrose, 70 mM L-arginine
hydrochloride, 0.10% (w/v) polysorbate 80, pH 5.3
Fill Volume
0.5 mL
Container/Closure
2 mL Type 1 borosilicate glass vials with a 20 mm FluroTec ®
coated West S2-451 4432/50 GRY B2-40 stoppers
Length of Storage at 2-8° C. (months)

| | Assay | 0 | 1 | 3 | 6 | 9 | 12 | 18 | 24 | 36 |
|---|---|---|---|---|---|---|---|---|---|---|
| Charge | % Acidic | 29.4 | 28.4 | 28.2 | 28.2 | 28.3 | 28.8 | 29.1 | 29.0 | 30.1 |
| variant | % Main | 66.1 | 67.0 | 67.2 | 67.0 | 66.9 | 66.1 | 64.1 | 65.7 | 64.2 |
| analysis by | % Basic | 4.5 | 4.5 | 4.6 | 4.7 | 4.9 | 5.1 | 6.8 | 5.3 | 5.7 |
| CEX-UPLC | | | | | | | | | | |

CEX = Cation exchange;
DS = Drug substance;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RP = Reverse phase;
SE = Size exclusion;
UPLC = Ultra-performance liquid chromatography

TABLE 24

Research Stability of 15 mg/mL mAb1 Drug Product in glass vials Stored
at Accelerated and Stress Conditions, and Against Agitation Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
5 mL Type 1 borosilicate glass vials with a 13 mm FluroTec ®
coated West S2-451 4432/50 GRY B2-40 stoppers

| | | 25° C./60% RH Storage (months) | | | | 40° C./75% RH Storage (months) | | | Orbital shaking (h) | |
|---|---|---|---|---|---|---|---|---|---|---|
| | Assay | 0 | 1 | 3 | 6 | 0.5 | 1 | 2 | 24 | 48 |
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 | 0.00 | 0.00 |
| pH | | 5.3 | 5.3 | 5.3 | 5.3 | 5.3 | 5.3 | 5.3 | 5.3 | 5.3 |
| % Protein recovered by RP-UPLC | | 100 | 103 | 100 | 99 | 98 | 103 | 100 | 98 | 98 |
| Subvisible | ≥10 µm | 2 | 10 | 8 | 29 | NR | 13 | 13 | NR | 7 |
| particulate analysis by HIAC (#/mL) | ≥25 µm | 0 | 0 | 0 | 0 | NR | 0 | 1 | NR | 0 |
| Particulate | 2 to 10 µm | 285 | 387 | 906 | 1174 | NR | 2222 | 3474 | NR | 378 |
| analysis by | ≥10 µm | 23 | 13 | 10 | 11 | NR | 18 | 43 | NR | 10 |
| MFI (particles/mL) | ≥25 µm | 7 | 5 | 0 | 3 | NR | 2 | 3 | NR | 0 |
| Non- | % Main Peak Purity | 96.3 | 96.1 | 95.8 | 95.5 | NR | 95.2 | 94.5 | NR | 96.4 |
| reduced | % LMW Species | 3.6 | 3.8 | 4.1 | 4.4 | NR | 4.6 | 5.5 | NR | 3.5 |
| MCE | % HMW Species | 0.1 | 0.1 | 0.1 | 0.1 | NR | 0.2 | 0.1 | NR | 0.1 |
| Reduced | % Purity | 96.3 | 96.1 | 95.8 | 95.5 | NR | 95.2 | 94.5 | NR | 96.4 |
| MCE | % LMW Species | 3.6 | 3.8 | 4.1 | 4.4 | NR | 4.6 | 5.5 | NR | 3.5 |
| | % NGHC | 0.1 | 0.1 | 0.1 | 0.1 | NR | 0.2 | 0.1 | NR | 0.1 |
| Purity by | % HMW | 0.4 | 0.3 | 0.4 | 0.5 | 0.5 | 0.7 | 1.3 | 0.3 | 0.3 |
| SE-UPLC | % Native | 99.3 | 99.3 | 99.3 | 99.2 | 99.2 | 98.9 | 97.8 | 99.3 | 99.4 |
| | % LMW | 0.4 | 0.4 | 0.3 | 0.3 | 0.3 | 0.4 | 0.9 | 0.4 | 0.4 |
| Charge | % Acidic | 19.6 | 19.6 | 22.9 | 27.5 | 22.1 | 27.6 | 46.9 | 19.5 | 19.3 |
| variant | % Main | 66.5 | 66.0 | 63.7 | 59.2 | 62.9 | 57.2 | 39.5 | 66.5 | 66.6 |
| analysis by CEX-UPLC | % Basic | 13.9 | 14.4 | 13.4 | 13.3 | 15.0 | 15.2 | 13.6 | 14.0 | 14.0 |

TABLE 24-continued

Research Stability of 15 mg/mL mAb1 Drug Product in glass vials Stored
at Accelerated and Stress Conditions, and Against Agitation Formulation
15 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
5 mL Type 1 borosilicate glass vials with a 13 mm FluroTec ®
coated West S2-451 4432/50 GRY B2-40 stoppers

| | | 25° C./60% RH Storage (months) | | | | 40° C./75% RH Storage (months) | | | Orbital shaking (h) | |
|---|---|---|---|---|---|---|---|---|---|---|
| Assay | | 0 | 1 | 3 | 6 | 0.5 | 1 | 2 | 24 | 48 |
| Charge variant analysis by iCIEF | % Acidic | 30.2 | 30.2 | 32.7 | 36.8 | NR | 38.0 | 45.9 | NR | 30.2 |
| | % Main | 57.3 | 55.8 | 53.5 | 49.2 | NR | 47.8 | 40.4 | NR | 57.4 |
| | % Basic | 12.5 | 14.0 | 13.9 | 14.0 | NR | 14.2 | 13.8 | NR | 12.5 |
| % Polysorbate 80 by CAD | | 0.075 | 0.078 | 0.077 | 0.082 | NR | 0.078 | 0.075 | NR | 0.076 |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RH = Relative humidity;
RP = Reverse phase;
SE = Size exclusion;
UPLC = Ultra-performance liquid chromatography

TABLE 25

Research Stability of 150 mg/mL mAb1 Drug Product in glass vials Stored
at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
5 mL Type 1 borosilicate glass vials with a 13 mm FluroTec ®
coated West S2-451 4432/50 GRY B2-40 stoppers

| | | 25° C./60% RH Storage (months) | | | | 40° C./75% RH Storage (months) | | | Orbital shaking (h) | |
|---|---|---|---|---|---|---|---|---|---|---|
| Assay | | 0 | 1 | 3 | 6 | 0.5 | 1 | 2 | 24 | 48 |
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.01 | 0.00 | 0.00 |
| pH | | 5.3 | 5.2 | 5.2 | 5.3 | 5.3 | 5.2 | 5.3 | 5.3 | 5.3 |
| % Protein recovered by RP-UPLC | | 100 | 104 | 101 | 100 | 97 | 102 | 98 | 101 | 101 |
| Subvisible particulate analysis by HIAC (#/mL) | ≥10 μm | 17 | 16 | 16 | 56 | NR | 30 | 46 | NR | 13 |
| | ≥25 μm | 1 | 0 | 0 | 2 | NR | 1 | 1 | NR | 0 |
| Particulate analysis by MFI (particles/mL) | 2 to 10 μm | 231 | 903 | 2053 | 2700 | NR | 2919 | 1781 | NR | 514 |
| | ≥10 μm | 31 | 25 | 13 | 61 | NR | 48 | 38 | NR | 16 |
| | ≥25 μm | 8 | 3 | 1 | 8 | NR | 2 | 2 | NR | 2 |
| Non-reduced MCE | % Main Peak Purity | 95.6 | 95.5 | 94.2 | 94.1 | NR | 94.1 | 92.1 | NR | 95.6 |
| | % LMW Species | 4.3 | 4.1 | 5.4 | 5.3 | NR | 5.3 | 6.5 | NR | 4.3 |
| | % HMW Species | 0.2 | 0.4 | 0.5 | 0.6 | NR | 0.7 | 1.4 | NR | 0.1 |
| Reduced MCE | % Purity | 94.2 | 94.5 | 94.0 | 93.4 | NR | 93.6 | 92.2 | NR | 94.7 |
| | % LMW Species | 2.4 | 2.0 | 2.4 | 3.0 | NR | 2.7 | 3.5 | NR | 1.9 |
| | % NGHC | 1.8 | 1.7 | 1.8 | 1.7 | NR | 1.8 | 1.7 | NR | 1.7 |
| Purity by SE-UPLC | % HMW | 0.5 | 0.8 | 1.0 | 1.3 | 1.4 | 2.2 | 3.9 | 0.5 | 0.5 |
| | % Native | 99.2 | 98.9 | 98.7 | 98.4 | 98.0 | 96.9 | 95.4 | 99.2 | 99.1 |
| | % LMW | 0.4 | 0.4 | 0.3 | 0.3 | 0.6 | 0.9 | 0.8 | 0.4 | 0.4 |

TABLE 25-continued

Research Stability of 150 mg/mL mAb1 Drug Product in glass vials Stored
at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
5 mL Type 1 borosilicate glass vials with a 13 mm FluroTec ®
coated West S2-451 4432/50 GRY B2-40 stoppers

| | | 25° C./60% RH Storage (months) | | | | 40° C./75% RH Storage (months) | | | Orbital shaking (h) | |
|---|---|---|---|---|---|---|---|---|---|---|
| | Assay | 0 | 1 | 3 | 6 | 0.5 | 1 | 2 | 24 | 48 |
| Charge | % Acidic | 19.3 | 19.9 | 21.2 | 28.9 | 23.4 | 28.8 | 48.5 | 19.1 | 19.2 |
| variant | % Main | 66.6 | 14.6 | 13.3 | 57.7 | 61.4 | 56.1 | 38.0 | 66.7 | 66.7 |
| analysis by | % Basic | 14.1 | 19.9 | 21.2 | 13.4 | 15.1 | 15.2 | 13.5 | 14.2 | 14.1 |
| CEX-UPLC | | | | | | | | | | |
| Charge | % Acidic | 31.4 | 30.9 | 33.5 | 38.0 | NR | 38.7 | 46.2 | NR | 30.4 |
| variant | % Main | 56.4 | 55.4 | 51.8 | 46.6 | NR | 45.1 | 38.4 | NR | 57.1 |
| analysis by | % Basic | 12.2 | 13.7 | 14.7 | 15.4 | NR | 16.1 | 15.4 | NR | 12.5 |
| iCIEF | | | | | | | | | | |
| % Polysorbate 80 by CAD | | 0.084 | 0.086 | 0.083 | 0.090 | NR | 0.084 | 0.081 | NR | 0.084 |

CEX = Cation exchange;
DS = Drug substance;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RH = Relative humidity;
RP = Reverse phase;
SE = Size exclusion;
UPLC = Ultra-performance liquid chromatography

TABLE 26

Research Stability of 150 mg/mL mAb1 Drug Product in 1 mL gOmpi syringes Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
Nuova Ompi EZ-Fill 1 mL long glass syringe with 27G thin wall needle
and FM30 needle shield

| | | Length of Storage at 2-8 ° C. (months) | | | | | | | | |
|---|---|---|---|---|---|---|---|---|---|---|
| | Assay | 0 | 1 | 3 | 6 | 9 | 12 | 18 | 24 | 36 |
| Color and appearance | | Pass | Pass | Pass | Pass | Pass | Pass | Pass | | |
| Turbidity (Increase in OD at 405 nm) | | 0.00 | 0.00 | 0.00 | 0.00 | 0.00 | 0.00 | 0.00 | | |
| pH | | 5.4 | 5.3 | 5.3 | 5.2 | 5.2 | 5.3 | 5.3 | | |
| % Protein recovered by SE-UPLC | | 100 | 101 | 100 | 99 | 102 | 102 | 102 | | |
| Subvisible particulate analysis by HIAC (#/mL) | ≥10 μm | 283 | 357 | 582 | 1128 | NR | 1225 | NR | | |
| | ≥25 μm | 1 | 0 | 1 | 3 | NR | 6 | NR | | |
| Particulate analysis by MFI (particles/mL) | 2 to 10 μm | 12982 | 10541 | 7137 | 7018 | NR | 5375 | NR | | |
| | ≥10 μm | 29 | 228 | 57 | 69 | NR | 67 | NR | | |
| | ≥25 μm | 0 | 3 | 5 | 0 | NR | 2 | NR | | |
| Non-reduced MCE | % Main Peak Purity | 97.0 | 96.8 | 96.7 | 96.7 | NR | 97.4 | NR | | |
| | % LMW Species | 2.9 | 2.9 | 3.2 | 3.2 | NR | 2.2 | NR | | |
| | % HMW Species | 0.1 | 0.3 | 0.1 | 0.1 | NR | 0.4 | NR | | |
| Reduced MCE | % Purity | 94.8 | 94.9 | 94.4 | 94.9 | NR | 94.4 | NR | | |
| | % LMW Species | 2.3 | 1.8 | 2.2 | 2.1 | NR | 2.2 | NR | | |
| | % NGHC | 1.2 | 1.5 | 1.8 | 1.2 | NR | 1.6 | NR | | |
| Purity by SE-UPLC | % HMW | 0.5 | 0.5 | 0.6 | 0.7 | 0.7 | 0.7 | 0.8 | | |
| | % Native | 99.3 | 99.3 | 99.2 | 99.1 | 99.0 | 99.0 | 98.9 | | |
| | % LMW | 0.3 | 0.2 | 0.2 | 0.2 | 0.3 | 0.3 | 0.3 | | |

TABLE 26-continued

Research Stability of 150 mg/mL mAb1 Drug Product in 1 mL gOmpi syringes Stored at 2-8° C.

Formulation
150 mg/mL mAb1, 10 mM acetate, 5% (w/v) sucrose, 70 mM L-arginine hydrochloride, 0.08% (w/v) polysorbate 80, pH 5.3
Fill Volume
1.05 mL
Container/Closure
Nuova Ompi EZ-Fill 1 mL long glass syringe with 27G thin wall needle and FM30 needle shield

| | | Length of Storage at 2-8 °C. (months) | | | | | | | | |
|---|---|---|---|---|---|---|---|---|---|---|
| | Assay | 0 | 1 | 3 | 6 | 9 | 12 | 18 | 24 | 36 |
| Charge variant analysis by CEX-UPLC | % Acidic | 20.3 | 19.4 | 20.0 | 20.0 | 19.8 | 18.3 | 19.0 | | |
| | % Main | 67.9 | 68.4 | 68.8 | 68.6 | 68.5 | 70.9 | 69.8 | | |
| | % Basic | 11.8 | 12.2 | 11.3 | 11.4 | 11.7 | 10.8 | 11.1 | | |
| Charge variant analysis by iCIEF | % Acidic | 31.2 | 31.0 | 31.3 | 30.2 | NR | 31.9 | NR | | |
| | % Main | 57.3 | 57.2 | 56.7 | 58.6 | NR | 56.1 | NR | | |
| | % Basic | 11.6 | 11.9 | 12.0 | 11.2 | NR | 12.0 | NR | | |
| % Polysorbate 80 by CAD | | 0.079 | 0.080 | 0.081 | 0.091 | NR | 0.091 | NR | | |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RP = Reverse phase;
SE = Size exclusion;
UPLC = Ultra-performance liquid chromatography

TABLE 27

Research Stability of 150 mg/mL mAb1 Drug Product in 1 mL gOmpi Syringes Stored at Accelerated and Stress Conditions, and Against Agitation Formulation
150 mg/mL mAb1, 10 mM acetate, 5% (w/v) sucrose, 70 mM L-arginine hydrochloride, 0.08% (w/v) polysorbate 80, pH 5.3
Fill Volume
1.05 mL
Container/Closure
Nuova Ompi EZ-Fill 1 mL long glass syringe with 27G thin wall needle and FM30 needle shield

| | | 25° C./60% RH Storage (months) | | | | 40° C./75% RH Storage (months) | | | Orbital shaking (h) | |
|---|---|---|---|---|---|---|---|---|---|---|
| | Assay | 0 | 1 | 3 | 6 | 0.5 | 1 | 2 | 24 | 48 |
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.01 | 0.02 | 0.00 | 0.00 |
| pH | | 5.4 | 5.3 | 5.3 | 5.3 | 5.3 | 5.3 | 5.3 | 5.3 | 5.3 |
| % Protein recovered by RP-UPLC | | 100 | 100 | 101 | 99 | 99 | 100 | 101 | 101 | 99 |
| Subvisible particulate analysis by HIAC (#/mL) | ≥10 μm | 283 | 613 | 814 | 975 | NR | 1467 | 1584 | NR | 911 |
| | ≥25 μm | 1 | 1 | 1 | 5 | NR | 23 | 5 | NR | 2 |
| Particulate analysis by MFI (particles/mL) | 2 to 10 μm | 12982 | 13554 | 12156 | 9523 | NR | 15308 | 10205 | NR | 15559 |
| | ≥10 μm | 29 | 253 | 74 | 69 | NR | 376 | 79 | NR | 357 |
| | ≥25 μm | 0 | 1 | 0 | 8 | NR | 7 | 7 | NR | 0 |
| Non-reduced MCE | % Main Peak Purity | 97.0 | 96.5 | 96.1 | 95.1 | NR | 94.5 | 92.3 | NR | 96.7 |
| | % LMW Species | 2.9 | 3.2 | 3.5 | 4.1 | NR | 4.5 | 6.6 | NR | 3.0 |
| | % HMW Species | 0.1 | 0.4 | 0.4 | 0.8 | NR | 1.0 | 1.1 | NR | 0.3 |
| Reduced MCE | % Purity | 94.8 | 94.2 | 94.7 | 94.4 | NR | 93.7 | 91.0 | NR | 95.0 |
| | % LMW Species | 2.3 | 2.7 | 2.3 | 2.6 | NR | 3.3 | 5.1 | NR | 1.9 |
| | % NGHC | 1.2 | 1.4 | 1.1 | 1.6 | NR | 1.4 | 2.3 | NR | 1.2 |
| Purity by SE-UPLC | % HMW | 0.5 | 0.8 | 1.0 | 1.3 | 1.2 | 1.9 | 3.6 | 0.5 | 0.5 |
| | % Native | 99.3 | 99.0 | 98.8 | 98.4 | 98.2 | 97.4 | 95.8 | 99.2 | 99.2 |
| | % LMW | 0.3 | 0.2 | 0.2 | 0.3 | 0.6 | 0.7 | 0.6 | 0.3 | 0.3 |

TABLE 27-continued

Research Stability of 150 mg/mL mAb1 Drug Product in 1 mL gOmpi Syringes
Stored at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
Nuova Ompi EZ-Fill 1 mL long glass syringe with 27G thin wall needle
and FM30 needle shield

| | | 25° C./60% RH Storage (months) | | | | 40° C./75% RH Storage (months) | | | Orbital shaking (h) | |
|---|---|---|---|---|---|---|---|---|---|---|
| Assay | | 0 | 1 | 3 | 6 | 0.5 | 1 | 2 | 24 | 48 |
| Charge variant analysis by CEX-UPLC | % Acidic | 20.3 | 20.3 | 23.9 | 28.6 | 26.1 | 32.0 | 54.5 | 20.2 | 19.9 |
| | % Main | 67.9 | 67.0 | 63.9 | 59.1 | 60.5 | 54.0 | 33.6 | 67.7 | 67.9 |
| | % Basic | 11.8 | 12.7 | 12.2 | 12.3 | 13.4 | 13.9 | 11.9 | 12.1 | 12.2 |
| Charge variant analysis by iCIEF | % Acidic | 31.2 | 31.4 | 33.1 | 41.2 | NR | 39.8 | 57.6 | NR | 30.3 |
| | % Main | 57.3 | 56.1 | 53.6 | 45.9 | NR | 43.7 | 26.6 | NR | 58.4 |
| | % Basic | 11.6 | 12.5 | 13.4 | 13.0 | NR | 16.5 | 15.7 | NR | 11.4 |
| % Polysorbate 80 by CAD | | 0.079 | 0.081 | 0.081 | 0.089 | NR | 0.080 | 0.080 | NR | 0.080 |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RH = Relative humidity;
RP = Reverse phase;
SE = Size exclusion;
UPLC = Ultra-performance liquid chromatography

TABLE 28

Research Stability of 150 mg/mL mAb1 Drug Product in 1 mL BD Neopak Syringes Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
BD Neopak SCF 1 mL long glass syringe with 27G thing wall needle
and BD260 needle shield
Length of Storage at 2-8° C. (months)

| Assay | | 0 | 1 | 3 | 6 | 9 | 12 | 18 | 24 | 36 |
|---|---|---|---|---|---|---|---|---|---|---|
| Color and appearance | | Pass | Pass | Pass | Pass | Pass | Pass | Pass | | |
| Turbidity (Increase in OD at 405 nm) | | 0.00 | 0.00 | 0.00 | 0.00 | 0.00 | 0.00 | 0.00 | | |
| pH | | 5.4 | 5.3 | 5.3 | 5.2 | 5.2 | 5.3 | 5.3 | | |
| % Protein recovered by SEC-UPLC | | 100 | 100 | 100 | 99 | 101 | 102 | 102 | | |
| Subvisible particulate analysis by HIAC (#/mL) | ≥10 μm | 34 | 271 | 108 | 41 | NR | 184 | NR | | |
| | ≥25 μm | 0 | 2 | 2 | 0 | NR | 2 | NR | | |
| Particulate analysis by MFI (particles/mL) | 2 to 10 μm | 790 | 2673 | 3306 | 1096 | NR | 2602 | NR | | |
| | ≥10 μm | 2 | 49 | 5 | 3 | NR | 15 | NR | | |
| | ≥25 μm | 0 | 3 | 0 | 0 | NR | 2 | NR | | |
| Non-reduced MCE | % Main Peak Purity | 96.9 | 97.0 | 96.7 | 96.5 | NR | 97.4 | NR | | |
| | % LMW Species | 3.0 | 3.0 | 3.2 | 3.3 | NR | 2.3 | NR | | |
| | % HMW Species | 0.2 | 0.1 | 0.2 | 0.2 | NR | 0.4 | NR | | |
| Reduced MCE | % Purity | 95.4 | 95.2 | 95.2 | 95.0 | NR | 94.2 | NR | | |
| | % LMW Species | 1.7 | 1.9 | 1.7 | 1.9 | NR | 2.2 | NR | | |
| | % NGHC | 1.2 | 1.1 | 1.5 | 1.6 | NR | 1.9 | NR | | |

TABLE 28-continued

Research Stability of 150 mg/mL mAb1 Drug Product in 1 mL BD Neopak Syringes Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
BD Neopak SCF 1 mL long glass syringe with 27G thing wall needle
and BD260 needle shield
Length of Storage at 2-8° C. (months)

| | Assay | 0 | 1 | 3 | 6 | 9 | 12 | 18 | 24 | 36 |
|---|---|---|---|---|---|---|---|---|---|---|
| Purity by SE-UPLC | % HMW | 0.5 | 0.5 | 0.6 | 0.7 | 0.7 | 0.8 | 0.8 | | |
| | % Native | 99.3 | 99.3 | 99.2 | 99.1 | 99.0 | 99.0 | 98.9 | | |
| | % LMW | 0.3 | 0.2 | 0.2 | 0.2 | 0.3 | 0.3 | 0.3 | | |
| Charge variant analysis by CEX-UPLC | % Acidic | 20.1 | 19.6 | 19.9 | 19.9 | 19.7 | 18.1 | 19.3 | | |
| | % Main | 68.1 | 68.1 | 68.6 | 68.6 | 68.5 | 71.1 | 69.6 | | |
| | % Basic | 11.8 | 12.3 | 11.5 | 11.5 | 11.8 | 10.9 | 11.1 | | |
| Charge variant analysis by iCIEF | % Acidic | 30.8 | 30.8 | 30.7 | 30.6 | NR | 32.2 | NR | | |
| | % Main | 57.5 | 57.9 | 58.2 | 57.7 | NR | 55.6 | NR | | |
| | % Basic | 11.7 | 11.4 | 11.2 | 11.6 | NR | 12.2 | NR | | |
| % Polysorbate 80 by CAD | | 0.082 | 0.081 | 0.082 | 0.091 | NR | 0.091 | NR | | |
| % Relative potency (bioassay) | | 107 | NR | NR | 134 | NR | NA | NR | | |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RP = Reverse phase;
SE = Size exclusion;
UPLC = Ultra-performance liquid chromatography

TABLE 29

Research Stability of 150 mg/mL mAb1 Drug Product in 1 mL BD Neopak Syringes
Stored at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
BD Neopak SCF 1 mL long glass syringe with 27G thing wall needle
and BD260 needle shield

| | | 25° C./60% RH Storage (months) | | | | 40° C./75% RH Storage (months) | | | Orbital shaking (h) | |
|---|---|---|---|---|---|---|---|---|---|---|
| | Assay | 0 | 1 | 3 | 6 | 0.5 | 1 | 2 | 24 | 48 |
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.01 | 0.01 | 0.02 | 0.00 | 0.00 |
| pH | | 5.4 | 5.3 | 5.3 | 5.3 | 5.2 | 5.3 | 5.3 | 5.3 | 5.3 |
| % Protein recovered by RP-UPLC | | 100 | 100 | 100 | 98 | 99 | 100 | 100 | 100 | 99 |
| Subvisible particulate analysis by HIAC (#/mL) | ≥10 μm | 34 | 132 | 140 | 179 | NR | 359 | 458 | NR | 404 |
| | ≥25 μm | 0 | 2 | 1 | 3 | NR | 4 | 2 | NR | 0 |
| Particulate analysis by MFI (particles/mL) | 2 to 10 μm | 790 | 3455 | 2674 | 2872 | NR | 5749 | 6190 | NR | 4523 |
| | ≥10 μm | 2 | 53 | 13 | 23 | NR | 69 | 33 | NR | 116 |
| | ≥25 μm | 0 | 5 | 2 | 3 | NR | 0 | 0 | NR | 0 |
| Non-reduced MCE | % Main Peak Purity | 96.9 | 96.4 | 96.0 | 95.3 | NR | 94.6 | 92.5 | NR | 97.0 |
| | % LMW Species | 3.0 | 3.3 | 3.6 | 4.3 | NR | 4.4 | 6.2 | NR | 3.0 |
| | % HMW Species | 0.2 | 0.3 | 0.4 | 0.5 | NR | 1.0 | 1.3 | NR | 0.1 |

TABLE 29-continued

Research Stability of 150 mg/mL mAb1 Drug Product in 1 mL BD Neopak Syringes
Stored at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
BD Neopak SCF 1 mL long glass syringe with 27G thing wall needle
and BD260 needle shield

|  | Assay | 25° C./60% RH Storage (months) | | | | 40° C./75% RH Storage (months) | | | Orbital shaking (h) | |
| --- | --- | --- | --- | --- | --- | --- | --- | --- | --- | --- |
|  |  | 0 | 1 | 3 | 6 | 0.5 | 1 | 2 | 24 | 48 |
| Reduced | % Purity | 95.4 | 95.2 | 94.3 | 93.9 | NR | 93.4 | 91.7 | NR | 95.2 |
| MCE | % LMW Species | 1.7 | 2.0 | 2.5 | 2.8 | NR | 3.1 | 4.4 | NR | 1.8 |
|  | % NGHC | 1.2 | 1.2 | 1.6 | 1.4 | NR | 1.7 | 2.0 | NR | 1.1 |
| Purity by | % HMW | 0.5 | 0.8 | 1.0 | 1.3 | 1.2 | 1.9 | 3.7 | 0.5 | 0.5 |
| SE-UPLC | % Native | 99.3 | 99.0 | 98.8 | 98.4 | 98.2 | 97.4 | 95.7 | 99.3 | 99.3 |
|  | % LMW | 0.3 | 0.2 | 0.2 | 0.3 | 0.6 | 0.7 | 0.6 | 0.3 | 0.3 |
| Charge | % Acidic | 20.1 | 20.3 | 24.3 | 28.8 | 25.7 | 32.0 | 55.1 | 19.9 | 19.9 |
| variant | % Main | 68.1 | 67.0 | 63.5 | 58.9 | 60.7 | 54.1 | 33.3 | 68.0 | 67.7 |
| analysis by | % Basic | 11.8 | 12.6 | 12.2 | 12.3 | 13.6 | 13.9 | 11.6 | 12.1 | 12.4 |
| CEX-UPLC |  |  |  |  |  |  |  |  |  |  |
| Charge | % Acidic | 30.8 | 31.7 | 32.9 | 37.3 | NR | 40.1 | 56.7 | NR | 30.6 |
| variant | % Main | 57.5 | 55.4 | 53.3 | 48.7 | NR | 43.1 | 25.8 | NR | 57.5 |
| analysis by | % Basic | 11.7 | 12.9 | 13.8 | 14.1 | NR | 16.8 | 17.5 | NR | 11.9 |
| iCIEF |  |  |  |  |  |  |  |  |  |  |
|  | % Polysorbate 80 by CAD | 0.082 | 0.080 | 0.082 | 0.089 | NR | 0.080 | 0.081 | NR | 0.081 |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RH = Relative humidity;
RP = Reverse phase;
SE = Size exclusion;
UPLC = Ultra-performance liquid chromatography

TABLE 30

Research Stability of 150 mg/mL mAb1 Drug Product in 2.25 mL gOmpi Syringes Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.14 mL
Container/Closure
Nuova Ompi EZ-Fill 2.25 mL glass syringe with 27G thin wall needle
with FM30 needle shield

|  | Assay | Length of Storage at 2-8° C. (months) | | | | | | | | |
| --- | --- | --- | --- | --- | --- | --- | --- | --- | --- | --- |
|  |  | 0 | 1 | 3 | 6 | 9 | 12 | 18 | 24 | 36 |
| Color and appearance | | Pass | Pass | Pass | Pass | Pass | Pass | Pass | | |
| Turbidity (Increase in OD at 405 nm) | | 0.00 | 0.00 | 0.00 | 0.00 | 0.01 | 0.00 | 0.00 | | |
| pH | | 5.4 | 5.3 | 5.3 | 5.2 | 5.2 | 5.3 | 5.3 | | |
| % Protein recovered by SEC-UPLC | | 100 | 100 | 100 | 98 | 100 | 103 | 102 | | |
| Subvisible | ≥10 μm | 3104 | 790 | 2428 | 3381 | NR | 2406 | NR | | |
| particulate | ≥25 μm | 2 | 1 | 11 | 35 | NR | 15 | NR | | |
| analysis by HIAC (#/mL) | | | | | | | | | | |
| Particulate | 2 to 10 μm | 18565 | 22777 | 16440 | 24709 | NR | 12492 | NR | | |
| analysis by | ≥10 μm | 146 | 325 | 107 | 156 | NR | 107 | NR | | |
| MFI | ≥25 μm | 0 | 1 | 0 | 3 | NR | 3 | NR | | |
| (particles/mL) | | | | | | | | | | |

TABLE 30-continued

Research Stability of 150 mg/mL mAb1 Drug Product in 2.25 mL gOmpi Syringes Stored at 2-8° C.

Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.14 mL
Container/Closure
Nuova Ompi EZ-Fill 2.25 mL glass syringe with 27G thin wall needle with FM30 needle shield Length of Storage at 2-8° C. (months)

| | Assay | 0 | 1 | 3 | 6 | 9 | 12 | 18 | 24 | 36 |
|---|---|---|---|---|---|---|---|---|---|---|
| Non-reduced MCE | % Main Peak Purity | 97.1 | 97.0 | 97.3 | 97.3 | NR | 97.6 | NR | | |
| | % LMW Species | 2.9 | 2.9 | 2.6 | 2.6 | NR | 2.1 | NR | | |
| | % HMW Species | 0.1 | 0.1 | 0.1 | 0.1 | NR | 0.3 | NR | | |
| Reduced MCE | % Purity | 94.5 | 95.3 | 95.4 | 94.7 | NR | 94.6 | NR | | |
| | % LMW Species | 2.1 | 2.1 | 1.5 | 1.9 | NR | 1.9 | NR | | |
| | % NGHC | 1.5 | 1.0 | 1.2 | 1.6 | NR | 1.8 | NR | | |
| Purity by SE-UPLC | % HMW | 0.5 | 0.5 | 0.6 | 0.7 | 0.7 | 0.8 | 0.8 | | |
| | % Native | 99.3 | 99.3 | 99.2 | 99.1 | 99.0 | 99.0 | 99.0 | | |
| | % LMW | 0.3 | 0.2 | 0.2 | 0.2 | 0.3 | 0.3 | 0.3 | | |
| Charge variant analysis by CEX-UPLC | % Acidic | 20.2 | 19.4 | 19.8 | 19.7 | 19.3 | 18.5 | 19.1 | | |
| | % Main | 68.0 | 68.4 | 68.8 | 68.9 | 69.0 | 70.7 | 69.8 | | |
| | % Basic | 11.9 | 12.2 | 11.4 | 11.4 | 11.7 | 10.9 | 11.1 | | |
| Charge variant analysis by iCIEF | % Acidic | 31.1 | NR | 30.6 | 30.8 | NR | 31.2 | NR | | |
| | % Main | 57.3 | NR | 58.3 | 57.4 | NR | 56.8 | NR | | |
| | % Basic | 11.6 | NR | 11.1 | 11.8 | NR | 12.0 | NR | | |
| % Polysorbate 80 by CAD | | 0.080 | 0.081 | 0.082 | 0.091 | NR | 0.091 | NR | | |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RP = Reverse phase;
SE = Size exclusion;
UPLC = Ultra-performance liquid chromatography

TABLE 31

Research Stability of 150 mg/mL mAb1 Drug Product in 2.25 mL gOmpi Syringes Stored at Accelerated and Stress Conditions, and Against Agitation Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.14 mL
Container/Closure
Nuova Ompi EZ-Fill 2.25 mL glass syringe with 27G thin wall needle with FM30 needle shield

| | | 25° C./60% RH Storage (months) | | | | 40° C./75% RH Storage (months) | | | Orbital shaking (h) | |
|---|---|---|---|---|---|---|---|---|---|---|
| Assay | | 0 | 1 | 3 | 6 | 0.5 | 1 | 2 | 24 | 48 |
| Color and appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.01 | 0.02 | 0.00 | 0.00 |
| pH | | 5.4 | 5.3 | 5.3 | 5.3 | 5.2 | 5.3 | 5.3 | 5.3 | 5.2 |
| % Protein recovered by RP-UPLC | | 100 | 100 | 100 | 99 | 99 | 100 | 100 | 99 | 99 |
| Subvisible particulate analysis by HIAC (#/mL) | ≥10 µm | 3104 | 1045 | 1956 | 2270 | NR | 2339 | 1362 | NR | 3139 |
| | ≥25 µm | 2 | 1 | 2 | 11 | NR | 0 | 1 | NR | 11 |
| Particulate analysis by MFI (particles/mL) | 2 to 10 µm | 18565 | 21342 | 12788 | 13835 | NR | 13671 | 9727 | NR | 28368 |
| | ≥10 µm | 146 | 394 | 120 | 79 | NR | 1112 | 80 | NR | 674 |
| | ≥25 µm | 0 | 0 | 7 | 3 | NR | 8 | 2 | NR | 0 |

TABLE 31-continued

Research Stability of 150 mg/mL mAb1 Drug Product in 2.25 mL gOmpi Syringes
Stored at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.14 mL
Container/Closure
Nuova Ompi EZ-Fill 2.25 mL glass syringe with 27G thin wall needle
with FM30 needle shield

| | Assay | 25° C./60% RH Storage (months) | | | | 40° C./75% RH Storage (months) | | | Orbital shaking (h) | |
|---|---|---|---|---|---|---|---|---|---|---|
| | | 0 | 1 | 3 | 6 | 0.5 | 1 | 2 | 24 | 48 |
| Non-reduced MCE | % Main Peak Purity | 97.1 | 96.6 | 96.6 | 95.6 | NR | 94.7 | 92.8 | NR | 97.2 |
| | % LMW Species | 2.9 | 3.2 | 3.1 | 3.8 | NR | 4.4 | 6.0 | NR | 2.7 |
| | % HMW Species | 0.1 | 0.2 | 0.4 | 0.6 | NR | 0.9 | 1.2 | NR | 0.1 |
| Reduced MCE | % Purity | 94.5 | 95.1 | 94.8 | 94.8 | NR | 93.4 | 91.8 | NR | 94.8 |
| | % LMW Species | 2.1 | 1.9 | 1.8 | 2.3 | NR | 3.3 | 4.9 | NR | 2.1 |
| | % NGHC | 1.5 | 1.1 | 1.8 | 1.3 | NR | 1.6 | 1.4 | NR | 1.4 |
| Purity by SE-UPLC | % HMW | 0.5 | 0.8 | 1.0 | 1.3 | 1.2 | 1.9 | 3.7 | 0.5 | 0.5 |
| | % Native | 99.3 | 99.0 | 98.8 | 98.4 | 98.2 | 97.4 | 95.7 | 99.3 | 99.3 |
| | % LMW | 0.3 | 0.2 | 0.2 | 0.3 | 0.6 | 0.7 | 0.6 | 0.3 | 0.3 |
| Charge variant analysis by CEX-UPLC | % Acidic | 20.2 | 20.8 | 23.9 | 28.7 | 25.8 | 32.1 | 54.7 | 20.2 | 19.8 |
| | % Main | 68.0 | 66.4 | 64.0 | 59.0 | 60.6 | 54.3 | 33.6 | 67.8 | 67.9 |
| | % Basic | 11.9 | 12.8 | 12.1 | 12.3 | 13.6 | 13.6 | 11.7 | 12.0 | 12.4 |
| Charge variant analysis by iCIEF | % Acidic | 31.1 | 31.1 | 37.0 | 37.6 | NR | 40.3 | 57.4 | NR | 30.5 |
| | % Main | 57.3 | 56.0 | 50.9 | 48.1 | NR | 44.5 | 26.8 | NR | 57.5 |
| | % Basic | 11.6 | 12.9 | 12.1 | 14.2 | NR | 15.3 | 15.8 | NR | 12.0 |
| | % Polysorbate 80 by CAD | 0.080 | 0.081 | 0.082 | 0.090 | NR | 0.080 | 0.081 | NR | 0.080 |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RH = Relative humidity;
RP = Reverse phase;
SE = Size exclusion;
UPLC = Ultra-performance liquid chromatography

TABLE 32

Research Stability of 150 mg/mL mAb1 Drug Product in 2.25 mL BD Neopak Syringes Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.14 mL
Container/Closure
BD Neopak SCF 2.25 mL long glass syringe, 27G thin wall needle
and BD260 needle shield

| | Assay | Length of Storage at 2-8° C. (months) | | | | | | | | |
|---|---|---|---|---|---|---|---|---|---|---|
| | | 0 | 1 | 3 | 6 | 9 | 12 | 18 | 24 | 36 |
| | Color and appearance | Pass | Pass | Pass | Pass | Pass | Pass | Pass | | |
| | Turbidity (Increase in OD at 405 nm) | 0.00 | 0.00 | 0.00 | 0.00 | 0.01 | 0.00 | 0.00 | | |
| | pH | 5.4 | 5.3 | 5.3 | 5.2 | 5.2 | 5.2 | 5.3 | | |
| | % Protein recovered by SEC-UPLC | 100 | 101 | 100 | 99 | 100 | 102 | 103 | | |
| Subvisible particulate analysis by HIAC (#/mL) | ≥10 μm | 296 | 363 | 513 | 560 | NR | 573 | NR | | |
| | ≥25 μm | 0 | 1 | 1 | 6 | NR | 5 | NR | | |

TABLE 32-continued

Research Stability of 150 mg/mL mAb1 Drug Product in 2.25 mL BD Neopak Syringes Stored at 2-8° C.

Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.14 mL
Container/Closure
BD Neopak SCF 2.25 mL long glass syringe, 27G thin wall needle and BD260 needle shield
Length of Storage at 2-8° C. (months)

| | Assay | 0 | 1 | 3 | 6 | 9 | 12 | 18 | 24 | 36 |
|---|---|---|---|---|---|---|---|---|---|---|
| Particulate analysis by MFI (particles/mL) | 2 to 10 μm | 3562 | 14700 | 6832 | 12464 | NR | 6453 | NR | | |
| | ≥10 μm | 25 | 176 | 18 | 20 | NR | 41 | NR | | |
| | ≥25 μm | 2 | 1 | 2 | 2 | NR | 5 | NR | | |
| Non-reduced MCE | % Main Peak Purity | 97.8 | 97.0 | 97.5 | 97.2 | NR | 97.3 | NR | | |
| | % LMW Species | 2.2 | 2.9 | 2.3 | 2.5 | NR | 2.3 | NR | | |
| | % HMW Species | 0.1 | 0.1 | 0.2 | 0.3 | NR | 0.4 | NR | | |
| Reduced MCE | % Purity | 94.9 | 95.0 | 94.1 | 94.4 | NR | 94.8 | NR | | |
| | % LMW Species | 1.7 | 2.0 | 2.2 | 2.0 | NR | 2.0 | NR | | |
| | % NGHC | 1.6 | 1.4 | 2.0 | 1.7 | NR | 1.6 | NR | | |
| Purity by SE-UPLC | % HMW | 0.5 | 0.5 | 0.6 | 0.6 | 0.7 | 0.8 | 0.8 | | |
| | % Native | 99.3 | 99.3 | 99.2 | 99.1 | 99.1 | 99.0 | 98.9 | | |
| | % LMW | 0.3 | 0.2 | 0.2 | 0.2 | 0.3 | 0.3 | 0.3 | | |
| Charge variant analysis by CEX-UPLC | % Acidic | 20.2 | 19.9 | 19.9 | 19.8 | 19.2 | 18.2 | 19.3 | | |
| | % Main | 67.9 | 67.9 | 68.8 | 68.8 | 69.1 | 70.9 | 69.9 | | |
| | % Basic | 12.0 | 12.2 | 11.3 | 11.4 | 11.7 | 10.9 | 10.9 | | |
| Charge variant analysis by iCIEF | % Acidic | 31.2 | 30.7 | 30.4 | 30.6 | NR | 32.5 | NR | | |
| | % Main | 57.1 | 57.7 | 58.3 | 58.1 | NR | 55.1 | NR | | |
| | % Basic | 11.7 | 11.6 | 11.3 | 11.3 | NR | 12.4 | NR | | |
| % Polysorbate 80 by CAD | | 0.80 | 0.081 | 0.082 | 0.091 | NR | 0.091 | NR | | |
| % Relative potency (bioassay) | | 99 | NR | NR | 128 | NR | NA | NR | | |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RP = Reverse phase;
SE = Size exclusion;
UPLC = Ultra-performance liquid chromatography

TABLE 33

Research Stability of 150 mg/mL mAb1 Drug Product in 2.25 mL BD Neopak Syringes Stored at Accelerated and Stress Conditions, and Against Agitation Formulation
150 mg/mL mAb1, 10 mM acetate, 5% (w/v) sucrose, 70 mM L-arginine hydrochloride, 0.08% (w/v) polysorbate 80, pH 5.3
Fill Volume
2.14 mL
Container/Closure
BD Neopak SCF 2.25 mL long glass syringe, 27G thin wall needle and BD260 needle shield

| | 25° C./60% RH Storage (months) | | | | 40° C./75% RH Storage (months) | | | Orbital shaking (h) | |
|---|---|---|---|---|---|---|---|---|---|
| Assay | 0 | 1 | 3 | 6 | 0.5 | 1 | 2 | 24 | 48 |
| Color and appearance | Pass | Pass | Pass | Pass | Pass | Pass | Pass | Pass | Pass |
| Turbidity (Increase in OD at 405 nm) | 0.00 | 0.00 | 0.00 | 0.00 | 0.01 | 0.01 | 0.02 | 0.00 | 0.00 |
| pH | 5.4 | 5.3 | 5.3 | 5.3 | 5.2 | 5.3 | 5.3 | 5.3 | 5.3 |
| % Protein recovered by RP-UPLC | 100 | 100 | 100 | 100 | 99 | 100 | 101 | 100 | 99 |

TABLE 33-continued

Research Stability of 150 mg/mL mAb1 Drug Product in 2.25 mL BD Neopak Syringes
Stored at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
2.14 mL
Container/Closure
BD Neopak SCF 2.25 mL long glass syringe, 27G thin wall needle
and BD260 needle shield

| | | 25° C./60% RH Storage (months) | | | | 40° C./75% RH Storage (months) | | | Orbital shaking (h) | |
|---|---|---|---|---|---|---|---|---|---|---|
| | Assay | 0 | 1 | 3 | 6 | 0.5 | 1 | 2 | 24 | 48 |
| Subvisible particulate analysis by HIAC (#/mL) | ≥10 μm | 296 | 479 | 698 | 357 | NR | 468 | 609 | NR | 642 |
| | ≥25 μm | 0 | 0 | 1 | 2 | NR | 1 | 1 | NR | 1 |
| Particulate analysis by MFI (particles/mL) | 2 to 10 μm | 3562 | 11550 | 7486 | 6464 | NR | 12808 | 9128 | NR | 13532 |
| | ≥10 μm | 25 | 154 | 38 | 36 | NR | 179 | 48 | NR | 243 |
| | ≥25 μm | 2 | 1 | 2 | 5 | NR | 5 | 0 | NR | 3 |
| Non-reduced MCE | % Main Peak Purity | 97.8 | 96.9 | 96.5 | 95.9 | NR | 95.4 | 93.2 | NR | 97.2 |
| | % LMW Species | 2.2 | 3.0 | 3.2 | 3.6 | NR | 4.1 | 5.5 | NR | 2.7 |
| | % HMW Species | 0.1 | 0.2 | 0.3 | 0.5 | NR | 0.5 | 1.3 | NR | 0.1 |
| Reduced MCE | % Purity | 94.9 | 94.7 | 94.2 | 93.9 | NR | 93.7 | 92.0 | NR | 94.9 |
| | % LMW Species | 1.7 | 2.0 | 2.2 | 2.5 | NR | 2.8 | 4.3 | NR | 1.8 |
| | % NGHC | 1.6 | 1.5 | 1.8 | 2.0 | NR | 1.8 | 2.1 | NR | 1.7 |
| Purity by SE-UPLC | % HMW | 0.5 | 0.8 | 1.0 | 1.3 | 1.2 | 1.9 | 3.6 | 0.5 | 0.5 |
| | % Native | 99.3 | 99.0 | 98.8 | 98.4 | 98.2 | 97.5 | 95.8 | 99.3 | 99.3 |
| | % LMW | 0.3 | 0.2 | 0.2 | 0.3 | 0.6 | 0.7 | 0.6 | 0.3 | 0.2 |
| Charge variant analysis by CEX-UPLC | % Acidic | 20.2 | 19.8 | 23.9 | 28.6 | 26.0 | 31.8 | 54.9 | 19.9 | 19.9 |
| | % Main | 67.9 | 67.7 | 64.0 | 59.1 | 60.3 | 54.5 | 33.9 | 68.2 | 67.8 |
| | % Basic | 12.0 | 12.5 | 12.2 | 12.3 | 13.7 | 13.8 | 11.3 | 12.0 | 12.2 |
| Charge variant analysis by iCIEF | % Acidic | 31.2 | 31.7 | 33.6 | 38.0 | NR | 40.1 | 56.4 | NR | 30.7 |
| | % Main | 57.1 | 55.3 | 52.7 | 47.9 | NR | 43.1 | 26.4 | NR | 57.9 |
| | % Basic | 11.7 | 13.0 | 13.7 | 14.1 | NR | 16.9 | 17.2 | NR | 11.5 |
| | % Polysorbate 80 by CAD | 0.80 | 0.081 | 0.082 | 0.090 | NR | 0.080 | 0.081 | NR | 0.081 |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RH = Relative humidity;
RP = Reverse phase;
SE = Size exclusion;
UPLC = Ultra-performance liquid chromatography

TABLE 34

Research Stability of 150 mg/mL mAb1 Drug Product in 1 mL SiOPlasma Syringes Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
1 mL SiOPlasma syringe with 27-gauge thin wall needle

| | Length of Storage at 2-8° C. (months) | | | | | | | | |
|---|---|---|---|---|---|---|---|---|---|
| Assay | 0 | 1 | 3 | 6 | 9 | 12 | 18 | 24 | 36 |
| Color and appearance | Pass | Pass | Pass | Pass | Pass | Pass | Pass | | |
| Turbidity (Increase in OD at 405 nm) | 0.00 | 0.00 | 0.00 | 0.00 | 0.00 | 0.00 | 0.00 | | |
| pH | 5.4 | 5.3 | 5.3 | 5.3 | 5.2 | 5.2 | 5.2 | | |
| % Protein recovered by SEC-UPLC | 100 | 100 | 102 | 99 | 101 | 103 | 102 | | |

TABLE 34-continued

Research Stability of 150 mg/mL mAb1 Drug Product in 1 mL SiOPlasma Syringes Stored at 2-8° C.

Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
1 mL SiOPlasma syringe with 27-gauge thin wall needle

| | Assay | \multicolumn{9}{c}{Length of Storage at 2-8° C. (months)} |
|---|---|---|---|---|---|---|---|---|---|---|
| | | 0 | 1 | 3 | 6 | 9 | 12 | 18 | 24 | 36 |
| Subvisible particulate analysis by HIAC (#/mL) | ≥10 μm | 16 | 14 | 25 | 18 | NR | 24 | NR | | |
| | ≥25 μm | 0 | 1 | 1 | 2 | NR | 2 | NR | | |
| Particulate analysis by MFI (particles/mL) | 2 to 10 μm | 241 | 333 | 295 | 334 | NR | 338 | NR | | |
| | ≥10 μm | 7 | 23 | 23 | 23 | NR | 23 | NR | | |
| | ≥25 μm | 2 | 5 | 0 | 2 | NR | 5 | NR | | |
| Non-reduced MCE | % Main Peak Purity | 97.4 | 97.6 | 97.4 | 97.3 | NR | 97.7 | NR | | |
| | % LMW Species | 2.5 | 2.3 | 2.5 | 2.6 | NR | 2.0 | NR | | |
| | % HMW Species | 0.1 | 0.1 | 0.1 | 0.1 | NR | 0.3 | NR | | |
| Reduced MCE | % Purity | 95.7 | 95.1 | 94.7 | 94.5 | NR | 94.1 | NR | | |
| | % LMW Species | 1.5 | 1.9 | 2.1 | 2.1 | NR | 2.3 | NR | | |
| | % NGHC | 1.0 | 1.3 | 1.4 | 1.7 | NR | 1.8 | NR | | |
| Purity by SE-UPLC | % HMW | 0.5 | 0.5 | 0.6 | 0.7 | 0.7 | 0.7 | 0.8 | | |
| | % Native | 99.3 | 99.3 | 99.2 | 99.1 | 99.1 | 99.0 | 98.9 | | |
| | % LMW | 0.3 | 0.2 | 0.2 | 0.2 | 0.3 | 0.3 | 0.3 | | |
| Charge variant analysis by CEX-UPLC | % Acidic | 19.9 | 19.7 | 19.7 | 19.8 | 19.3 | 18.2 | 19.3 | | |
| | % Main | 68.1 | 68.1 | 68.8 | 68.7 | 69.0 | 70.9 | 69.6 | | |
| | % Basic | 11.9 | 12.2 | 11.5 | 11.5 | 11.7 | 10.9 | 11.1 | | |
| Charge variant analysis by iCIEF | % Acidic | 31.2 | 30.7 | 30.4 | 30.6 | NR | 31.5 | NR | | |
| | % Main | 57.1 | 57.7 | 58.3 | 58.1 | NR | 56.7 | NR | | |
| | % Basic | 11.7 | 11.6 | 11.3 | 11.3 | NR | 11.9 | NR | | |
| % Polysorbate 80 by CAD | | 0.081 | 0.081 | 0.081 | 0.091 | NR | 0.092 | NR | | |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RP = Reverse phase;
SE = Size exclusion;
UPLC = Ultra-performance liquid chromatography

TABLE 35

Research Stability of 150 mg/mL mAb1 Drug Product in 1 mL SiOPlasma Syringes
Stored at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
1 mL SiOPlasma syringe with 27-gauge thin wall needle

| | 25° C./60% RH Storage (months) | | | | 40° C./75% RH Storage (months) | | | Orbital shaking (h) | |
|---|---|---|---|---|---|---|---|---|---|
| Assay | 0 | 1 | 3 | 6 | 0.5 | 1 | 2 | 24 | 48 |
| Color and appearance | Pass | Pass | Pass | Pass | Pass | Pass | Pass | Pass | Pass |
| Turbidity (Increase in OD at 405 nm) | 0.00 | 0.00 | 0.00 | 0.00 | 0.00 | 0.01 | 0.02 | 0.00 | 0.00 |
| pH | 5.4 | 5.2 | 5.3 | 5.3 | 5.2 | 5.3 | 5.3 | 5.3 | 5.3 |
| % Protein recovered by RP-UPLC | 100 | 100 | 101 | 99 | 101 | 101 | 101 | 100 | 99 |

TABLE 35-continued

Research Stability of 150 mg/mL mAb1 Drug Product in 1 mL SiOPlasma Syringes
Stored at Accelerated and Stress Conditions, and Against Agitation Formulation
150 mg/mL mAb1, 10 mM acetate, 5% (w/v) sucrose, 70 mM L-arginine
hydrochloride, 0.08% (w/v) polysorbate 80, pH 5.3
Fill Volume
1.05 mL
Container/Closure
1 mL SiOPlasma syringe with 27-gauge thin wall needle

| | Assay | 25° C./60% RH Storage (months) | | | | 40° C./75% RH Storage (months) | | | Orbital shaking (h) | |
|---|---|---|---|---|---|---|---|---|---|---|
| | | 0 | 1 | 3 | 6 | 0.5 | 1 | 2 | 24 | 48 |
| Subvisible particulate analysis by HIAC (#/mL) | ≥10 μm | 16 | 8 | 11 | 19 | NR | 14 | 32 | NR | 21 |
| | ≥25 μm | 0 | 0 | 0 | 1 | NR | 0 | 1 | NR | 0 |
| Particulate analysis by MFI (particles/mL) | 2 to 10 μm | 241 | 437 | 774 | 11 | NR | 509 | 495 | NR | 518 |
| | ≥10 μm | 7 | 31 | 457 | 23 | NR | 62 | 26 | NR | 8 |
| | ≥25 μm | 2 | 3 | 774 | 11 | NR | 7 | 2 | NR | 0 |
| Non-reduced MCE | % Main Peak Purity | 97.4 | 97.0 | 96.6 | 95.6 | NR | 94.7 | 93.1 | NR | 97.2 |
| | % LMW Species | 2.5 | 2.7 | 3.0 | 3.7 | NR | 4.2 | 5.4 | NR | 2.7 |
| | % HMW Species | 0.1 | 0.3 | 0.5 | 0.7 | NR | 1.1 | 1.5 | NR | 0.1 |
| Reduced MCE | % Purity | 95.7 | 94.5 | 94.9 | 94.1 | NR | 93.6 | 92.7 | NR | 95.6 |
| | % LMW Species | 1.5 | 2.0 | 2.0 | 2.2 | NR | 3.0 | 4.2 | NR | 1.7 |
| | % NGHC | 1.0 | 1.7 | 1.5 | 1.7 | NR | 1.6 | 1.5 | NR | 1.0 |
| Purity by SE-UPLC | % HMW | 0.5 | 0.8 | 1.0 | 1.3 | 1.2 | 1.9 | 3.8 | 0.5 | 0.5 |
| | % Native | 99.3 | 99.0 | 98.8 | 98.4 | 98.2 | 97.4 | 95.6 | 99.2 | 99.3 |
| | % LMW | 0.3 | 0.2 | 0.2 | 0.3 | 0.6 | 0.7 | 0.6 | 0.3 | 0.3 |
| Charge variant analysis by CEX-UPLC | % Acidic | 19.9 | 21.0 | 24.1 | 63.6 | 26.0 | 32.0 | 54.7 | 20.0 | 19.8 |
| | % Main | 68.1 | 66.2 | 28.7 | 59.1 | 60.7 | 54.0 | 33.5 | 67.9 | 67.8 |
| | % Basic | 11.9 | 12.7 | 24.1 | 63.6 | 13.3 | 14.0 | 11.8 | 12.0 | 12.4 |
| Charge variant analysis by iCIEF | % Acidic | 31.2 | 31.7 | 33.6 | 38.0 | NR | 40.1 | 56.4 | NR | 30.7 |
| | % Main | 57.1 | 55.3 | 52.7 | 47.9 | NR | 43.1 | 26.4 | NR | 57.9 |
| | % Basic | 11.7 | 13.0 | 13.7 | 14.1 | NR | 16.9 | 17.2 | NR | 11.5 |
| % Polysorbate 80 by CAD | | 0.081 | 0.081 | 0.082 | 0.091 | NR | 0.081 | 0.082 | NR | 0.081 |

CEX = Cation exchange;
DS = Drug substance;
FDG = Formulation Development group;
HMW = High molecular weight;
iCIEF = Imaged capillary isoelectric focusing;
LMW = Low molecular weight;
MCE-SDS = Microchip capillary electrophoresis-sodium dodecyl sulfate;
MFI = Microflow imaging;
NR = Not required;
OD = Optical density;
RH = Relative humidity;
RP = Reverse phase;
SE = Size exclusion;
UPLC = Ultra-performance liquid chromatography

TABLE 36

Research Stability of 75 mg/mL mAb1 Drug Product in Glass Vials Stored at 2-8° C.

Formulation
75 mg/mL mAb1, 10 mM acetate, 5% (w/v) sucrose, 70 mM L-arginine
hydrochloride, 0.08% (w/v) polysorbate 80, pH 5.3
Fill Volume
2.5 mL
Container/Closure
Type 1 borosilicate ISO 6R glass vials with a 20 mm FluroTec ®
coated West WPS-1343 4023/50 B2-40 stoppers

| Assay | Length of Storage at 2-8° C. (months) | | | | | | | | | |
|---|---|---|---|---|---|---|---|---|---|---|
| | 0 | 1 | 2 | 3 | 6 | 9 | 12 | 18 | 24 | 36 |
| Color and Appearance | Pass | Pass | Pass | Pass | Pass | Pass | Pass | | | |
| Turbidity (increase in OD at 405 | 0.00 | 0.00 | 0.01 | 0.01 | 0.01 | 0.00 | 0.01 | | | |
| pH | 5.3 | 5.3 | 5.3 | 5.3 | 5.2 | 5.3 | 5.3 | | | |

TABLE 36-continued

Research Stability of 75 mg/mL mAb1 Drug Product in Glass Vials Stored at 2-8° C.

Formulation
75 mg/mL mAb1, 10 mM acetate, 5% (w/v) sucrose, 70 mM L-arginine hydrochloride, 0.08% (w/v) polysorbate 80, pH 5.3
Fill Volume
2.5 mL
Container/Closure
Type 1 borosilicate ISO 6R glass vials with a 20 mm FluroTec ® coated West WPS-1343 4023/50 B2-40 stoppers

| | Assay | \multicolumn{9}{c}{Length of Storage at 2-8° C. (months)} | | | | | | | | |
|---|---|---|---|---|---|---|---|---|---|---|---|
| | | 0 | 1 | 2 | 3 | 6 | 9 | 12 | 18 | 24 | 36 |
| Subvisible Particulate Analysis by HIAC (N/mL) | ≥10 μm | 4 | 7 | 6 | 7 | 3 | NR | 3 | | | |
| | ≥25 μm | 0 | 1 | 1 | 2 | 1 | NR | 0 | | | |
| Subvisible Particulate Analysis by MFI (N/mL) | 2 to 10 μm | 238 | 373 | 398 | 578 | 677 | NR | 776 | | | |
| | ≥10 μm | 7 | 13 | 10 | 7 | 21 | NR | 21 | | | |
| | ≥25 μm | 2 | 0 | 2 | 2 | 3 | NR | 3 | | | |
| | % Protein Recovered by SE-UPLC | 100 | 102 | 102 | 100 | 101 | 100 | 100 | | | |
| Non-reduced MCE | % Main Peak Purity | 97.5 | 97.3 | 97.2 | 97.2 | 97.3 | NR | 97.4 | | | |
| | % LMW Species | 2.5 | 2.7 | 2.6 | 2.6 | 2.6 | NR | 2.3 | | | |
| | % HMW Species | 0.1 | 0.1 | 0.2 | 0.2 | 0.1 | NR | 0.3 | | | |
| Reduced MCE | % Purity | 94.4 | 93.7 | 94.3 | 94.6 | 94.3 | NR | 94.1 | | | |
| | % LMW Species | 1.8 | 2.0 | 2.0 | 1.9 | 2.1 | NR | 2.4 | | | |
| | % NGHC | 2.0 | 1.9 | 1.9 | 1.9 | 1.9 | NR | 1.9 | | | |
| Purity by SE-UPLC | % HMW | 0.4 | 0.5 | 0.5 | 0.5 | 0.5 | 0.5 | 0.6 | | | |
| | % Main peak | 99.3 | 99.3 | 99.3 | 99.3 | 99.2 | 99.1 | 99.2 | | | |
| | % LMW | 0.2 | 0.2 | 0.3 | 0.3 | 0.3 | 0.3 | 0.3 | | | |
| Charge Variant Analysis by CEX-UPLC | % Region 1 | 20.9 | 20.8 | 21.2 | 20.9 | 20.7 | 19.6 | 19.6 | | | |
| | % Region 2 | 69.6 | 69.6 | 69.2 | 69.5 | 69.1 | 71.5 | 70.8 | | | |
| | % Region 3 | 9.5 | 9.6 | 9.7 | 9.7 | 10.2 | 8.9 | 9.6 | | | |
| Charge Variant Analysis by iCIEF | % Region 1 | 35.6 | 35.4 | 34.6 | 34.9 | 33.7 | NR | 33.2 | | | |
| | % Region 2 | 55.3 | 55.5 | 56.3 | 56.4 | 56.4 | NR | 56.6 | | | |
| | % Region 3 | 9.2 | 9.2 | 9.1 | 8.8 | 9.9 | NR | 10.3 | | | |
| | % Relative Potency (bioassay) | 58 | NR | NR | NR | 63 | NR | NA | | | |

CEX, Cation exchange;
DS, Drug substance;
FDG, Formulation development group;
HMW, High molecular weight;
iCIEF, imaged capillary isoelectric-focusing;
LMW, Low molecular weight;
MFI, Microflow- imaging;
Monomer, intact antibody;
NA, Not available;
NR, Not required;
OD, Optical density;
RP, Reverse phase;
SE, Size exclusion;
UPLC, Ultra-performance liquid chromatography The results from the long-term storage, accelerated, and stress stability studies indicate that the mAb1 formulations were stable during manufacture (formulation, fill/finish, and labeling operations), and can withstand short exposures to room temperature without compromising physical or chemical stability.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A stable liquid pharmaceutical formulation comprising:
   (i) a human antibody that specifically binds to human interleukin-33 (hIL-33), wherein the antibody comprises heavy chain complementary determining regions HCDR1, HCDR2, and HCDR3 comprising the amino acid sequences of SEQ ID NOs: 4, 6, and 8, respectively, and light chain complementarity determining regions LCDR1, LCDR2, and LCDR3 comprising the amino acid sequences of SEQ ID NOs: 12, 14, and 16, respectively, wherein the antibody is present at a concentration of from 15 mg/ml to 150 mg/ml;
   (ii) 5 mM to 15 mM acetate;
   (iii) 50 mM to 100 mM arginine hydrochloride;
   (iv) 3% w/v to 7% w/v sucrose; and
   (v) 0.06% w/v to 0.1% w/v polysorbate 80,
   wherein the formulation has a pH of from 5.1 to 5.5, and wherein the formulation exhibits a viscosity of less than about 15 cPoise when measured at 20° C.

2. The stable liquid pharmaceutical formulation of claim 1, wherein the antibody is present at a concentration of 75 mg/ml or 150 mg/ml.

3. The stable liquid pharmaceutical formulation of claim 1, wherein the antibody has a human IgG heavy chain constant region.

4. The stable liquid pharmaceutical formulation of claim 3, wherein the heavy chain constant region is of isotype IgG1.

5. The stable liquid pharmaceutical formulation of claim 3, wherein the heavy chain constant region is of isotype IgG4.

6. The stable liquid pharmaceutical formulation of claim 1, wherein the antibody comprising a heavy chain variable region comprising the amino acid sequence of SEQ ID NO: 2 and a light chain variable region comprising the amino acid sequence of SEQ ID NO: 10.

7. The stable liquid pharmaceutical formulation of claim 1, wherein the formulation has a pH of from 5.2 to 5.4.

8. The stable liquid pharmaceutical formulation of claim 1, comprising:
   (i) 75 mg/ml of the antibody; (ii) 10 mM±2 mM acetate; (iii) 70 mM±14 mM arginine hydrochloride (iv) 5% w/v±1% w/v sucrose; and (iv) 0.08%±0.016% w/v polysorbate 80, wherein the formulation has a pH of from 5.2 to 5.4.

9. The stable liquid pharmaceutical formulation of claim 1, comprising:
   (i) 150 mg/ml of the antibody; (ii) 10 mM±2 mM acetate; (iii) 70 mM±14 mM arginine hydrochloride (iv) 5% w/v±1% w/v sucrose; and (iv) 0.08%±0.016% w/v polysorbate 80, wherein the formulation has a pH of from 5.2 to 5.4.

10. A stable liquid pharmaceutical formulation comprising:
    (i) a human antibody that specifically binds to human interleukin-33 (hIL-33) at a concentration of from 15±1.5 mg/ml to 150±15 mg/ml, wherein the antibody comprises a heavy chain comprising the amino acid sequence of SEQ ID NO: 18 and a light chain comprising the amino acid sequence of SEQ ID NO: 20;
    (ii) 10 mM±2 mM acetate;
    (iii) 70 mM±14 mM arginine hydrochloride;
    (iv) 5% w/v±1% w/v sucrose; and
    (iv) 0.08%±0.016% w/v polysorbate 80,
    wherein the formulation has a pH of from 5.1 to 5.5, and wherein the formulation exhibits a viscosity of less than about 15 cPoise when measured at 20° C.

11. The stable liquid pharmaceutical formulation of claim 10, wherein the antibody is at a concentration of 75 mg/ml±5 mg/ml.

12. The stable liquid pharmaceutical formulation of claim 10, wherein the antibody is at a concentration of 150 mg/ml±15 mg/ml.

13. The stable liquid pharmaceutical formulation of claim 10, wherein the formulation has a pH of from 5.2 to 5.4.

14. The stable liquid pharmaceutical formulation of claim 13, wherein the formulation has a pH of 5.3.

15. The stable liquid pharmaceutical formulation of claim 1 contained in a glass vial.

16. The stable liquid pharmaceutical formulation of claim 1 contained in a syringe.

17. The stable liquid pharmaceutical formulation of claim 16, wherein the syringe comprises a fluorocarbon-coated plunger, or the syringe is a low tungsten syringe.

18. The stable liquid pharmaceutical formulation of claim 16, wherein the syringe is a prefilled syringe, or a prefilled staked needle syringe.

19. The stable liquid pharmaceutical formulation of claim 1 contained in a large volume device or bolus injector.

20. A pen or autoinjector delivery device containing the stable liquid pharmaceutical formulation of claim 1.

21. The delivery device of claim 20 that is a disposable pen delivery device, or a reusable pen delivery device.

22. A container containing the stable liquid pharmaceutical formulation of claim 1.

23. A kit comprising (i) a container containing the stable liquid pharmaceutical formulation of claim 1, and (ii) labeling for use of the pharmaceutical formulation.

24. The kit of claim 23, wherein the labeling recites subcutaneous administration of the pharmaceutical formulation, or the labeling recites intravenous administration of the pharmaceutical formulation.

25. A unit dosage form comprising the stable liquid pharmaceutical formulation of claim 1, wherein the anti-IL-33 antibody is present in an amount of from 1 mg to 500 mg.

26. The unit dosage form of claim 25, wherein the anti-IL-33 antibody is present in an amount of about 150 mg, or in an amount of about 300 mg.

27. The unit dosage form of claim 25, wherein the formulation is contained in a syringe, or a prefilled syringe.

28. A safety system delivery device containing the stable liquid pharmaceutical formulation of claim 1.

29. The safety system delivery device of claim 28, including a safety sleeve configured to extend by manual operation, or including a safety sleeve configured to automatically extend following injection of the stable liquid pharmaceutical formulation.

* * * * *

UNITED STATES PATENT AND TRADEMARK OFFICE
CERTIFICATE OF CORRECTION

| | |
|---|---|
| PATENT NO. | : 11,596,690 B2 |
| APPLICATION NO. | : 16/825007 |
| DATED | : March 7, 2023 |
| INVENTOR(S) | : Qingyan Hu et al. |

It is certified that error appears in the above-identified patent and that said Letters Patent is hereby corrected as shown below:

On the Title Page

Item (73) Assignee:
"Tarytown, NY (US)"
Should read:
--Tarrytown, NY (US)--

Item (74) Attorney, Agent, or Firm:
"Lisa Dombach Flanagan"
Should read:
--Lisa Dornbach Flanagan--

Signed and Sealed this
Twenty-third Day of May, 2023

Katherine Kelly Vidal
*Director of the United States Patent and Trademark Office*